US010808229B2

(12) United States Patent
Kawaoka et al.

(10) Patent No.: US 10,808,229 B2
(45) Date of Patent: *Oct. 20, 2020

(54) HIGH TITER RECOMBINANT INFLUENZA VIRUSES WITH ENHANCED REPLICATION IN VERO CELLS

(71) Applicant: Wisconsin Alumni Research Foundation (WARF), Madison, WI (US)

(72) Inventors: Yoshihiro Kawaoka, Middleton, WI (US); Taisuke Horimoto, Bankyotan (JP); Shin Murakami, Shinagawa-ku (JP)

(73) Assignee: Wisconsin Alumni Research Foundation ("WARF"), Madison, WI (US)

( * ) Notice: Subject to any disclaimer, the term of this patent is extended or adjusted under 35 U.S.C. 154(b) by 1 day.

This patent is subject to a terminal disclaimer.

(21) Appl. No.: 16/046,250

(22) Filed: Jul. 26, 2018

(65) Prior Publication Data

US 2018/0340152 A1 Nov. 29, 2018

Related U.S. Application Data

(63) Continuation of application No. 14/816,807, filed on Aug. 3, 2015, which is a continuation of application No. 12/912,411, filed on Oct. 26, 2010.

(60) Provisional application No. 61/254,795, filed on Oct. 26, 2009.

(51) Int. Cl.

| | |
|---|---|
| ***C12N 7/00*** | (2006.01) |
| ***C07K 14/005*** | (2006.01) |
| *A61K 39/00* | (2006.01) |

(52) U.S. Cl.

CPC .............. *C12N 7/00* (2013.01); *C07K 14/005* (2013.01); *A61K 2039/525* (2013.01); *C12N 2760/16052* (2013.01); *C12N 2760/16122* (2013.01); *C12N 2760/16133* (2013.01); *C12N 2760/16152* (2013.01)

(58) Field of Classification Search

None

See application file for complete search history.

(56) References Cited

U.S. PATENT DOCUMENTS

| | | | |
|---|---|---|---|
| 4,071,618 | A | 1/1978 | Konobe et al. |
| 4,659,569 | A | 4/1987 | Mitsuhashi et al. |
| 5,166,057 | A | 11/1992 | Palese et al. |
| 5,716,821 | A | 2/1998 | Wertz et al. |
| 5,789,229 | A | 8/1998 | Wertz et al. |
| 5,820,871 | A | 10/1998 | Palese et al. |
| 5,840,520 | A | 11/1998 | Clarke et al. |
| 5,854,037 | A | 12/1998 | Palese et al. |
| 5,948,410 | A | 9/1999 | Van Scharrenburg et al. |
| 5,994,526 | A | 11/1999 | Meulewaeter et al. |
| 6,033,886 | A | 3/2000 | Conzelmann |
| 6,037,348 | A | 3/2000 | Colacino et al. |
| 6,146,642 | A | 11/2000 | Garcia-Sastre et al. |
| 6,169,175 | B1 | 1/2001 | Frace et al. |
| 6,194,546 | B1 | 2/2001 | Newton et al. |
| 6,455,298 | B1 | 9/2002 | Groner et al. |
| 6,544,785 | B1 | 4/2003 | Palese et al. |
| 6,656,720 | B2 | 12/2003 | Groner et al. |
| 6,825,036 | B2 | 11/2004 | Makizumi et al. |
| 6,872,395 | B2 | 3/2005 | Kawaoka |
| 6,951,752 | B2 | 10/2005 | Reiter et al. |
| 6,951,754 | B2 | 10/2005 | Hoffmann |
| 6,974,695 | B2 | 12/2005 | Vogels et al. |
| 7,037,707 | B2 | 5/2006 | Webster et al. |
| 7,176,021 | B2 | 2/2007 | Kawaoka |
| 7,226,774 | B2 | 6/2007 | Kawaoka |
| 7,312,064 | B2 | 12/2007 | Hoffmann |
| 7,507,411 | B2 | 3/2009 | Zhou et al. |
| 7,566,458 | B2 | 7/2009 | Yang et al. |
| 7,585,657 | B2 | 9/2009 | Kawaoka |
| 7,588,769 | B2 | 9/2009 | Kawaoka |
| 7,670,837 | B2 | 3/2010 | Schwartz |
| 7,833,788 | B2 | 11/2010 | Pau et al. |
| 7,883,844 | B2 | 2/2011 | Nouchi et al. |
| 7,955,833 | B2 | 6/2011 | Reiter et al. |
| 7,959,930 | B2 | 6/2011 | De Wit et al. |
| 7,972,843 | B2 | 7/2011 | Hoffmann |
| 7,993,924 | B2 | 8/2011 | Billeter et al. |
| 8,012,736 | B2 | 9/2011 | Hoffman et al. |
| 8,048,430 | B2 | 11/2011 | Yang et al. |

(Continued)

FOREIGN PATENT DOCUMENTS

| | | |
|---|---|---|
| AU | 2012204138 B2 | 5/2014 |
| AU | 2014202470 | 11/2016 |

(Continued)

OTHER PUBLICATIONS

"", PNAS, vol. 102, No. 46, (2005), 16825-16829.

(Continued)

*Primary Examiner* — Benjamin P Blumel

(74) *Attorney, Agent, or Firm* — Schwegman Lundberg & Woessner, P.A.

(57) ABSTRACT

The invention provides a composition useful to prepare high titer influenza viruses, e.g., in the absence of helper virus, which includes internal genes from an influenza virus vaccine strain or isolate, e.g., one that is safe in humans, for instance, one that does not result in significant disease, and genes from vaccine seed virus isolates which include a HA gene segment with a HA2 sequence encoding a HA2 that confers enhanced growth in cells in culture, such as Vero cells.

20 Claims, 20 Drawing Sheets

Specification includes a Sequence Listing.

(56) References Cited

U.S. PATENT DOCUMENTS

| | | | |
|---|---|---|---|
| 8,057,806 | B2 | 11/2011 | Kawaoka et al. |
| 8,093,033 | B2 | 1/2012 | Kemble et al. |
| 8,114,415 | B2 | 2/2012 | Hoffmann et al. |
| 8,119,337 | B2 | 2/2012 | Gregersen |
| 8,119,388 | B2 | 2/2012 | Schwartz et al. |
| 8,309,099 | B2 | 11/2012 | Hoffmann |
| 8,354,114 | B2 | 1/2013 | Lu et al. |
| 8,357,376 | B2 | 1/2013 | Liu et al. |
| 8,409,843 | B2 | 4/2013 | Kemble et al. |
| 8,460,914 | B2 | 6/2013 | Gregersen |
| 8,475,806 | B2 | 7/2013 | Kawaoka |
| 8,524,497 | B2 | 9/2013 | Reiter et al. |
| 8,546,123 | B2 | 10/2013 | Lewis |
| 8,574,591 | B2 | 11/2013 | Hoffmann et al. |
| 8,574,593 | B2 | 11/2013 | Yang et al. |
| 8,580,277 | B2 | 11/2013 | Yang et al. |
| 8,591,914 | B2 | 11/2013 | Yang et al. |
| 9,109,013 | B2 | 8/2015 | Kawaoka et al. |
| 9,254,318 | B2 | 2/2016 | Kawaoka et al. |
| 9,474,798 | B2 | 10/2016 | Watanabe et al. |
| 9,890,363 | B2 | 2/2018 | Kawaoka |
| 9,926,535 | B2 | 3/2018 | Kawaoka et al. |
| 9,950,057 | B2 | 4/2018 | Kawaoka et al. |
| 10,053,671 | B2 | 8/2018 | Kawaoka et al. |
| 10,059,925 | B2 | 8/2018 | Kawaoka et al. |
| 2002/0164770 | A1 | 11/2002 | Hoffmann |
| 2002/0197705 | A1 | 12/2002 | Kawaoka |
| 2003/0035814 | A1 | 2/2003 | Kawaoka et al. |
| 2003/0044962 | A1 | 3/2003 | Makizumi et al. |
| 2003/0073223 | A1 | 4/2003 | Groner et al. |
| 2003/0119183 | A1 | 6/2003 | Groner |
| 2003/0194694 | A1 | 10/2003 | Kawaoka |
| 2004/0002061 | A1 | 1/2004 | Kawaoka |
| 2004/0063141 | A1 | 4/2004 | Lok |
| 2004/0077086 | A1 | 4/2004 | Reiter et al. |
| 2004/0219170 | A1 | 11/2004 | Kawaoka |
| 2005/0003349 | A1 | 1/2005 | Kawaoka |
| 2005/0037487 | A1 | 2/2005 | Kawaoka et al. |
| 2005/0118140 | A1 | 6/2005 | Vorlop et al. |
| 2005/0158342 | A1 | 7/2005 | Kemble et al. |
| 2005/0186563 | A1 | 8/2005 | Hoffmann |
| 2005/0202553 | A1 | 9/2005 | Groner et al. |
| 2005/0232950 | A1 | 10/2005 | Kawaoka |
| 2005/0266026 | A1 | 12/2005 | Hoffmann et al. |
| 2006/0057116 | A1 | 3/2006 | Kawaoka et al. |
| 2006/0166321 | A1 | 7/2006 | Kawaoka et al. |
| 2006/0188977 | A1 | 8/2006 | Schwartz et al. |
| 2006/0246092 | A1 | 11/2006 | Neirynck et al. |
| 2007/0231348 | A1 | 10/2007 | Kawaoka et al. |
| 2008/0233560 | A1 | 9/2008 | Hoffmann |
| 2008/0254067 | A1 | 10/2008 | Trepanier et al. |
| 2008/0274141 | A1 | 11/2008 | Groner et al. |
| 2008/0311148 | A1 | 12/2008 | Hoffmann |
| 2008/0311149 | A1 | 12/2008 | Hoffmann |
| 2009/0074812 | A1 | 3/2009 | Watanabe et al. |
| 2009/0081252 | A1 | 3/2009 | Gregersen |
| 2009/0181446 | A1 | 7/2009 | Nouchi et al. |
| 2010/0112000 | A1 | 5/2010 | Schwartz |
| 2010/0183671 | A1 | 7/2010 | Gregersen et al. |
| 2010/0247572 | A1 | 9/2010 | Kawaoka |
| 2011/0027314 | A1 | 2/2011 | Broeker |
| 2011/0045022 | A1 | 2/2011 | Tsai |
| 2011/0110978 | A1 | 5/2011 | Kawaoka et al. |
| 2011/0236417 | A1 | 9/2011 | Watanabe et al. |
| 2012/0020997 | A1 | 1/2012 | Hoffman et al. |
| 2012/0034600 | A1 | 2/2012 | Gregersen |
| 2012/0115206 | A1 | 5/2012 | Schwartz et al. |
| 2012/0156241 | A1 | 6/2012 | De Wit et al. |
| 2012/0207785 | A1 | 8/2012 | Fabry et al. |
| 2013/0095135 | A1 | 4/2013 | Collignon et al. |
| 2013/0183741 | A1 | 7/2013 | Park et al. |
| 2013/0316434 | A1 | 11/2013 | Reiter et al. |
| 2014/0227310 | A1 | 8/2014 | Li et al. |
| 2015/0017205 | A1 | 1/2015 | Kawaoka et al. |
| 2015/0368621 | A1 | 12/2015 | Kawaoka et al. |
| 2016/0024479 | A1 | 1/2016 | Kawaoka et al. |
| 2016/0208223 | A1 | 7/2016 | Kawaoka et al. |
| 2016/0355790 | A1 | 12/2016 | Kawaoka et al. |
| 2017/0067029 | A1 | 3/2017 | Kawaoka et al. |
| 2017/0096645 | A1 | 4/2017 | Watanabe et al. |
| 2017/0258888 | A1 | 9/2017 | Kawaoka |
| 2017/0354730 | A1 | 12/2017 | Kawaoka et al. |
| 2018/0245054 | A1 | 8/2018 | Kawaoka et al. |

FOREIGN PATENT DOCUMENTS

| | | | |
|---|---|---|---|
| CN | 1826407 | B | 9/2013 |
| EP | 0702085 | A1 | 3/1996 |
| EP | 1201760 | A1 | 5/2002 |
| EP | 2010557 | B1 | 2/2014 |
| EP | 1631663 | B1 | 8/2016 |
| IL | 171831 | A | 5/2015 |
| JP | 2004500842 | A | 1/2004 |
| JP | 2005523698 | A | 8/2005 |
| JP | 2005245302 | A | 9/2005 |
| JP | 2005535288 | A | 11/2005 |
| JP | 2009532352 | A | 9/2009 |
| JP | 4927290 | B2 | 2/2012 |
| JP | 4927290 | | 5/2012 |
| JP | 2014039551 | A | 3/2014 |
| JP | 2014131516 | A | 7/2014 |
| JP | 2016144463 | A | 8/2016 |
| JP | 2016524915 | A | 8/2016 |
| JP | 2016169225 | A | 9/2016 |
| JP | 6375329 | B2 | 7/2018 |
| MX | 285206 | | 3/2011 |
| NO | 341506 | | 11/2017 |
| WO | WO-9610631 | A1 | 4/1996 |
| WO | WO-9610632 | A1 | 4/1996 |
| WO | WO-9640955 | A1 | 12/1996 |
| WO | WO-9737000 | A1 | 10/1997 |
| WO | WO-9802530 | A1 | 1/1998 |
| WO | WO-9853078 | A1 | 11/1998 |
| WO | WO-9928445 | A1 | 6/1999 |
| WO | WO-0053786 | A1 | 9/2000 |
| WO | WO-0060050 | A2 | 10/2000 |
| WO | WO-2000060050 | A2 | 10/2000 |
| WO | WO-0060050 | A3 | 1/2001 |
| WO | WO-0179273 | A2 | 10/2001 |
| WO | WO-2001079273 | A2 | 10/2001 |
| WO | WO-0183794 | A2 | 11/2001 |
| WO | WO-2001083794 | A2 | 11/2001 |
| WO | WO-03068923 | A2 | 8/2003 |
| WO | WO-2003068923 | A2 | 8/2003 |
| WO | WO-03076462 | A1 | 9/2003 |
| WO | WO-03091401 | A2 | 11/2003 |
| WO | WO-2003091401 | A2 | 11/2003 |
| WO | WO-04094466 | A2 | 11/2004 |
| WO | WO-2004094466 | A2 | 11/2004 |
| WO | WO-04112831 | A2 | 12/2004 |
| WO | WO-2004112831 | A2 | 12/2004 |
| WO | WO-2005062820 | A2 | 7/2005 |
| WO | WO-2007126810 | A2 | 11/2007 |
| WO | WO-2007126810 | A3 | 11/2007 |
| WO | WO-2008156778 | A2 | 12/2008 |
| WO | WO-2008156778 | A3 | 12/2008 |
| WO | WO-2008157583 | A1 | 12/2008 |
| WO | WO-2008156778 | A9 | 2/2009 |
| WO | WO-2011056591 | A1 | 5/2011 |
| WO | WO-2012177924 | A2 | 12/2012 |
| WO | WO-2013034069 | A1 | 3/2013 |
| WO | WO-2014195920 | A2 | 12/2014 |
| WO | WO-2015009743 | A1 | 1/2015 |
| WO | WO-2015196150 | A2 | 12/2015 |
| WO | WO-2015196150 | A3 | 12/2015 |
| WO | WO-2017007839 | A1 | 1/2017 |
| WO | WO-2017143236 | A1 | 8/2017 |

OTHER PUBLICATIONS

"Adaptation of Egg-Grown and Transfectant Influenza Viruses for Growth in Mammalian Cells: Selection of Hemagglutinin Mutants with Elevated pH of Membrane Fusion", Virology, vol. 233, Issue.

(56) References Cited

OTHER PUBLICATIONS

2, [Online] retrieved from the Internet: http://www.sciencedirect.com/science/article/pii/S0042682297986268, (1997), 402-410.
"U.S. Appl. No. 12/912,411, Advisory Action dated Feb. 5, 2014", 3 pgs.
"U.S. Appl. No. 12/912,411, Examiner Interview Summary dated Feb. 11, 2014", 2 pgs.
"U.S. Appl. No. 12/912,411, Final Office Action dated Jan. 14, 2015", 10 pgs.
"U.S. Appl. No. 12/912,411, Final Office Action dated Oct. 25, 2013", 11 pgs.
"U.S. Appl. No. 12/912,411, Non Final Office Action dated Jun. 7, 2013", 8 pgs.
"U.S. Appl. No. 12/912,411, Non Final Office Action dated Sep. 24, 2014", 11 pgs.
"U.S. Appl. No. 12/912,411, Notice of Allowability dated May 20, 2015", 7 pgs.
"U.S. Appl. No. 12/912,411, Notice of Allowance dated Apr. 8, 2015", 11 pgs.
"U.S. Appl. No. 12/912,411, Response filed Jan. 27, 2014 to Final Office Action dated Oct. 25, 2013", 11 pgs.
"U.S. Appl. No. 12/912,411, Response filed Feb. 18, 2013 to Restriction Requirement dated Oct. 17, 2012", 9 pgs.
"U.S. Appl. No. 12/912,411, Response flied Feb. 25, 2014 to Final Office Action dated Oct. 25, 2013", 11 pgs.
"U.S. Appl. No. 12/912,411, Response filed Mar. 16, 2015 to Final Office Action dated Jan. 14, 2015", 9 pgs.
"U.S. Appl. No. 12/912,411, Response filed Oct. 7, 2013 to Non Final Office Action dated Jun. 7, 2013", 10 pgs.
"U.S. Appl. No. 12/912,411, Response filed Dec. 31, 2014 to Non Final Office Action dated Sep. 24, 2014", 12 pgs.
"U.S. Appl. No. 12/912,411, Restriction Requirement dated Oct. 17, 2012", 9 pgs.
"U.S. Appl. No. 14/745,236, Advisory Action dated Nov. 15, 2017", 2 pgs.
"U.S. Appl. No. 14/745,236, Final Office Action dated Aug. 25, 2017", 16 pgs.
"U.S. Appl. No. 14/745,236, Non Final Office Action dated Feb. 2, 2017", 14 pgs.
"U.S. Appl. No. 14/745,236, Notice of Allowability dated Jul. 5, 2018", 4 pgs.
"U.S. Appl. No. 14/745,236, Notice of Allowance dated Feb. 5, 2018", 9 pgs.
"U.S. Appl. No. 14/745,236, PTO Response to Rule 312 Communication dated Jul. 10, 2018", 2 pgs.
"U.S. Appl. No. 14/745,236, Response filed May 2, 2017 to Non Final Office Action dated Feb. 2, 2017", 10 pgs.
"U.S. Appl. No. 14/745,236, Response filed Nov. 6, 2017 to Final Office Action dated Aug. 25, 2017", 12 pgs.
"U.S. Appl. No. 14/745,236, Response filed Dec. 14, 2017 to Final Office Action dated Aug. 25, 2017", 12 pgs.
"U.S. Appl. No. 14/745,236, Response filed Dec. 23, 2016 to Restriction Requirement dated Sep. 23, 2016", 8 pgs.
"U.S. Appl. No. 14/816,807, Non Final Office Action dated Oct. 3, 2017", 7 pgs.
"U.S. Appl. No. 14/816,807, Notice of Allowance dated Apr. 20, 2018", 8 pgs.
"U.S. Appl. No. 14/816,807, Preliminary Amendment filed Aug. 11, 2015", 8 pgs.
"U.S. Appl. No. 14/816,807, PTO Response to Rule 312 Communication dated Jul. 6, 2018", 2 pgs.
"U.S. Appl. No. 14/816,807, Response filed Jan. 3, 2018 to Non Final Office Action dated Oct. 3, 2017", 8 pgs.
"U.S. Appl. No. 14/816,807, Response filed May 1, 2017 to Restriction Requirement dated Nov. 1, 2016", 9 pgs.
"U.S. Appl. No. 14/816,807, Restriction Requirement dated Nov. 1, 2016", 8 pgs.
"European Application Serial No. 10777154.5, Communication Pursuant to Article 94(3) EPC dated Apr. 4, 2018", 7 pgs.
"European Application Serial No. 10777154.5, Communication Pursuant to Article 94(3) EPC dated Oct. 12, 2017", 7 pgs.
"European Application Serial No. 10777154.5, Examination Notification Art. 94(3) dated Oct. 6, 2014", 7 pgs.
"European Application Serial No. 10777154.5, Office Action dated May 2, 2016", 6 pgs.
"European Application Serial No. 10777154.5, Office Action dated Jul. 4, 2012", 2 pgs.
"European Application Serial No. 10777154.5, Response filed Jan. 14, 2013 to Office Action dated Jul. 4, 2012", 12 pgs.
"European Application Serial No. 10777154.5, Response filed Feb. 21, 2018 to Communication Pursuant to Article 94(3) EPC dated Oct. 12, 2017", 12 pgs.
"European Application Serial No. 10777154.5, Response filed Sep. 8, 2016 to Office Action dated May 2, 2016", 69 pgs.
"Hemagglutinin [Influenza A virus (A/swine/France/WVL13/1995(H1N1))]", GenBank Accession# AC025026, (May 22, 2009), 1 pg.
"Hemagglutinin [Influenza B virus (B/Hong Kong/330/2001)]", GenBank ABL77178.1, (2006), 1 pg.
"International Application Serial No. PCT/US2010/054128, Preliminary Report on Patentability dated May 10, 2012", 10 pgs.
"International Application Serial No. PCT/US2010/054128, Search Report dated Feb. 23, 2011", 6 pgs.
"International Application Serial No. PCT/US2010/054128, Written Opinion dated Feb. 23, 2011", 8 pgs.
"Japanese Application Serial No. 2012-536963, Amendment and Argument filed Jun. 26, 2015 to Office Action dated Jan. 6, 2015", (w/ English Translation of Amended Claims), 12 pgs.
"Japanese Application Serial No. 2012-536963, Examiners Decision of Final Refusal dated Nov. 17, 2015", (Wi English Translation), 8 pgs.
"Japanese Application Serial No. 2012-536963, Office Action dated Jan. 6, 2015", (w/ English Translation), 14 pgs.
"Japanese Application Serial No. 2012-536963, Voluntary Amendment filed Jun. 27, 2012", (w/ English Translation of Amended Claims), 17 pgs.
"Japanese Application Serial No. 2016-053990, Office Action dated Jun. 6, 2017", (wl English Translation), 4 pgs.
"Japanese Application Serial No. 2016-053990, Response filed Dec. 6, 2017 to Office Action dated Jun. 6, 2017", (w/ English Translation of Amended Claims), 14 pgs.
"Neuraminidase, partial [Influenza A virus (A/swine/France/WVL13/1995(H1N1))]", GenBank Accession# AC025028, (May 22, 2009), 2 pgs.
"Nonstructural protein 1 [influenza B virus (B/Hong Kong/330/2001)]", GenBank AAT69443.1, (2006), 1 pg.
"Polymerase acidic [influenza A virus (A/swine/Shizuoka/120/97(H3N2))]", GenBank AAO15329.1, (2003), 1 pg.
"Polymerase PA [Influenza B virus (B/Hong Kong/330/2001)]", GenBank ABL7718 6 .1, (2006), 1 pg.
"Polymerase PB1 [Influenza B virus (B/Hong Kong/330/2001)]", GenBank ABL77187, (2006), 1 pg.
"Polymerase PB2 [Influenza B virus (B/Hong Kong/330/2001)] GenBank ABL77188.1", (2006), 1 pg.
Chan, Winnie, et al., "The cold adapted and temperature sensitive influenza A/Ann Arbor/6/60 virus, the master donor virus for live attenuated influenza vaccines, has multiple defects in replication at the restrictive temperature", Virology, 380(2), (2008), 304-311.
Dunham, Eleca J., et al., "Different Evolutionary Trajectories of European Avian-Like and Classical Swine H1N1 Influenza A Viruses", Journal of Virology, 83(11), (Jun. 2009), 5485-5494.
Fodor, E., et al., "Rescue of Influenza A Virus from Recombinant DNA", Journal of Virology, 73(11), XP002151487; ISSN:0022-538X, (Nov. 1999), 9679-9682.
Hickman, Danielle, et al., "An avian live attenuated master backbone for potential use in epidemic and pandemic influenza vaccines", Journal of General Virology, 89(Part 11), (2008), 2682-2690.
Hoffman, Lucas R, et al., "Structure-Based Identification of an Inducer of the Low-pH Conformational Change in the Influenza Virus Hemagglutinin: Irreversible Inhibition of Infectivity", Journal of Virology , vol. 71, No. 11, (Nov. 1997), 8808-8820.

(56) References Cited

OTHER PUBLICATIONS

Horimoto, "Designing Vaccines for Pandemic Influenza", Current Topics Microbial Immunol 333, (2009), 165-176.
Jang, S.-W., et al., "Deoxygedunin, a Natural Product with Potent Neurotrophic Activity in Mice", PLoS One 5(7): e11528, (2010), 1-15.
Kiseleva, Irina V, et al., "PB2 and PA genes control the expression of the temperature-sensitive phenotype of cold-adapted B/USSR/60/69 influenza master donor virus", Journal of General Virology, 91(4), (2010), 931-937.
Kistner, Otfried, et al., "Cell culture (Vero) derived whole virus (H5N1) vaccine based on wild-type virus strain induces cross-protective immune responses", Vaccine, 25(32), (2007), 6028-6036.
Kovacova, A., et al., "Sequence similarities and evolutionary relationships of influenza virus A hemagglutinins.", Virus Genes, 24(1), 2002), 57-63.
Kovacova, Andrea, et al., "Sequence Similarities and Evolutionary Relationships of Influenza Vrus A Hemagglutinins", Virus Genes, 24(1), (2002), 57-63.
Lee, Jong-Soo, et al., "The Highly Conserved HA2 Protein of the Influenza A Virus Induces a Cross Protective Immune Response", Journal of Virological Methods, 194(1-2), (2013), 280-288.
Lee, M. S, et al, "Genetic and pathogenic characterization of H6NI avian influenza viruses isolated in Taiwan between 1972 and 2005", Avian Diseases, 50(4), (Dec. 2006), 561-571.
Li, et al., "Genesis of a highly pathogenic and potentially pandemic H5N1 influenza virus in eastern Asia", (2004), 209-213 pgs.
Li, K. S, et al., "Genesis of a highly pathogenic and potentially pandemic H5NI influenza virus in eastern Asia", Nature, 430(6996), (Jul. 8, 2004), 209-213.
Lin, Y P, et al., "Adaptation of egg-grown and transfectant influenza viruses for growth in mammalian cells: selection of hemagglutinin mutants with elevated pH of membrane fusion", Virology, vol. 233, No. 2, (1997), 402-410.
Lugovtsev, V. Y., et al., "Genetic Composition and Mutational Pattern of Influenza B Viruses Adapted to Replication in Embryonated Eggs", GenBank: AAT69446.1, (2005), 1 pg.
Murakami, "Enhanced Growth of Influenza Vaccine Seed Viruses in Vero Cells Mediated by Broadening the Optimal pH Range for Virus Membrane Fusion", J Virol 86(3), (2012), 1405-1410.
Murakami, Shin, et al., "Growth Determinants for H5N1 Influenza Vaccine Seed Viruses in MDCK Cells", Journal of Virology, vol. 82, No. 21, (Nov. 2008), 10502-10509.
Neumann, G., et al., "An Improved Reverse Genetics System for Influenza A Virus Generation and Its Implications for Vaccine Production", Proc. Natl. Acad. Sci. USA, 102(46), (2005), 16825-16829.
Neumann, G., et al., "Emergence and pandemic potential of swine-origin HIN1 influenza virus", Nature (LONDON), 459(7249), (Jun. 2009), 931-939.
Neumann, G., et al., "Reverse Genetics of Influenza Viruses—Applications in Research and Vaccine Design", Monographs in Virology, 27, (2008), 118-133.
Ozaki, "Generation of High-Yielding Influenza A Viruses in African Green Monkey Kidney (Vero) Cells by Reverse Genetics", J Virol 78(4), (2004), 1851-1857.
Reed, M. L, et al., "Amino Acid Residues in the Fusion peptide Pocket Regulate the pH of Activation of the H5N1 Influenza Virus Hemagglutinin Protein", . J. Virol., 83(8), (2009), 3568-3580.
Romanova, J., et al., "Live cold-adapted influenza A vaccine produced in Vero cell line", Virus Research, 103, (2004), 187-193.
Xu, X., et al., "Reassortment and evolution of current human influenza A and B viruses", Virus Research, 103, (2004), 55-60.
Yi, Pu Lin, et al., "Adaptation of Egg-Grown and Transfectant Influenza Viruses for Growth in Mammalian Cells: Selection of Hemagglutinin Mutants with Elevated pH of Membrane Fusion", Virology, 233(2), (Jul. 7, 1997), 402-410.
U.S. Appl. No. 12/912,411, now U.S. Pat. No. 9,109,013, filed Oct. 26, 2010, High Titer Recombinant Influenza Viruses With Enhanced Replication in Vero Cells.
U.S. Appl. No. 14/816,807, now U.S. Pat. No. 10,059,925, filed Aug. 3, 2015, High Titer Recombinant Influenza Viruses With Enhanced Replication in Vero Cells.
U.S. Appl. No. 14/745,236, now U.S. Pat. No. 10,053,671, filed Jun. 19, 2015, Mutations That Confer Genetic Stability to Additional Genes in Influenza Viruses.
U.S. Appl. No. 15/966,092, filed Apr. 30, 2018, Mutations That Confer Genetic Stability to Additional Genes in Influenza Viruses.
"", Result 17, NCBI Blast nucleotide search of SEQ ID No. 2, database "nr", (Jul. 18, 2006), 3 pgs.
"", Result 1, NCBI Blast nucleotide search of SEQ ID No. 3, database "nr"; Result 4, NCBI Blast nucleotide search of SEQ ID No. 4, database "nr", (Jul. 22, 2006), 11 pgs.
"", Result 2, NCBI Blast nucleotide search of SEQ ID No. 5, database "nr"; Result 4, NCBI Blast nucleotide search of SEQ ID No. 6, database "nr", (Jul. 22, 2006), 6 pgs.
"", Results 1, NCBI Blast nucleotide search of SEQ ID No. 7, database "nr"; Result 1, NCBI Blast nucleotide search of SEQ ID No. 8, database "nr", (Jul. 23, 2006), 8 pgs.
"", Result 7, NCBI Blast nucleotide search of SEQ ID: 1, database "nr", (Jul. 18, 2006), 3 pgs.
"", FLUMISTTM Package Insert Template, [Online]. Retrieved from the Internet: http://www.fda.gov/downloads/BiologicsBioodVaccines!Vaccines/ApprovedProducts/UCM294307.pdf, (Mar. 1, 2012), 26 pgs.
"1.A.32 The Type B Influenza Virus NB Channel (NB-C) Family", Transport Protein Database, (University of California, San Diego, The Sailer Laboratory Bioinformatics Group) [online}. http://www.web.archive.org/web/200301311055254/http://tcdb.ucsd.edu/tcdb/tcfamilybrowse.php?tcname=1.A.32, (Archived Jan. 31, 2003), 1 pg.
"U.S. Appl. No. 09/834,095, Advisory Action dated Jan. 8, 2004", 3 pgs.
"U.S. Appl. No. 09/834,095, Final Office Action dated Aug. 26, 2003", 12 pgs.
"U.S. Appl. No. 09/834,095, Non-Final Office Action dated Nov. 4, 2002", 12 pgs.
"U.S. Appl. No. 09/834,095, Notice of Allowance dated Sep. 27, 2004", 13 pgs.
"U.S. Appl. No. 09/834,095, Office Action dated Apr. 20, 2004", 11 pgs.
"U.S. Appl. No. 09/834,095, Response filed Feb. 4, 2003 to Office Action dated Nov. 4, 2002", 14 pgs.
"U.S. Appl. No. 09/834,095, Response filed Jun. 12, 2003 to Restriction Requirement dated Apr. 22, 2003", 2 pgs.
"U.S. Appl. No. 09/834,095, Response filed Jun. 18, 2004 to Office Action dated Apr. 20, 2004", 11 pgs.
"U.S. Appl. No. 09/834,095, Response filed Aug. 1, 2002 to Restriction Requirement dated Jul. 1, 2002", 3 pgs.
"U.S. Appl. No. 09/834,095, Response filed Nov. 26, 2003 to Final Office Action dated Aug. 26, 2003", 10 pgs.
"U.S. Appl. No. 09/834,095, Restriction Requirement dated Apr. 22, 2003", 5 pgs.
"U.S. Appl. No. 09/834,095, Restriction Requirement dated Jul. 1, 2002", 9 pgs.
"U.S. Appl. No. 09/834,095, Supplemental Amendment filed Aug. 4, 2004", 7 pgs.
"U.S. Appl. No. 10/827,995, Final Office Action dated Nov. 15, 2006", 10 pgs.
"U.S. Appl. No. 10/827,995, Non-Final Office Action dated Jun. 2, 2006", 15 pgs.
"U.S. Appl. No. 10/827,995, Non-Final Office Action dated Oct. 25, 2007", 7 pgs.
"U.S. Appl. No. 10/827,995, Notice of Allowance dated Feb. 17, 2009", 9 pgs.
"U.S. Appl. No. 10/827,995, Notice of Allowance dated Jul. 2, 2008", 9 pgs.
"U.S. Appl. No. 10/827,995, Notice of Allowance dated Oct. 17, 2008", 7 pgs.
"U.S. Appl. No. 10/827,995, Notice of Non-Compliant Amendment dated Jul. 25, 2007", 4 pgs.
"U.S. Appl. No. 10/827,995, Proposed Examiner's Amendment dated Jun. 5, 2008", 6 pgs.

(56) References Cited

OTHER PUBLICATIONS

"U.S. Appl. No. 10/827,995, Response filed Mar. 3, 2008 to Office Action dated Oct. 25, 2007", 10 pgs.
"U.S. Appl. No. 10/827,995, Response filed May 14, 2007 Final Office Action dated Nov. 15, 2006", 16 pgs.
"U.S. Appl. No. 10/827,995, Response filed Aug. 13, 2007 to Notice of Non-Compliant Amendment dated Jul. 25, 2007", 16 pgs.
"U.S. Appl. No. 10/827,995, Response filed Aug. 17, 2006 Non-Final Office Action dated Jun. 2, 2006", 15 pgs.
"U.S. Appl. No. 10/855,875 , Response filed May 17, 2012 to Non Final Office Action dated Mar. 15, 2012", 15 pgs.
"U.S. Appl. No. 10/855,875, Final Office Action dated Mar. 11, 2008", FOAR, 20 Pgs.
"U.S. Appl. No. 10/855,875, Final Office Action dated Dec. 10, 2010", 15 pgs.
"U.S. Appl. No. 10/855,875, Final Office Action dated Aug. 2, 2006", 34 pgs.
"U.S. Appl. No. 10/855,875, Non Final Office Action dated Mar. 15, 2012", 15 pgs.
"U.S. Appl. No. 10/855,875, Non-Final Office Action dated Feb. 19, 2010", 7 pgs.
"U.S. Appl. No. 10/855,875, Non-Final Office Action dated Aug. 7, 2009", 32 pgs.
"U.S. Appl. No. 10/855,875, Non-Final Office Action dated Nov. 6, 2008", 12 pgs.
"U.S. Appl. No. 10/855,875, Non-Final Office Action dated Nov. 30, 2005", 13 pgs.
"U.S. Appl. No. 10/855,875, Non-Final Office Action dated May 3, 2007", 13 pgs.
"U.S. Appl. No. 10/855,875, Notice of Allowance dated Mar. 4, 2013", 8 pgs.
"U.S. Appl. No. 10/855,875, Preliminary Amendment filed Feb. 2, 2007", 14 pgs.
"U.S. Appl. No. 10/855,875, Response filed Jan. 29, 2007 to Final Office Action dated Aug. 2, 2007", 14 pgs.
"U.S. Appl. No. 10/855,875, Response filed Mar. 18, 2011 to Final Office Action dated Dec. 10, 2010", 15 pgs.
"U.S. Appl. No. 10/855,875, Response filed Aug. 17, 2010 to Non Final Office Action dated Feb. 19, 2010", 20 pgs.
"U.S. Appl. No. 10/855,875, Response filed Dec. 7, 2009 to Non Final Office Action dated Aug. 7, 2009", 15 pgs.
"U.S. Appl. No. 10/855,875, Response filed Mar. 31, 2009 to Non Final Office Action dated Nov. 6, 2008", 14 pgs.
"U.S. Appl. No. 10/855,875, Response filed May 1, 2006 Non-Final Office Action dated Nov. 30, 2005", 13 pgs.
"U.S. Appl. No. 10/855,875, Response filed Aug. 18, 2008 to final Office Action dated Mar. 11, 2008", 15 pgs.
"U.S. Appl. No. 10/855,875, Response filed Sep. 20, 2005 to Restriction Requirement dated Jul. 26, 2005", 4 pgs.
"U.S. Appl. No. 10/855,875, Restriction Requirement dated Dec. 23, 2011", 9 pgs.
"U.S. Appl. No. 10/855,875, Restriction Requirement dated Jul. 26, 2005", 9 pgs.
"U.S. Appl. No. 10/855,875, Response filed Nov. 2, 2007 to Office Action dated May 3, 2007", 16 pgs.
"U.S. Appl. No. 11/043,768 Non-Final Office Action dated Sep. 27, 2010", 8 pgs.
"U.S. Appl. No. 11/043,768, Final Office Action dated Jun. 27, 2008", 8 pgs.
"U.S. Appl. No. 11/043,768, Non-Final Office Action dated Feb. 23, 2010", 6 pgs.
"U.S. Appl. No. 11/043,768, Non-Final Office Action dated Feb. 23, 2009", 7 pgs.
"U.S. Appl. No. 11/043,768, Non-Final Office Action dated Nov. 28, 2007", 9 pgs.
"U.S. Appl. No. 11/043,768, Notice of Allowance dated Jun. 29, 2011", 12 pgs.
"U.S. Appl. No. 11/043,768, Response filed May 2, 2011 to Final Office Action dated Feb. 3, 2011", 11 pgs.
"U.S. Appl. No. 11/043,768, Response filed Jun. 15, 2010 to Non Final Office Action dated Feb. 23, 2010", 9 pgs.
"U.S. Appl. No. 11/043,768, Response filed Jun. 23, 2009 to Non Final Office Action dated Feb. 23, 2009", 9 pgs.
"U.S. Appl. No. 11/043,768, Response filed Sep. 13, 2007 to Restriction Requirement dated Mar. 13, 2007", 10 pgs.
"U.S. Appl. No. 11/043,768, Response filed Oct. 26, 2010 to Non Final Office Action dated Sep. 27, 2010", 11 pgs.
"U.S. Appl. No. 11/043,768, Response filed Dec. 12, 2008 to Final Office Action dated Jun. 27, 2008", 9 pgs.
"U.S. Appl. No. 11/043,768, Response filed Mar. 10, 2008 to Office Action dated Nov. 28, 2007", 12 pgs.
"U.S. Appl. No. 11/043,768, Restriction Requirement dated Mar. 13, 2007", 9 pgs.
"U.S. Appl. No. 11/043,786, Final Office Action dated Feb. 3, 2011", 10 pgs.
"U.S. Appl. No. 11/729,557, Advisory Action dated May 9, 2011", 3 pgs.
"U.S. Appl. No. 11/729,557, Advisory Action dated Dec. 24, 2014", 3 pgs.
"U.S. Appl. No. 11/729,557, Final Office Action dated Feb. 2, 2011", 14 pgs.
"U.S. Appl. No. 11/729,557, Final Office Action dated Aug. 20, 2009", 13 Pgs.
"U.S. Appl. No. 11/729,557, Final Office Action dated Sep. 12, 2014", 14 pgs.
"U.S. Appl. No. 11/729,557, Non Final Office Action dated Feb. 18, 2015", 13 pgs.
"U.S. Appl. No. 11/729,557, Non Final Office Action dated Feb. 26, 2014", 16 pgs.
"U.S. Appl. No. 11/729,557, Non-Final Office Action dated Jan. 30, 2009", 20 pgs.
"U.S. Appl. No. 11/729,557, Non-Final Office Action dated Feb. 22, 2010", 16 pgs.
"U.S. Appl. No. 11/729,557, Non-Final Office Action dated Aug. 23, 2010", 15 pgs.
"U.S. Appl. No. 11/729,557, Notice of Allowance dated Sep. 30, 2015", 11 pgs.
"U.S. Appl. No. 11/729,557, Respons filed Jun. 22, 2010 to Non Final Office Action dated Feb. 22, 2010", 33 pgs.
"U.S. Appl. No. 11/729,557, Response filed Apr. 27, 2011 to Final Office Action dated Feb. 2, 2011", 14 pgs.
"U.S. Appl. No. 11/729,557, Response filed Apr. 30, 2009 to Non Final Office Action dated Jan. 30, 2009", 18 pgs.
"U.S. Appl. No. 11/729,557, Response filed May 22, 2014 to Non Final Office Action dated Feb. 26, 2014", 13 pgs.
"U.S. Appl. No. 11/729,557, Response filed May 28, 2008 to Restriction Requirement dated Nov. 28, 2007", 13 pgs.
"U.S. Appl. No. 11/729,557, Response filed Jun. 22, 2010 to Non Final Office Action dated Feb. 22, 2010", 16 pgs.
"U.S. Appl. No. 11/729,557, Response filed Jun. 22, 2015 to non Final Office Action dated Feb. 18, 2015", 13 pgs.
"U.S. Appl. No. 11/729,557, Response filed Oct. 28, 2010 to Non Final Office Action dated Aug. 23, 2010", 13 pgs.
"U.S. Appl. No. 11/729,557, Response filed Dec. 1, 2009 to Final Office Action dated Aug. 26, 2009", 16 pgs.
"U.S. Appl. No. 11/729,557, Response filed Dec. 11, 2014 to Final Office Action dated Sep. 12, 2014", 15 pgs.
"U.S. Appl. No. 11/729,557, Restriction Requirement dated Nov. 28, 2007", 9 pgs.
"U.S. Appl. No. 12/214,414, Advisory Action dated Feb. 2, 2016", 5 pgs.
"U.S. Appl. No. 12/214,414, Advisory Action dated Apr. 15, 2015", 6 pgs.
"U.S. Appl. No. 12/214,414, Advisory Action dated Oct. 21, 2011", 5 pgs.
"U.S. Appl. No. 12/214,414, Examiner Interview Summary dated Dec. 11, 2015", 3 pgs.
"U.S. Appl. No. 12/214,414, Final Office Action dated Jan. 20, 2015", 28 pgs.
"U.S. Appl. No. 12/214,414, Final Office Action dated Aug. 2, 2011", 7 pgs.

(56) References Cited

OTHER PUBLICATIONS

"U.S. Appl. No. 12/214,414, Final Office Action dated Nov. 18, 2015", 17 pgs.
"U.S. Appl. No. 12/214,414, Non Final Office Action dated Jun. 12, 2014", 28 pgs.
"U.S. Appl. No. 12/214,414, Non Final Office Action dated Dec. 10, 2010", 6 pgs.
"U.S. Appl. No. 12/214,414, Non-Final Office Action dated Mar. 2, 2010", 9 pgs.
"U.S. Appl. No. 12/214,414, Notice of Allowance dated Jun. 7, 2016", 18 pgs.
"U.S. Appl. No. 12/214,414, Response filed Jan. 19, 2016 to Final Office Action dated Nov. 18, 2015", 14 pgs.
"U.S. Appl. No. 12/214,414, Response filed Feb. 18, 2016 to Final Office Action dated Nov. 18, 2015", 14 pgs.
"U.S. Appl. No. 12/214,414, Response filed Mar. 26, 2015 to Final Office Action dated Jan. 20, 2015", 13 pgs.
"U.S. Appl. No. 12/214,414, Response filed May 3, 2011 to Non Final Office Action dated Dec. 10, 2010", 12 pgs.
"U.S. Appl. No. 12/214,414, Response filed Jul. 20, 2015 to Advisory Action dated Apr. 15, 2015", 14 pgs.
"U.S. Appl. No. 12/214,414, Response filed Aug. 31, 2010 to Non Final Office Action dated Mar. 2, 2010", 11 pgs.
"U.S. Appl. No. 12/214,414, Response filed Oct. 3, 2011 to Non Final Office Action dated Aug. 2, 2011", 9 pgs.
"U.S. Appl. No. 12/214,414, Response filed Dec. 21, 2011 to Advisory Action dated Oct. 21, 2011", 10 pgs.
"U.S. Appl. No. 12/467,492, Restriction Requirement dated Nov. 22, 2010", 6 pgs.
"U.S. Appl. No. 13/070,110 Response filed Feb. 14, 2017 to Final Office Action dated Sep. 14, 2016", 8 pgs.
"U.S. Appl. No. 13/070,110, Advisory Action dated Mar. 3, 2017", 5 pgs.
"U.S. Appl. No. 13/070,110, Examiner Interview Summary dated Jan. 16, 2018", 3 pgs.
"U.S. Appl. No. 13/070,110, Final Office Action dated Apr. 3, 2015", 18 pgs.
"U.S. Appl. No. 13/070,110, Final Office Action dated Jun. 12, 2013", 7 pgs.
"U.S. Appl. No. 13/070,110, Final Office Action dated Sep. 14, 2016", 12 pgs.
"U.S. Appl. No. 13/070,110, Non Final Office Action dated Jul. 21, 2017", 14 pgs.
"U.S. Appl. No. 13/070,110, Non Final Office Action dated Oct. 2, 2014", 24 pgs.
"U.S. Appl. No. 13/070,110, Non Final Office Action dated Dec. 11, 2015", 19 pgs.
"U.S. Appl. No. 13/070,110, Non Final Office Action dated Dec. 21, 2012", 7 pgs.
"U.S. Appl. No. 13/070,110, Notice of Allowance dated Mar. 26, 2018", 6 pgs.
"U.S. Appl. No. 13/070,110, Preliminary Amendment filed Jun. 6, 2011", 4 pgs.
"U.S. Appl. No. 13/070,110, Response filed Jan. 22, 2018 to Non Final Office Action dated Jul. 21, 2017", 10 pgs.
"U.S. Appl. No. 13/070,110, Response filed Mar. 22, 2013 to Non Final Office Action dated Dec. 21, 2012", 8 pgs.
"U.S. Appl. No. 13/070,110, Response filed May 27, 2016 to Non Final Office Action dated Dec. 11, 2015", 13 pgs.
"U.S. Appl. No. 13/070,110, Response filed Jun. 20, 2017 to Advisory Action dated Mar. 3, 2017", 13 pgs.
"U.S. Appl. No. 13/070,110, Response filed Sep. 3, 2014 to Restriction Requirement dated Jul. 8, 2014", 7 pgs.
"U.S. Appl. No. 13/070,110, Response filed Oct. 2, 2015 to Final Office Action dated Apr. 3, 2015", 11 pgs.
"U.S. Appl. No. 13/070,110, Response filed Nov. 12, 2013 to Final Office Action dated Jun. 12, 2013", 9 pgs.
"U.S. Appl. No. 13/070,110, Response filed Dec. 30, 2014 to Non Final Office Action dated Oct. 2, 2014", 13 pgs.
"U.S. Appl. No. 13/070,110, Restriction Requirement dated Jul. 8, 2014", 7 pgs.
"U.S. Appl. No. 14/332,121, Non Final Office Action dated May 16, 2016", 9 pgs.
"U.S. Appl. No. 14/332,121, Notice of Allowance dated Feb. 15, 2017", 10 pgs.
"U.S. Appl. No. 14/332,121, Notice of Allowance dated Jun. 15, 2017", 8 pgs.
"U.S. Appl. No. 14/332,121, Notice of Allowance dated Oct. 11, 2017", 8 pgs.
"U.S. Appl. No. 14/332,121, Preliminary Amendment filed Sep. 30, 2014", 5 pgs.
"U.S. Appl. No. 14/332,121, Response filed Jan. 29, 2016 to Restriction Requirement dated Jul. 30, 2015", 9 pgs.
"U.S. Appl. No. 14/332,121, Response filed Sep. 7, 2017 to Notice of Allowability dated Jun. 15, 2017", 8 pgs.
"U.S. Appl. No. 14/332,121, Response filed Oct. 11, 2016 to Non Final Office Action dated May 16, 2016", 9 pgs.
"U.S. Appl. No. 14/332,121, Restriction Requirement dated Jul. 30, 2015", 9 pgs.
"U.S. Appl. No. 14/332,121, Supplemental Amendment filed Jan. 23, 2017", 10 pgs.
"U.S. Appl. No. 14/745,236, Restriction Requirement dated Sep. 23, 2016", 8 pgs.
"U.S. Appl. No. 15/000,851, Non Final Office Action dated Jan. 26, 2017", 15 pgs.
"U.S. Appl. No. 15/000,851, Notice of Allowance dated Nov. 8, 2017", 9 pgs.
"U.S. Appl. No. 15/000,851, Preliminary Amendment filed Feb. 3, 2016", 3 pgs.
"U.S. Appl. No. 15/000,851, Response filed Jul. 26, 2017 to Non Final Office Action dated Jan. 26, 2017", 16 pgs.
"U.S. Appl. No. 15/000,851, Response filed Oct. 12, 2016 to Restriction Requirement dated May 12, 2016", 11 pgs.
"U.S. Appl. No. 15/000,851, Restriction Requirement dated May 12, 2016", 6 pgs.
"U.S. Appl. No. 15/000,851, Supplemental Amendment filed Apr. 4, 2016", 10 pgs.
"U.S. Appl. No. 15/170,556, Preliminary Amendment filed Aug. 22, 2016", 9 pgs.
"U.S. Appl. No. 15/170,556, Response filed Apr. 5, 2018 to Restriction Requirement dated Feb. 16, 2018", 8 pgs.
"U.S. Appl. No. 15/170,556, Restriction Requirement dated Feb. 16, 2018", 7 pgs.
"U.S. Appl. No. 15/203,581, Examiners Interview Summary dated Sep. 11, 2017", 1 pg.
"U.S. Appl. No. 15/203,581, Notice of Allowance dated Sep. 11, 2017", 12 pgs.
"U.S. Appl. No. 15/203,581, Preliminary Amendment filed Sep. 22, 2016", 4 pgs.
"U.S. Appl. No. 15/203,581, PTO Response to Rule 312 Communication dated Dec. 27, 2017", 2 pgs.
"U.S. Appl. No. 15/203,581, Response filed Aug. 15, 2017 to Restriction Requirement dated Jun. 16, 2017", 8 pgs.
"U.S. Appl. No. 15/203,581, Restriction Requirement dated Jun. 16, 2017", 8 pgs.
"U.S. Appl. No. 15/292,595, Non Final Office Action dated Sep. 25, 2017", 13 pgs.
"U.S. Appl. No. 15/292,595, Notice of Allowance dated Feb. 28, 2018", 9 pgs.
"U.S. Appl. No. 15/292,595, Preliminary Amendment filed Dec. 27, 2016", 5 pgs.
"U.S. Appl. No. 15/292,595, Response filed Dec. 22, 2017 to Non Final Office Action dated Sep. 25, 2017", 9 pgs.
"U.S. Appl. No. 15/436,245, Preliminary Amendment filed May 5, 2017", 3 pgs.
"U.S. Appl. No. 15/593,039, Non Final Office Action dated Feb. 6, 2018", 8 pgs.
"U.S. Appl. No. 15/593,039, Notice of Allowance dated Jul. 11, 2018", 5 pgs.
"U.S. Appl. No. 15/593,039, Preliminary Amendment filed Jul. 25, 2017", 7 pgs.

(56) References Cited

OTHER PUBLICATIONS

"U.S. Appl. No. 15/593,039, Response filed Apr. 30, 2018 to Non Final Office Action dated Feb. 4, 2018", 8 pgs.
"U.S. Appl. No. 15/593,039, Response filed Dec. 18, 2017 to Restriction Requirement dated Oct. 18, 2017", 8 pgs.
"U.S. Appl. No. 15/593,039, Restriction Requirement dated Oct. 18, 2017", 6 pgs.
"U.S. Appl. No. 15/593,039, Supplemental Preliminary Amendment filed Jul. 26, 2017", 4 pgs.
"U.S. Appl. No. 15/865,364, Preliminary Amendment filed Apr. 10, 2018", 10 pgs.
"U.S. Appl. No. 12/214,414, Response filed Oct. 14, 2014 to Non Final Office Action dated Jun. 12, 2014", 16 pgs.
"Australian Application Serial No. 2001255336, Examiner's First Report dated Feb. 16, 2005", 2 pgs.
"Australian Application Serial No. 2001255336, Response filed Aug. 23, 2005 to Examiner's First Report dated Feb. 16, 2005", 10 pgs.
"Australian Application Serial No. 2004249133, First Examiner's Report dated May 5, 2008", 4 pgs.
"Australian Application Serial No. 2004249133, Response filed Mar. 30, 2009 to First Examiner's Report dated May 5, 2008", 30 pgs.
"Australian Application Serial No. 2007245192, Office Action dated Aug. 25, 2011", 2 pgs.
"Australian Application Serial No. 2007245192, Response filed Feb. 28, 2012 to Office Action dated Aug. 25, 2011", 22 pgs.
"Australian Application Serial No. 2012204138, First Examiner Report dated Jul. 16, 2013", 4 pgs.
"Australian Application Serial No. 2012204138, Response filed Dec. 24, 2013 to First Examiner Report dated Jul. 16, 2013", 21 pgs.
"Australian Application Serial No. 2014202470, First Examiner Report dated Jul. 20, 2015", 2 pgs.
"Australian Application Serial No. 2014202470, Respojnse filed Jul. 4, 2016 to Subsequent Examiners Report dated Feb. 1, 2016", 3 pgs.
"Australian Application Serial No. 2014202470, Response filed Jul. 20, 2016 to Subsequent Examiners Report dated Jul. 19, 2016", 15 pgs.
"Australian Application Serial No. 2014202470, Response filed Dec. 1, 2015 to First Examiner Report dated Jul. 20, 2015", 22 pgs.
"Australian Application Serial No. 2014202470, Subsequent Examiners Report dated Feb. 1, 2016", 2 pgs.
"Australian Application Serial No. 2014202470, Subsequent Examiners Report dated Jul. 19, 2016", 3 pgs.
"Brazilian Application Serial No. PI0410702-0, Office Action dated Feb. 23, 2012", (w/ English Translation), 4 pgs.
"Brazilian Application Serial No. PI0410702-0, Response filed May 7, 2012 to Office Action dated Feb. 23, 2012", (w/ English Translation of Claims), 11 pgs.
"Canadian Application Serial No. 2,406,180, Office Action dated Sep. 9, 2008", 5 pgs.
"Canadian Application Serial No. 2,406,180, Office Action dated Nov. 10, 2011", 3 pgs.
"Canadian Application Serial No. 2,406,180, Office action dated Nov. 23, 2009", 3 pgs.
"Canadian Application Serial No. 2,406,180, Office Action dated Dec. 10, 2010", 2 Pgs.
"Canadian Application Serial No. 2,406,180, Response filed Jan. 26, 2009 to Official Action dated Sep. 9, 2008", 22 pgs.
"Canadian Application Serial No. 2,406,180, Response filed May 21, 2010 to Office action dated Nov. 23, 2009", 13 pgs.
"Canadian Application Serial No. 2,406,180, Response filed Jun. 14, 2011 to Office Action dated Dec. 10, 2010", 10 pgs.
"Canadian Application Serial No. 2,522,081, Amendment After Allowance filed Aug. 10, 2012", 3 pgs.
"Canadian Application Serial No. 2,522,081, Office Action filed Nov. 18, 2011", 11 pgs.
"Canadian Application Serial No. 2,522,081, Office Action dated Jun. 6, 2011", 2 pgs.
"Canadian Application Serial No. 2,522,081, Office Action dated Aug. 30, 2010", 2 pgs.
"Canadian Application Serial No. 2,522,081, Office Action dated Oct. 8, 2009", 6 pgs.
"Canadian Application Serial No. 2,522,081, Response filed Feb. 28, 2011 to Office Action dated Aug. 30, 2010", 10 pgs.
"Canadian Application Serial No. 2,522,081, Response filed Apr. 8, 2010 to Office Action dated Oct. 8, 2009", 30 pgs.
"Canadian Application Serial No. 2,522,081, Response filed Nov. 18, 2011 to Office Action dated Jun. 6, 2011", 11 pgs.
"Canadian Application Serial No. 2,525,953, Amendment and Response filed Feb. 1, 2017 to Office Action dated Aug. 1, 2016", 28 pgs.
"Canadian Application Serial No. 2,525,953, Office Action dated Jan. 21, 2016", 6 pgs.
"Canadian Application Serial No. 2,525,953, Office Action dated Jul. 31, 2012", 4 pgs.
"Canadian Application Serial No. 2,525,953, Office Action dated Aug. 1, 2016", 6 pgs.
"Canadian Application Serial No. 2,525,953, Office Action dated Aug. 16, 2013", 3 pgs.
"Canadian Application Serial No. 2,525,953, Office Action dated Oct. 3, 2017", 4 pgs.
"Canadian Application Serial No. 2,525,953, Office Action dated Nov. 6, 2014", 3 pgs.
"Canadian Application Serial No. 2,525,953, Office Action dated Jun. 22, 2011", 4 pgs.
"Canadian Application Serial No. 2,525,953, Office Action received Jun. 22, 2011", 4 pgs.
"Canadian Application Serial No. 2,525,953, Response filed Jan. 31, 2013 to Office Action dated Jul. 31, 2012", 11 pgs.
"Canadian Application Serial No. 2,525,953, Response filed Feb. 1, 2017 to Office Action dated Aug. 1, 2016", 28 pgs.
"Canadian Application Serial No. 2,525,953, Response filed Feb. 14, 2014 to Office Action dated Aug. 16, 2013", 16 pgs.
"Canadian Application Serial No. 2,525,953, Response filed Apr. 3, 2018 to Office Action dated Oct. 3, 2017", 46 pgs.
"Canadian Application Serial No. 2,525,953, Response filed May 1, 2015 to Office Action dated Nov. 6, 2014", 23 pgs.
"Canadian Application Serial No. 2,525,953, Response filed Jul. 11, 2016 to Office Action dated Jan. 21, 2016", 21 pgs.
"Canadian Application Serial No. 2,525,953, Response filed Dec. 22, 2011 to Office Action dated Jun. 22, 2011", 17 pgs.
"Canadian Application Serial No. 2,647,985 , Office Action dated May 15, 2013", 3 pgs.
"Canadian Application Serial No. 2,647,985 , Response filed Sep. 30, 2013 to Office Action dated May 15, 2013", 20 pgs.
"Canadian Application Serial No. 2406180, Response filed May 7, 2012 to Office Action dated Nov. 10, 2011", 11 pgs.
"Chinese Application Serial No. 200480017037, First Office Action dated May 25, 2007", (w/ English Translation), 10 pgs.
"Chinese Application Serial No. 200480017037, Response filed Oct. 30, 2007 to First Office Action dated May 25, 2007", (w/ English Translation of Claims), 26 pgs.
"Chinese Application Serial No. 200480017037.X, Response filed May 14, 2010 to Third Office Action dated Mar. 1, 2010", (w/ English Translation of Claims), 16 pgs.
"Chinese Application Serial No. 200480017037.X, Response filed Aug. 4, 2009 to Second Office Action dated Mar. 20, 2009", (w/ English Translation of Amended Claims), 15 pgs.
"Chinese Application Serial No. 200480017037.X, Second Office Action dated Mar. 20, 2009", (English Translation), 7 pgs.
"Chinese Application Serial No. 200480017037.X, Third Office Action dated Mar. 1, 2010", (w/ English Translation), 9 pgs.
"Chinese Application Serial No. 200480021259.9 Office Action Sep. 11, 2009", (English Translation), 7 pgs.
"Chinese Application Serial No. 200480021259.9 Response filed Aug. 20, 2010 to Office Acton dated May 6, 2010", (w/ English Translation of Claims), 26 pgs.
"Chinese Application Serial No. 200480021259.9, First Offiice Action dated Aug. 24, 2007", (w/ English Translation), 9 pgs.
"Chinese Application Serial No. 200480021259.9, Notice of Reexamination dated Jul. 3, 2012", (w/ English Translation), 10 pgs.

(56) References Cited

OTHER PUBLICATIONS

"Chinese Application Serial No. 200480021259.9, Office Action dated Jan. 11, 2011", (w/ English Translation), 15 pgs.
"Chinese Application Serial No. 200480021259.9, Office Action dated May 6, 2010", (w/ English Translation), 12 pgs.
"Chinese Application Serial No. 200480021259.9, Office Action dated Jul. 3, 2012", (w/ English Translation), 10 pgs.
"Chinese Application Serial No. 200480021259.9, Request for Reexamination filed Apr. 26, 2011", (w/ English Translation of Amended Claims), 23 pgs.
"Chinese Application Serial No. 200480021259.9, Response filed Mar. 7, 2008 to Offiice Action dated Aug. 24, 2007", (w/ English Translation of Claims), 13 pgs.
"Chinese Application Serial No. 200480021259.9, Response filed Oct. 16, 2012 to Office Action dated Jul. 3, 2012", (w/ English Translation of Claims), 13 pgs.
"Chinese Application Serial No. 200780020095.1, Decision on Rejection dated Jul. 22, 2013", (w/ English Translation), 11 pgs.
"Chinese Application Serial No. 200780020095.1, First Office Action dated Jun. 24, 2011", (w/ English Translation), 13 pgs.
"Chinese Application Serial No. 200780020095.1, Office Action dated Jan. 29, 2013", (w/ English Translation), 10 pgs.
"Chinese Application Serial No. 200780020095.1, Office Action dated Mar. 5, 2015", (w/ English Translation), 12 pgs.
"Chinese Application Serial No. 200780020095.1, Office Action dated Apr. 26, 2016", (w/ English Summary), 4 pgs.
"Chinese Application Serial No. 200780020095.1, Office Action dated May 3, 2012", (w/ English Translation), 10 pgs.
"Chinese Application Serial No. 200780020095.1, Office Action dated Nov. 2, 2016", (w/ English Translation), 11 pgs.
"Chinese Application Serial No. 200780020095.1, Response filed Jan. 6, 2017 to Office Action dated Nov. 2, 2016", (w/ English Translation of Claims), 15 pgs.
"Chinese Application Serial No. 200780020095.1, Response filed Jun. 9, 2013 to Office Action dated Jan. 29, 2013", (w/ English Translation of Claims), 10 pgs.
"Chinese Application Serial No. 200780020095.1, Response filed Jun. 23, 2015 to Office Action dated Mar. 5, 2015", (w/ English Translation of Claims), 16 pgs.
"Chinese Application Serial No. 200780020095.1, Response filed Jun. 30, 2016 to Office Action dated Apr. 26, 2016", (w/ English Translation of Claims), 22 pgs.
"Chinese Application Serial No. 200780020095.1, Response filed Sep. 17, 2012 to Office Action dated May 3, 2012", (w/ English Translation of Claims), 17 pgs.
"Chinese Application Serial No. 200780020095.1, Response filed Nov. 5, 2013 to to Decision on Rejection dated Jul. 22, 2013", (w/ English Translation of Claims), 12 pgs.
"Chinese Application Serial No. 200780020095.1, Response filed Nov. 8, 2011 to Office Action dated Jun. 24, 2011", (w/ English Translation of Amended Claims), 20 pgs.
"Chinese Application Serial No. 200480021259.9, Office Action dated May 8, 2009", (w/ English Translation), 6 pgs.
"Eurasian Application No. 200501890, Notice of Allowance dated Jun. 23, 2009", 1 pg.
"Eurasian Application Serial No. 200501890, Office Action dated Mar. 23, 2007", (w English Translation), 2 pgs.
"Eurasian Application Serial No. 200501890, Office Action dated Sep. 4, 2008", (English Translation), 1 pg.
"Eurasian Application Serial No. 200501890, Office Action dated Dec. 17, 2007", (w/ English Translation), 6 pgs.
"Eurasian Application Serial No. 200501890, Response filed Mar. 26, 2008 to Office Action dated Dec. 17, 2007", (w/ English Translation of Claims), 15 pgs.
"Eurasian Application Serial No. 200501890, Response filed Jun. 14, 2007 to Office Action dated Mar. 23, 2007", (w/ English Translation of Claims), 11 pgs.
"Eurasian Application Serial No. 200501890, Response filed Dec. 17, 2008 to Office Action", (w/ English Translation of Claims), 13 pgs.
"Eurasian Application Serial No. 200501890, Response filed Dec. 17, 2008 to Office Action dated Sep. 4, 2008", (w/ English Translation of Claims), 14 pgs.
"European Application 04750333.9, Communication dated Oct. 12, 2006", 6 pgs.
"European Application 04750333.9, Communication dated Dec. 8, 2006", 4 pgs.
"European Application 04750333.9, Communication dated Apr. 11, 2008", 6 pgs.
"European Application 04750333.9, Response filed Oct. 4, 2007 to Communication dated Dec. 8, 2006", 42 pgs.
"European Application 04750333.9, Response filed Nov. 21, 2006 to Communication dated Oct. 12, 2006", 4 pgs.
"European Application Serial No. 01928486.8 Office Action dated Oct. 1, 2009", 2 pgs.
"European Application Serial No. 01928486.8, Communication dated Aug. 10, 2007", 3 pgs.
"European Application Serial No. 01928486.8, Communication dated Sep. 20, 2005", 4 pgs.
"European Application Serial No. 01928486.8, Office Action dated Feb. 19, 2009", 3 pgs.
"European Application Serial No. 01928486.8, Response filed Jan. 30, 2006 to Communication dated Sep. 20, 2005", 9 pgs.
"European Application Serial No. 01928486.8, Response filed Aug. 28, 2009 to Communication dated Feb. 19, 2009", 5 pgs.
"European Application Serial No. 01928486.8, Response filed Jan. 21, 2008 to Communication dated Aug. 10, 2007", 11 pgs.
"European Application Serial No. 01928486.8, Response filed Dec. 9, 2009 to Office Action dated Oct. 1, 2009", 11 pgs.
"European Application Serial No. 04750333.9, Office Action dated Jan. 22, 2009", 5 pgs.
"European Application Serial No. 04750333.9, Response filed Oct. 21, 2008 to Communication dated Apr. 11, 2008", 15 pgs.
"European Application Serial No. 04750333.9, Response filed Nov. 17, 2009 to Communication dated Jan. 22, 2009", 17 pgs.
"European Application Serial No. 04750333.9, Summons To Attend Oral Proceedings mailed Aug. 3, 2011", 13 pgs.
"European Application Serial No. 04776133.3, Communication dated Mar. 30, 2006", 3 pgs.
"European Application Serial No. 04776133.3, Examination Notification Art. 94(3) dated Jul. 28, 2015", 4 pgs.
"European Application Serial No. 04776133.3, Examination Notification Art. 94(3) dated Nov. 25, 2013", 5 pgs.
"European Application Serial No. 04776133.3, Office Action dated Jan. 5, 2010", 4 pgs.
"European Application Serial No. 04776133.3, Response filed Jan. 25, 2007 to Communication dated Mar. 30, 2006", 20 pgs.
"European Application Serial No. 04776133.3, Response filed Apr. 30, 2014 to Examination Notification Art. 94(3) dated Nov. 25, 2013", 12 pgs.
"European Application Serial No. 04776133.3, Response filed Jul. 15, 2010 to Office Action dated Jan. 5, 2010", 9 pgs.
"European Application Serial No. 04776133.3, Response filed Sep. 18, 2015 to Examination Notification Art. 94(3) dated Jul. 28, 2015", 47 pgs.
"European Application Serial No. 07754132.4, Office Action dated Apr. 28, 2009", 4 pgs.
"European Application Serial No. 07754132.4, Office Action dated Sep. 5, 2011", 5 pgs.
"European Application Serial No. 07754132.4, Office Action dated Nov. 2, 2012", 4 pgs.
"European Application Serial No. 07754132.4, Response filed Feb. 5, 2010 to Office Action dated Apr. 28, 2009", 15 pgs.
"European Application Serial No. 07754132.4, Response filed Mar. 15, 2012 to Office Action dated Sep. 5, 2011", 21 pgs.
"European Application Serial No. 07754132.4, Response filed May 10, 2013 to Office Action dated Nov. 2, 2012", 14 pgs.
"European Application Serial No. 07754132.4, Response filed Jun. 26, 2013", 8 pgs.
"European Application Serial No. 10777154.5, Communication Pursuant to Article 94(3) EPC dated Jun. 11, 2019", 3 pgs.

(56) References Cited

OTHER PUBLICATIONS

"European Application Serial No. 10777154.5, Response field May 13, 2019 to Summons to Attend Oral Proceedings mailed Jan. 7, 2019", 59 pgs.
"European Application Serial No. 10777154.5, Response field Jun. 4, 2019 to Summons to Attend Oral Proceedings mailed Jan. 7, 2019", 9 pgs.
"European Application Serial No. 10777154.5, Response filed Sep. 7, 2018 to Communication Pursuant to Article 94(3) EPC dated Apr. 4, 2018", 18 pgs.
"European Application Serial No. 10777154.5, Summons to Attend Oral Proceedings mailed Jan. 7, 2019", 5 pgs.
"European Application Serial No. 14745060.5, Communication Pursuant to Article 94(3) EPC dated Feb. 6, 2018", 5 pgs.
"European Application Serial No. 14745060.5, Office Action dated Feb. 23, 2016", 2 pgs.
"European Application Serial No. 14745060.5, Response filed Jun. 15, 2018 to Communication Pursuant to Article 94(3) EPC dated Feb. 6, 2018", 14 pgs.
"European Application Serial No. 14745060.5, Response filed Dec. 22, 2016 to Communication pursuant to Rules 161(1) and 162 EPC dated Feb. 23, 2016", 6 pgs.
"Evaluation of Medicines for human Use", EMEA/CPMP/BWP/2289/01, London, The European Agency for the Evaluation of Medicinal Products, Committee for Proprietary Medicinal Products (CPMP), (Feb. 20, 2003), 14.
"FLUZONE® Influenza Virus Vaccine", Sanofi Aventis Pasteur, Swiftwater, (Jul. 2005), 12 pgs.
"Indian Application Serial No. 02082/KOLNP/2005, Examination Report dated Mar. 17, 2008", 1 pg.
"Indian Application Serial No. 02082/KOLNP/2005, Examination Report dated Dec. 28, 2007", 1 pg.
"Indian Application Serial No. 02082/KOLNP/2005, First Examination Report dated Jan. 25, 2007", 9 pgs.
"Indian Application Serial No. 02082/KOLNP/2005, Response filed Jan. 22, 2008 to Examination Report dated Dec. 28, 2007", 13 pgs.
"Indian Application Serial No. 02082/KOLNP/2005, Response filed Jun. 10, 2008 to Examination Report dated Mar. 17, 2008", 3 pgs.
"Indian Application Serial No. 02082/KOLNP/2005, Response filed Nov. 19, 2007 to First Examination Report dated Jan. 25, 2007", 26 pgs.
"Indian Application Serial No. 1026/KOLNP/2009, First Examiner Report dated Mar. 13, 2014", 2 pgs.
"Indian Application Serial No. 2272/KOLNP/2005, First Examination Report dated Mar. 17, 2008", 10 pgs.
"Indian Application Serial No. 2272/KOLNP/2005, Response filed Mar. 16, 2009 to Subsequent Examination Report dated Mar. 6, 2009", 12 pgs.
"Indian Application Serial No. 2272/KOLNP/2005, Response filed Oct. 11, 2008 to First Examination Report dated Mar. 17, 2008", 27 pgs.
"Indian Application Serial No. 2272/KOLNP/2005, Subsequent Examination Report dated Mar. 6, 2009", 1 pg.
"Influenza B/lee/40, neuraminidase & nb (seg 6) rna", Database EM_VI E.B.I. Hinxton U.K., (Jun. 13, 1985), 10 pgs.
"International Application No. PCT/US2004/016680, International Search Report", (dated Feb. 2, 2005), 7 pgs.
"International Application Serial No. PCT/US01/11963, Amendment filed Sep. 9, 2002 to Written Opinion dated Aug. 7, 2002", 12 pgs.
"International Application Serial No. PCT/US01/11963, International Preliminary Examination Report dated Oct. 15, 2002", 13 pgs.
"International Application Serial No. PCT/US01/11963, International Search Report dated May 7, 2002", 5 pgs.
"International Application Serial No. PCT/US01/11963, Response filed Sep. 9, 2002 to Written Opinion dated Aug. 7, 2002", 12 pgs.
"International Application Serial No. PCT/US01/11963, Written Opinion dated Jun. 14, 2002", 2 pgs.
"International Application Serial No. PCT/US01/11963, Written Opinion dated Aug. 7, 2002", 6 pgs.
"International Application Serial No. PCT/US2004/012050, International Search Report dated Feb. 2, 2005", 8 pgs.
"International Application Serial No. PCT/US2004/012050, Written Opinion dated Feb. 2, 2005", 12 pgs.
"International Application Serial No. PCT/US2004/016680, International Preliminary Report on Patentability dated Dec. 15, 2005", 11 pgs.
"International Application Serial No. PCT/US2007/007562, International Preliminary Report on Patentability dated Oct. 9, 2008", 5 pgs.
"International Application Serial No. PCT/US2007/007562, International Search Report dated Jan. 14, 2008", 8 pgs.
"International Application Serial No. PCT/US2007/007562, Written Opinion dated Jan. 14, 2008", 9 pgs.
"International Application Serial No. PCT/US2008/007582, International Preliminary Report on Patentability dated Jan. 7, 2010", 9 pgs.
"International Application Serial No. PCT/US2008/007582, International Search Report and Written Opinion dated Feb. 18, 2009", 16 pgs.
"International Application Serial No. PCT/US2014/046731, International Preliminary Report on Patentability dated Jan. 28, 2016", 12 pgs.
"International Application Serial No. PCT/US2014/046731, International Search Report dated Nov. 25, 2014", 9 pgs.
"International Application Serial No. PCT/US2014/046731, Written Opinion dated Nov. 25, 2014", 10 pgs.
"International Application Serial No. PCT/US2015/036803, International Preliminary Report on Patentability dated Dec. 29, 2016", 10 pgs.
"International Application Serial No. PCT/US2015/036803, International Search Report dated Dec. 11, 2015", 8 pgs.
"International Application Serial No. PCT/US2015/036803, Invitation to Pay Add'l Fees and Partial Search Rpt dated Oct. 2, 2015", 8 pgs.
"International Application Serial No. PCT/US2015/036803, Written Opinion dated Dec. 11, 2015", 8 pgs.
"International Application Serial No. PCT/US2016/041172, International Preliminary Report on Patentability dated Jan. 18, 2018", 10 pgs.
"International Application Serial No. PCT/US2016/041172, International Search Report dated Oct. 27, 2016", 6 pgs.
"International Application Serial No. PCT/US2016/041172, Written Opinion dated Oct. 27, 2016", 8 pgs.
"International Application Serial No. PCT/US2017/018443, International Search Report dated May 22, 2017", 9 pgs.
"International Application Serial No. PCT/US2017/018443, Written Opinion dated May 22, 2017", 9 pgs.
"Israel Application Serial No. 238584, Office Action dated Jul. 24, 2017", 2 pgs.
"Israel Application Serial No. 238584, Response filed Nov. 21, 2017 to Office Action dated Jul. 24, 2017", W/English Translation, 2 pgs.
"Israeli Application Serial No. 171831, Notification of Defects dated Nov. 10, 2008", (English Translation), 10 pgs.
"Israeli Application Serial No. 171372, Office Action dated Feb. 21, 2010", (Translation), 2 pgs.
"Israeli Application Serial No. 171372, Office Action dated Nov. 6, 2008", (Translation), 12 pgs.
"Israeli Application Serial No. 171372, Response filed Nov. 18, 2010 to Office Action dated Feb. 21, 2010", (Translation), 19 pgs.
"Israeli Application Serial No. 171831, Office Action dated Feb. 21, 2010", (English Translation), 2 pgs.
"Israeli Application Serial No. 171831, Office Action dated Apr. 18, 2012", (English Translation), 2 pgs.
"Israeli Application Serial No. 171831, Response filed Jan. 20, 2011 to Office Action dated Feb. 21, 2010", (English Translation), 18 pgs.
"Israeli Application Serial No. 171831, Response filed Jun. 24, 2009 to Notification of Defects dated Nov. 10, 2008", (w/ English Translation of Claims), 10 pgs.

(56) References Cited

OTHER PUBLICATIONS

"Israeli Application Serial No. 171831, Response filed Nov. 6, 2012 to Office Action dated Apr. 18, 2012", (w/ English Translation of Amended Claims), 54 pgs.
"Israeli Application Serial No. 238584, Office Action dated Apr. 14, 2016", (English Translation), 3 pgs.
"Israeli Application Serial No. 238584, Office Action dated Jul. 24, 2017", (Translation), 2 pgs.
"Israeli Application Serial No. 238584, Response filed Aug. 3, 2016 to Office Action dated Apr. 14, 2016", (English Translation of Claims), 19 pgs.
"Israeli Application Serial No. 238584, Response filed Nov. 21, 2017 to Office Action dated Jul. 24, 2017", (Translation), 2 pgs.
"Israeli Application Serial No. 171372,Office Action dated Feb. 20, 2011", (Translation), 2 pgs.
"Japanese Application No. 2001-576868, Office Action dated May 31, 2011", (w/ English Translation), 5 pgs.
"Japanese Application No. 2001-576868, Response filed Apr. 26, 2011 to Office Action dated Nov. 2, 2010", (w/ Translation of Amended Claims), 14 pgs.
"Japanese Application Serial No. 2001-576868, Office Action dated Nov. 2, 2010", w/ English Translation), 10 pgs.
"Japanese Application Serial No. 2001-576868, Response filed Dec. 1, 2011 to Office Action dated May 3, 2011", (w/ English Translation of Amended Claims), 37 pgs.
"Japanese Application Serial No. 2006-513125, Office Action dated Mar. 9, 2010", (English Translation), 11 pgs.
"Japanese Application Serial No. 2006-513125, Response filed Aug. 30, 2010 to Office Action dated Mar. 9, 2010", (w/ English Translation of Amended Claims), 60 pgs.
"Japanese Application Serial No. 2006-533439, Decision of Final Rejection dated Aug. 14, 2012", (w/ English Translation), 5 pgs.
"Japanese Application Serial No. 2006-533439, Office Action dated Mar. 9, 2010", (w/ English Translations), 20 pgs.
"Japanese Application Serial No. 2006-533439, Office Action dated Mar. 27, 2012", w/ English Translation, 8 pgs.
"Japanese Application Serial No. 2006-533439, Response filed May 21, 2012 to Office Action dated Mar. 27, 2012", (w/ English Translation of Amended Claims), 19 pgs.
"Japanese Application Serial No. 2006-533439, Response filed Aug. 3, 2011 to Office Action dated Feb. 15, 2011", (w/ English Translation of Amended Claims), 18 pgs.
"Japanese Application Serial No. 2006-533439,Office Action dated Feb. 15, 2011", (w/ English Translation), 13 pgs.
"Japanese Application Serial No. 2006-533439; Office Action Response filed Jul. 9, 2010", (w/ English Translation of Claims), 25 pgs.
"Japanese Application Serial No. 2009-502945, Examiners Decision of Final Refusal dated Nov. 12, 2013", (w/ English Translation), 8 pgs.
"Japanese Application Serial No. 2009-502945, Office Action dated Oct. 23, 2012", (w/ English Translation), 16 pgs.
"Japanese Application Serial No. 2009-502945, Response filed Apr. 10, 2013 to Office Action dated Oct. 23, 2012", (w/ English Translation of Claims), 18 pgs.
"Japanese Application Serial No. 2011-111048, Office Action dated Jun. 25, 2013", (w/ English Translation), 7 pgs.
"Japanese Application Serial No. 2011-111048, Office Action dated Sep. 18, 2012", (w/ English Translation), 10 pga.
"Japanese Application Serial No. 2011-111048, Response filed Sep. 25, 2012 to Office Action dated Jun. 25, 2013", (w/ English Translation of Amended Claims), 18 pgs.
"Japanese Application Serial No. 2011-111048. Response filed Mar. 15, 2013", (w/ Translation of Amended Claims), 14 pgs.
"Japanese Application Serial No. 2012-273898, Office Action dated Jun. 10, 2014", (w/ English Translation), 7 pgs.
"Japanese Application Serial No. 2012-273898, Response filed Sep. 4, 2014 to Office Action dated Jun. 10, 2014", W/ English Claims, 9 pgs.
"Japanese Application Serial No. 2013-198377, Office Action dated Jan. 6, 2015", (w/ English Translation), 9 pgs.
"Japanese Application Serial No. 2014-049025 Response filed Sep. 4, 2015 to Office Action dated Jun. 16, 2015", (w/ Amended Claims), 12 pgs.
"Japanese Application Serial No. 2014-049025, Examiners Decision of Final Refusal dated Feb. 2, 2016", W/ English Translation, 5 pgs.
"Japanese Application Serial No. 2014-049025, Office Action dated Jun. 16, 2015", (w/ English Translation), 6 pgs.
"Japanese Application Serial No. 2016-110879, Office Action dated May 30, 2017", (w/ English Translation), 7 pgs.
"Japanese Application Serial No. 2016-110879, Response filed Nov. 30, 2017 to Office Action dated May 30, 2017", (w/ English Translation of Claims), 25 pgs.
"Japanese Application Serial No. 2006-513125,Final Office Action dated Jan. 18, 2011", (English Translation), 4 pgs.
"Korean Application Serial No. 10-2005-7020077, Response filed Apr. 28, 2008 to Examination Report dated Dec. 28, 2007", (w/ English Translation of Revised Claims), 41 pgs.
"Korean Application Serial No. 10-2005-7020077, Examination Report dated Dec. 28, 2007", (w/ English Translation), 8 pgs.
"Korean Application Serial No. 10-2005-7020077, Notice of Preliminary Rejection dated Jun. 28, 2007", (w/ English Translation), 9 pgs.
"Korean Application Serial No. 10-2005-7020077, Response filed Aug. 28, 2007 to Notice of Preliminary Rejection dated Jun. 28, 2007", (w/ EnglishTranslation), 40 pgs.
"Korean Application Serial No. 10-2005-7022564, Notice of Preliminary Rejection dated Jul. 25, 2007", W/ English Translation, 5 pgs.
"Korean Application Serial No. 10-2005-7022564, Office Action dated Aug. 6, 2008", W/ English Translation, 4 pgs.
"Korean Application Serial No. 10-2005-7022564, Response and Amendment filed Dec. 29, 2008 to Office Action dated Aug. 6, 2008", W/ English Translation, 16 pgs.
"Korean Application Serial No. 10-2005-7022564, Response filed Mar. 25, 2008 to Notice of Preliminary Rejection dated Jul. 25, 2007", (w/ English Translation of Claims), 35 pgs.
"Korean Application Serial No. 10-2005-7022564, Response filed Dec. 29, 2008 to Office Action dated Aug. 6, 2008", (w/ English Translation of Claims), 16 pgs.
"Mexican Application No. PA/a/2005/012712 Office Action dated Jul. 21, 2009", (w/ English Translation), 9 pgs.
"Mexican Application Serial No. MX/a/2009/006341, Office Action dated Mar. 29, 2012", (English Translation), 1 pg.
"Mexican Application Serial No. MX/a/2009/006341, Response filed Jun. 4, 2012 dated Mar. 29, 2012", (w/ English Translation of Amended Claims), 16 pgs.
"Mexican Application Serial No. MX/a/2012/009249 Response filed Sep. 10, 2015 to Office Action dated May 19, 2015", (w/ English Translation of Claims), 21 pgs.
"Mexican Application Serial No. MX/a/2012/009249, Office Action dated Feb. 5, 2016", W/ English Claims, 2 pgs.
"Mexican Application Serial No. MX/a/2012/009249, Office Action dated May 19, 2015", (English Translation), 1 pg.
"Mexican Application Serial No. MX/a/2012/009249, Response filed Mar. 29, 2016 to Office Action dated Feb. 5, 2016", (English Translation of Claims), 18 pgs.
"Mexican Application Serial No. PA/a/2005/011250, Office Action dated Aug. 23, 2010", W/ English Translation, 4 pgs.
"Mexican Application Serial No. PA/a/2005/011250, Response Filed Dec. 20, 2010 to Office Action dated Aug. 23, 2010", (w/ English Translation of Claims), 14 pgs.
"Mexican Application Serial No. PA/a/2005/012712 , Office Action dated Aug. 11, 2009", (English Translation), 5 pgs.
"Mexican Application Serial No. PA/a/2005/012712 , Response filed Sep. 28, 2009 to Office Action dated Jul. 21, 2009", (w/ English Translation of Claims), 24 pgs.
"Mexican Application Serial No. PA/a/2005/012712, Office Action dated May 12, 2010", (w/ English Translation), 19 pgs.
"Mexican Application Serial No. PA/a/2005/012712, Office Action dated Jun. 9, 2010", (w/ English Translation), 11 pgs.
"Mexican Application Serial No. PA/a/2005/012712, Office Action dated Nov. 30, 2009", (w/ English Translation), 14 pgs.

(56) References Cited

OTHER PUBLICATIONS

"Mexican Application Serial No. PA/a/2005/012712, Official Action dated Mar. 5, 2009", (English Translation), 2 pgs.
"Mexican Application Serial No. PA/a/2005/012712, Response filed Feb. 3, 2010 to Office Action dated Nov. 30, 2009", (w/ English Translation of Amended Claims), 22 pgs.
"Mexican Application Serial No. PA/a/2005/012712, Response filed Sep. 27, 2010 to Office Action dated May 12, 2010", (w/ English Translation of Claims), 19 pgs.
"Mexico Application Serial No. PA/a/2005/012712, Response filed Jun. 12, 2009 to Official Action dated Mar. 5, 2009", (w/ English Translation of Claims), 11 pgs.
"New Zealand Application Serial No. 542935, Examination Report dated Feb. 25, 2008", 2 pgs.
"New Zealand Application Serial No. 542935, Examination Report dated Jun. 14, 2006", 2 pgs.
"New Zealand Application Serial No. 542935, Response filed Jun. 30, 2008 to Examination Report dated Feb. 25, 2008", 32 pgs.
"New Zealand Application Serial No. 542935, Response filed Aug. 7, 2007 to Examination Report dated Jun. 14, 2006", 18 pgs.
"New Zealand Application Serial No. 542935, Voluntary Amendments filed Sep. 12, 2007", 10 pgs.
"New Zealand Application Serial No. 543446, Examination Report dated Feb. 29, 2008", 2 pgs.
"New Zealand Application Serial No. 543446, Examination Report dated May 12, 2008", 2 pgs.
"New Zealand Application Serial No. 543446, Response mailed Mar. 20, 2008 to Examination Report dated Feb. 29, 2008", 2 pgs.
"Norway Application Serial No. 20056074, Office Action dated Jan. 17, 2017", (English Translation), 5 pgs.
"Norway Application Serial No. 20056074, Office Action dated Apr. 25, 2017", (w English Translation), 3 pgs.
"Norway Application Serial No. 20056074, Office Action Response dated Apr. 18, 2017", W/ English Claims, 27 Pgs.
"Norway Application Serial No. 20056074, Response filed Jul. 25, 2017 to Office Action dated Apr. 25, 2017", (w/ English Translation of Amended Claims), 111 pgs.
"Norweigan Application Serial No. 20056074, Office Action dated Apr. 25, 2017", (Translation), 3 pgs.
"RecName: Full=Polymerase acidic protein {ECO:0000256|RuleBase;RU361280, ECO: 0000256|SAAS: SAAS00262764}", XP002744257, retrieved from EBI accession No. UNIPR0T:A3R6C9 Database accession No. A3R6C9 the whole document, (Apr. 3, 2007), 1 pgs.
"RecName: Full=Polymerase acidic protein {ECO:0000256|RuleBase;RU361280, ECO: 0000256|SAAS-:SAAS00262764}", XP002744258, retrieved from EBI accession No. UNIPROT:U3S198 Database accession No. U3S198 the whole document, (Dec. 11, 2013), 1 pg.
"Russian Federation Application No. 2005136233, Office Action dated Dec. 25, 2007", 2 pgs.
"Russian Federation Application No. 2005136233, Response filed May 29, 2008 to Office Action dated Dec. 25, 2007", (w/ Partial English Translation), 7 pgs.
"Russian Federation Application Serial No. 2005136233, First Office Action dated Feb. 27, 2007", (w/ English Translation), 5 pgs.
"Russian Federation Application Serial No. 2005136233, Response filed Jun. 14, 2007 to First Office Action dated Feb. 27, 2007", (English Translation of Claims), 6 pgs.
"Russian Federation Application Serial No. 2005136233, Response filed Nov. 20, 2007 to Office Action", (w/ English Translation of Amended Claims), 18 pgs.
"Singaporean Application Serial No. 200506858-0, Examination Report dated Feb. 9, 2007", 4 pgs.
"Singaporean Application Serial No. 200506858-0, Response filed Dec. 22, 2006 to Written Opinion dated Jul. 26, 2006", 18 pgs.
"Singaporean Application Serial No. 200506858-0, Written Opinion dated Jul. 26, 2006", 8 pgs.
"Singaporean Application Serial No. 200507468-7, Examination Report dated Mar. 19, 2008", 5 pgs.
"Singaporean Application Serial No. 200507468-7, Invitation to Respond to Written Opinion dated Jun. 12, 2007", 6 pgs.
"Singaporean Application Serial No. 200507468-7, Response filed Nov. 7, 2007 to Invitation to Respond to Written Opinion dated Jun. 12, 2007", 9 pgs.
"The Influenza Virus: Structure and Replication", Rapid Reference to Influenza. Elsevier Ltd, [Online]. Retrieved from the Internet: http://www. rapidreferenceinfluenza.com/chapter/B978-0-7234-3433-7.50009-8/aim/influenza-virus-structure, (2006), 6 pgs.
"The Integral Membrane Proteins of Influenza A, B, and C Viruses", The Influenza Sequence Database, http://www.flu.lanl.gov/review/fluc.review2.html, (Observed Feb. 26, 2003), 1 pg.
"Ukrainese Application Serial No. 200512619, Response filed Jan. 21, 2010 to Office Action dated Jun. 17, 2009", W/ English Claims, 14 pgs.
"Ukrainian Application Serial No. 200512619, Office Action dated Feb. 27, 2009", (w/ English Translation), 21 pgs.
"Ukrainian Application Serial No. 200512619, Office Action dated Jun. 17, 2009", (w/ English Translation), 4 pgs.
"Ukrainian Application Serial No. 200512619, Response filed Apr. 8, 2009 to Office Action dated Feb. 27, 2009", (w/ English Translation of Claims), 9 pgs.
Air, Gillian M., et al., "Antigenic, Sequence, and Crystal Variation in Influenza B Neuraminidase", Virology vol. 177,, (1990), 578-587.
Air, Gillian M., et al., "Antigenic, Sequence, and Crystal Variation in Influenza B Neuraminidase", Virology, 177(2), (1990), 578-587.
Author Unknown, "New Approaches to Influenza Vaccine", Medscape—Infections in Medicine, http://www.medscape.com/viewarticle/417404_3, (Observed Feb. 26, 2003), 4 pgs.
Avetisyan, G, et al., "Cell-mediated immune responses to influenza vaccination in healthy volunteers and allogeneic stem cell transplant recipients", Bone Marrow Transplant, (2005), 411-415.
Avilov, Sergiy V., et al., "Influenza A virus progeny vRNP trafficking in live infected cells studied with the virus-encoded fluorescently tagged PB2 protein", Vaccine, 30, (2012), 7411-7417.
Avilov, Sergiy V., et al., "Replication-Competent Influenza A Virus That Encodes a Split-Green Fluorescent Protein-Tagged PB2 Polymerase Subunit Allows", Journal of Virology, 86, (2012), 1433-1448.
Baez, M., et al., "Complete nucleotide sequence of the influenza A/PR/8/34 virus NS gene and comparison with the NS genes of the A/Udorn/72 and A/FPV/Rostock/34 strains", Nucleic Acids Research, 23(8), (1980), 5845-5858.
Bancroft, C. T, et al., "Evidence for segment-nonspecific packaging of the influenza a virus genome", J Virol., 76(14), (Jul. 2002), 7133-9.
Banerjee, A. K., et al., "Gene Expression of Vesicular Stomatitis Virus Genome RNA.", Virology, 188(2), (1992), 417-428.
Baron, M. D., et al., "Rescue of Rinderpest Virus From Cloned cDNA", Journal of Virology, 71(2), (1997), 1265-1271.
Basler, C. F, et al., "Mutation of Neuraminidase Cysteine Residues Yields Temprature-Sensitive Influenza Viruses", Journal of Virology, 73(10), (Jun. 30, 1999), 8095-8103.
Beare, A. S., "Trials in Man With Live Recombinants Made From A/PR/8/34 (H0 N1) and Wild H3 N2 Influenza Viruses", The Lancet, 2(7938), (1975), 729-732.
Betakova, T., et al., "The NB protein is an integral component of the membrane of influenza B virus.", J Gen Virol., 77 ( Pt 11), (Nov. 1996), 2689-94.
Bourmakina, S. V, et al., "Reverse genetics studies on the Filamentous morphology of influenza A Virus", Journal of General Virology (2003) 84 (2003), 517-527.
Bowie, J. U., et al., "Deciphering the Message in Protein Sequences: Tolerance to Amino Acid Substitutions", Science, 247(4948), (1990), 1306-1310.
Boyer, J. C., et al., "Infectious transcripts and cDNA clones of RNA viruses", Virology, 198(2), (Feb. 1994), 415-426.
Brassard, D.L., et al., "Influenza B virus NB glycoprotein is a component of the virion", Virol., 220(2), No Document, (1996), 350-360.

(56) References Cited

OTHER PUBLICATIONS

Bridgen, A., "Rescue of a Segmented Negative-Strand RNA Virus Entirely From Cloned Complementary DNAs", Proc. Natl. Acad. Sci. USA, 93, (1996), 15400-15404.
Brooke, C B, "Biological activities of 'noninfectious' influenza A virus particles", Future Virol 9(1), (Jan. 2014), 41-51.
Brown, E. G., et al., "Genetic analysis of mouse-adapted influenza A virus identifies roles for the NA, PB1, and PB2 genes in virulence", Virus Research, 61(1), (May 1999), 63-76.
Buchholz, U. J., et al., "Generation of Bovine Respiratory Syncytial Virus (BRSV) From cDNA: BRSV NS2 is Not Essentiial for Virus Replication in Tissue Culture, and the Human RSV Leader Region Acts as a Functional BRSV Genome Promoter", Journal of Virology, 73(1), (1999), 251-259.
Bukreyev, A., et al., "Recovery of infectious respiratory syncytial virus expressing an additional, foreign gene", Journal of Virology, 70(10), (Oct. 1996), 6634-6641.
Cao, S., et al., "Characterization of the Nucleocytoplasmic Shuttle of the Matrix Protein of Influenza B Virus", Journal of Virology., 88(13), (Jul. 2014), 7464-7473.
Castrucci, Maria R., et al., "Reverse genetics system for generation of an influenza A virus mutant containing a deletion of the carboxyl-terminal residue of M2 protein.", J Virol., 69(5), (May 1995), 2725-8.
Chen, H, et al., "Generation and evaluation of a high-growth reassortant H9N2 influenza A virus as a pandemic vaccine candidate", Vaccine, 21(17-18), (May 16, 2003), 1974-9.
Chen, Z., et al., "Influenza A Virus NS1 Protein Targets Poly(A)-Binding Protein II of the Cellular 3'-End Processing Machinery", The EMBO Journal, 18(8), (1999), 2273-2283.
Chevalie, Christophe, et al., "PB1-F2 Influenza A Virus Protein Adopts a B-Sheet Conformation and Forms Amyloid Fibers in Membrane Environments", The of Biological Chemistry, 285(17), (2010), 13233-13243.
Clarke, D. K., et al., "Rescue of Mumps Virus From cDNA", Journal of Virology, 74(10), (2000), 4831-4838.
Collins, P. L., et al., "Chapter 41—Parainfluenza Viruses", In: Fields Virology, edited by Fields, B. N., et al. (3rd Edition, 1996, Lippincott—Raven Publishers, Philadelphia, PA, 1205-1241.
Collins, P. L., et al., "Production of Infectious Human Respiratory Syncytial Virus From Cloned cDNA Confirms an Essential Role for the Transcription Elongation Factor From the 5' Proximal Open Reading Frame of the M2 mRNA in Gene Expression and Provides a Capability for Vaccine D", Proc. Natl. Acad. Sci. USA, 92, (1995), 11563-11567.
Collins, P. L., "Rescue of Synthetic Analogs of Respiratory Syncytial Virus Genomic RNA and Effect of Truncations and Mutations on the Expression of a Foreign Reporter Gene", Proc. Natl. Acad. Sci. USA, 88, (1991), 9663-9667.
Conzelmann, K.-K., "Genetic Engineering of Animal RNA Viruses", Trends in Microbiology, 4(10), (1996), 386-393.
Conzelmann, K.-K., "Genetic manipulation of non-segmented negative-strand RNA viruses", Journal of General Virology, 77(Pt. 3), (Mar. 1996), 381-389.
Conzelmann, K.-K., "Nonsegmented Negative-Strand RNA Viruses: Genetics and Manipulation of Viral Genomes", Annu. Rev. Genet., 32, (1998), 123-162.
Conzelmann, K.-K., "Rescue of Synthetic Genomic RNA Analogs of Rabies Virus by Plasmid-Encoded Proteins", Journal of Virology, 68(2), (1994), 713-719.
De, B. P., et al., "Requirements and Functions of Vesicular Stomatitis Virus L and NS Proteins in the Transcription Process in Vitro", Biochemical and Biophysical Research Communications, 126(1), (1985), 40-49.
De, B. P., et al., "Rescue of synthetic analogs of genome RNA of human parainfluenza virus type 3", Virology, 196(1), (Sep. 1993), 344-348.
De, B. P., et al., "Reverse Genetics of Negative Strand RNA Viruses", Indian Journal of Biochemistry & Biophysics, 31, (1994), 367-375.
De Filette, Marina, et al., "An influenza A vaccine based on tetrameric ectodomain of matrix protein 2", J Biol Chem. 2008 ; 283 (17):, (Feb. 5, 2008), 11382-7.
De La Luna, S., et al., "Influenza virus naked RNA can be expressed upon transfection into cells co-expressing the three subunits of the polymerase and the nucleoprotein from simian virus 40 recombinant viruses", Journal of General Virology, 74(pt. 3), (Mar. 1993), 535-539.
De La Luna, S., et al., "Influenza Virus NS1 Protein Enhances the Rate of Translation Initiation of Viral mRNAs", Journal of Virology, 69(4), (1995), 2427-2435.
Desheva, J. A, et al., "Characterization of an influenza A H5N2 reassortant as a candidate for live-attenuated and inactivated vaccines against highly pathogenic H5N1 viruses with pandemic potential", Vaccine, (2006), 6859-6866.
Dimmock, Nigel J, et al., "In vivo antiviral activity: defective interfering virus protects better against virulent Influenza A virus than avirulent virus", Journal of General Virology 87, (Jan. 8, 2006), 1259-1265.
Dimock, K., et al., "Rescue of Synthetic Analogs of Genomic RNA and Replicative-Intermediate RNA of Human Parainfluenza Virus Type 3", Journal of Virology, 67(5), (1993), 2772-2778.
Dos Santos Afonso, Emmanuel, et al., "The generation of recombinant influenza A viruses expressing a PB2 fusion protein requires the conservation of a packaging signal overlapping the coding and noncoding regions at the 5V end of the PB2 segment", Virology, 341, (2005), 34-46.
Dreher, T. W., et al., "Mutational Analysis of the Sequence and Structural Requirements in Brome Mosaic Virus RNA for Minus Strand Promoter Activity", Journal of Molecular Biology, 201(1), (1988), 31-40.
Duff, K. C., et al., "The secondary structure of influenza A M2 transmembrane domain", FEBS Letters, 311 (3), (Oct. 1992), pp. 256-258.
Duff, K. C., et al., "The Transmembrane Domain of Influenza A M2 Protein Forms Amantadine-Sensitive Proton Channels in Planar Lipid Bilayers", Vilology, 190(1), (Sep. 1992), pp. 485-489.
Dunn, E. F., et al., "Transcription of a recombinant bunyavirus RNA template by transiently expressed bunyavirus proteins", Virology, 211(1), (1995), 133-143.
Durbin, A. P., et al., "Recovery of infectious human parainfluenza virus type 3 from cDNA", Virology, 235(2), (Sep. 1, 1997), 323-332.
Elhefnawi, M, et al., "Identification of novel conserved functional motifs across most Influenza A viral strains", Virol J. Jan. 27, 2011;8:44. doi: 10.1186/1743-422X-8-44, (2011), 2 pgs.
Elliott, R. M., et al., "Rescue of Infectious Bunyavirus Entirely From Cloned cDNA", 10th International Conference on Negative Strand Virus, (Abstract No. 96), (1997), 1 pg.
Elliott, R. M., et al., "Some Highlights of Virus Research in 1990", Journal of General Virology, 72(Part 8), (1991), 1761-1779.
Emerson, S. U., et al., "Both NS and L Proteins Are Required for In Vitro RNA Synthesis by Vesicular Stomatitis Virus", Journal of Virology, 15(6), (1975), 1348-1356.
Enami, M., "An Influenza Virus Containing Nine Different RNA Segments", Virology, 185(1), (1991), 291-298.
Enami, M., et al., "High-Efficiency Formation of Influenza Virus Transfectants", Journal of Virology, 65(5), (1991), 2711-2713.
Enami, M., et al., "Introduction of Site-Specific Mutations Into the Genome of Influenza Virus", Proc. Natl. Acad. Sci. USA, 87, (1990), 3802-3805.
Fahey, J. L., "Status of Immune-Based Therapies in HIV Infection and Aids", Clinincal and Experimental Immunology, 88(1), (1992), 1-5.
Fan, J, et al., "Preclinical study of influenza virus A M2 peptide conjugate vaccines in mice, ferrets, and rhesus monkeys", Vaccine, 22, (2004), 2993-3003.
Fischer, W. B, et al., "Viral ion channels: structure and function.", Biochim Biophys Acta., 1561(1), (Mar. 19, 2002), 27-45.
Fleming, D. M, et al., "Comparison of the efficacy and safety of live attenuated cold-adapted influenza vaccine, trivalent, with trivalent inactivated influenza virus vaccine in children and adolescents with asthma", Pediatr Infect Dis J., 25(10), (2006), 860-869.

(56) References Cited

OTHER PUBLICATIONS

Forbes, Nicole E, et al., "Multifunctional Adaptive NS1 Mutations Are Selected upon Human Influenza Virus Evolution in the Mouse", Plos One, vol. 7, No. 2, (Feb. 21, 2012).
Fortes, P., et al., "Influenza Virus NS1 Protein Inhibits Pre-mRNA Splicing and Blocks mRNA Nucleocytoplasmic Transport", The EMBO Journal, 13(3), (1994), 704-712.
Fujii, Ken, et al., "Importance of both the Coding and the Segment-Speci?c Noncoding Regions of the In?uenza A Virus NS Segment for Its Ef?cient", Journal of Virology, 79(6), (Mar. 2005), 3766-3774.
Gao, Qinshan, et al., "A Nine-Segment In?uenza A Virus Carrying Subtype H1 and H3 Hemagglutinins†", Journal of Virology, 84(16), (Aug. 2010), 8062-8071.
Gao, Qinshan, et al., "The In?uenza A Virus PB2, PA, NP, and M Segments Play a Pivotal Role during Genome Packaging", Journal of Virology, 86(13), Chou, (Jul. 2011), 043-7051.
Garcia-Sastre, A., et al., "Genetic Manipulation of Negative-Strand RNA Virus Genomes", Annu. Rev. Microbiol., 47, (1993), 765-790.
Garcin, D., et al., "A Highly Recombinogenic System for the Recovery of Infectious Sendai Paramyxovirus From cDNA: Generation of a Novel Copy-Back Nondefective Interfering Virus", The EMBO Journal, 14(24), (1995), 6087-6094.
Giddings, A M, et al., "The matrix protein of HIV-1 is not sufficient for assembly and release of virus-like particles", Virology, 248(1), (1998), 108-16.
Gorman, O T, "Evolution of influenza A virus PB2 genes: implications for evolution of the ribonucleoprotein complex and origin of human influenza A virus", Department of Virology and Molecular Biology, St. Jude Children's Research Hospital, Memphis Tennessee 38101-0318J. Virol. Oct. 1990; 64(10):4893-902, (1990), 2 pgs.
Gotea, V, et al., "The functional relevance of somatic synonymous mutations in melanoma and other cancers", Pigment Cell & Melanoma Research, 28 issue 6, (Nov. 1, 2015), 673-686.
Goto, H., "Mutations Affecting the Sensitivity of the Influenza Virus Neuraminidase to 4-Guanidino-2, 4-dideoxy 2, 3-dehydro-N-acetylneuraminic Acid", Virology, 238, (1997), 265-272.
Govorkova, E A, et al., "Replication of Influenza A Viruses in a Green Monkey Kidney Continuous Cell Line (Vero)", J. Infect. Dis. 172(1), (1995), 250-253.
Grambas, S., et al., "Influence of amantadine resistance mutations on the pH regulatory function of the M2 protein of influenza A viruses", Virology, 191(2), (Dec. 1992), 541-549.
Grosfeld, H., et al., "RNA Replication by Respiratory Syncytial Virus (RSV) Is Directed by the N, P, and L Proteins; Transcription Also Occurs Under These Conditions but Requires RSV Superinfection for Efficient Synthesis of Full-Length mRNA", Journal of Virology, 69(9), (1995), 5677-5686.
Hai, Rong, et al., "Influenza B Virus NS1-Truncated Mutants: Live-Attenuated Vaccine Approach", Journal of Virology, 82(21), (2008), 10580-10590.
Harty, Ronald N, "A Proline-Rich Motif within the Matrix Protein of Vesicular Stomatitis Virus and Rabies Virus Interacts with WW Domains of Cellular Proteins: Implications for Viral Budding", Journal of Virology, 73 (4), (1999), 2921-2929.
Hatada, E., et al., "Binding of Influenza A Virus NS1 Protein to dsRNA in vitro", Journal of General Virology, 73, (1992), 3325-3329.
Hatta, M., et al., "The NB protein of influenza B virus is not necessary for virus replication in vitro", Journal of Virology, 77(10), (May 2003), 6050-6054.
Hay, A. J., et al., "The role of the M2 protein in influenza A virus infection", Proceedings of the International Conference on Options for the Control of Influenza, Courchevel, (1992), 281-288.
He, B., et al., "Recovery of infectious SV5 from cloned DNA and expression of a foreign gene", Virology, 237(2), (1997), 249-260.
Helenius, A., "Unpacking the Incoming Influenza Virus", Cell, 69, (May 1992), pp. 577-578.
Hevey, Michael, et al., "Marburg virus vaccines based upon alphavirus replicons protect guinea pigs and nonhuman primates", Virology, 251(1), (Nov. 10, 1998), 28-37.
Hiromoto, Y., et al., "Phylogenetic Analysis of the Three Polymerase Genes (PB1, PB2 and PA) of Influenza B Virus", Journal of General Virology, 81, (Apr. 2000), 929-937.
Hoffman, M. A., et al., "An Infectious Clone of Human Parainfluenza Virus Type 3", Journal of Virology, 71(6), (1997), 4272-4277.
Hoffmann, E., et al., "A DNA transfection system for generation of influenza A virus from eight plasmids", Proc Natl Acad Sci U S A., 97(11), (May 23, 2000), 6108-13.
Hoffmann, E., et al., "Ambisense Approach for the Generation of Influenza A Virus: vRNA and mRNA Synthesis from One Template", Virology, 267, (2000), 310-317.
Hoffmann, E., et al., "Eight-plasmid System for Rapid Generation of Influenza Virus Vaccines", Vaccine, Butterworth Scientific Guildford, 20(25-56), (Aug. 19, 2002), 3165-3170.
Hoffmann, E., et al., "Rescue of Influenza B Virus from Eight Plasmids", Proceedings of the National Academy of Sciences of USA, National Academy of Science, 99(17), (Aug. 20, 2002), 11411-11416.
Holmes, E. C, et al., "Whole-Genome Analysis of Human Influenza A Virus Reveals Multiple Persistent Lineages and Reassortment Among Recent H3N2 Viruses", PLoS Biology, 3(9), (2005), 1579-1589.
Holsinger, L. J., et al., "Influenza A Virus M2 Ion Channel Protein: a Structure-Function Analysis", Journal of Virology, 68 (3), (1994), pp. 1551-1563.
Honda, Ayae, et al., "Differential Roles of Viral RNA and cRNA in Functional Modulation of the Influenza Virus RNA Polymerase", The Journal of Biological Chemistry, 276(33), (2001), 31179-31185.
Horimoto, T., et al., "Enhanced growth of seed viruses for H5N1 influenza vaccines", Virology, 366(1), (Sep. 15, 2007), 23-27.
Horimoto, T., et al., "Generation of Influenza A Viruses with Chimeric (Type A/B) Hemagglutinins", Journal of Virology, 77(14), (2003), 8031-8038.
Horimoto, T., et al., "The Development and Characterization of H5 Influenza Virus Vaccines Derived from a 2003 Human Isolate", Vaccine, 24(17), (2006), 3669-3676.
Huang, T.-S., et al., "Determination of Influenza Virus Proteins Required for Genome Replication", Journal of Virology, 64(11), (1990), 5669-5673.
Hunt, R., "Virology—Chapter Eight—Vaccines: Past Successes and Future Prospects", Microbiology and Immunology On-Line, http://www.med.sc.edu:85/lecture/vaccines.htm, (Observed Feb. 26, 2003), 15 pgs.
Isakova-Sivak, Irina, et al., "Characterization of Reverse Genetics-Derived Cold-Adapted Master Donor Virus A/Leningrad/134/17/57 (H2N2) and Reassortants with H5N1 Surface Genes in a Mouse Model", Clinical and Vaccine Immunology, 21(5), (May 2014), 722-731.
Ives, J. A., et al., "The H274Y mutation in the influenza A/H1N1 neuraminidase active site following oseltamivir phosphate treatment leave virus severely compromised both in vitro and in vivo.", Antiviral Research, 55(2), (2002), 307-317.
Iwatsuki-Horimoto, K., et al., "The cytoplasmic tail of the influenza A virus M2 protein plays a role in viral assembly.", J Virol., 80(11), (Jun. 2006), 5233-40.
Jackson, D., et al., "A reverse genetics approach for recovery of recombinant influenza B viruses entirely from cDNA.", J Virol., 76(22), (Nov. 2002), 11744-7.
Jasenosky, Luke D, et al., "Ebola Virus VP40-Induced Particle Formation and Association with the Lipid Bilayer", Journal of Virology, 75 (110, (Jun. 2001), 5205-5214.
Kaplan, G., et al., "In vitro Synthesis of Infectious Poliovirus RNA", Proc. Natl. Acad. Sci. USA, 82, (1985), 8824-8428.
Katinger, D., et al., "Attenuated Influenza Viruses as a Vector for Mucosal Immunization Against HIV-1", Vaccines, 97, Cold Spring Harbor, (1997), 315-319.
Kato, A., et al., "Initiation of Sendai Virus Multiplication From Transfected cDNA or RNA With Negative or Positive Sense", Genes to Cells, 1, (1996), 569-579.

(56) References Cited

OTHER PUBLICATIONS

Kawaoka, Y, et al., “Sequence requirements for cleavage activation of influenza virus hemagglutinin expressed in mammalian cells”, Proc Natl Acad Sci., 85(2), (1988), 324-328.
Kawaoka, Y., “Mutant Cells With Altered Sialic Acid”, U.S. Appl. No. 11/644,179, filed Dec. 22, 2006, 51 pgs.
Kilbourne, E. D, et al., “Related studies of a recombinant influenza-virus vaccine. I. Derivation and characterization of virus and vaccine”, J Infect Dis., 124(5), (Nov. 1971), 449-62.
Kim, H., et al., “Cold adaptation generates mutations associated with the growth of influenza B vaccine viruses”, Vaccine, 33(43), (2015), 5786-5793.
Kimura, N., et al., “An In Vivo Study of the Replication Origin in the Influenza Virus Complementary RNA”, The Journal of Biochemistry, 113(1), (1993), 88-92.
Kimura, N., et al., “Transcription of a Recombinant Influenza Virus RNA in Cells That Can Express the Influenza Virus RNA Polymerase and Nucleoprotein Genes”, Journal of General Virology, 73, (1992), 1321-1328.
Kiseleva, I., et al., “Role of individual genes of the A-Leningrad/134/17/57 (H2N2) cold-adapted donor strain in manifestation of the temperature-sensitive phenotype of reassortant influenza A viruses”, International Congress Series, vol. 1263, (2004), 547-550.
Kittel, Christian, et al., “Generation of an In?uenza A Virus Vector Expressing Biologically Active Human Interleukin-2 from the NS Gene Segment”, Journal of Virology, 79(16), (Aug. 2005), 10672-10677.
Kobayashi, M., et al., “Reconstitution of Influenza Virus RNA Polymerase From Three Subunits Expressed Using Recombinant Baculovirus System”, Virus Research, 22, (1992), 235-245.
Kochendoerfer, G. G, et al., “Total Chemical Synthesis of the Integral Membrane Protein Influenza A Virus M2: Role of its C-Terminal Domain in Tetramer Assembly”, Biochemistry 38, (1999), 11905-11913.
Konarska, M. M., et al., “Structure of RNAs Replicated by the DNA-Dependent T7 RNA Polymerase”, Cell, 63(2), (1990), 609-618.
Krystal, M., et al., “Expression of the Three Influenza Virus Polymerase Proteins in a Single Cell Allows Growth Complementation of Viral Mutants”, Proc. Natl. Acad. Sci. USA, 83, (1986), 2709-2713.
Krystal, M., “Influenza B/Lee/40, hemagglutinin (seg 4), complete segment.”, Database EM_VI E.B.I. Hinxton U.K., (Apr. 25, 1990).
Kunkel, T. A., “Rapid and Efficient Site-Specific Mutagenesis Without Phenotypic Selection”, Proc. Natl. Acad. Sci. USA, 82, (1985), 488-492.
Lamb, Robert A., et al., “Chapter 20—Paramyxoviridae: The Viruses and Their Replication”, In: Fundamental Virology, Fields, B. N., et al., editors, Lippincott-Raven (2nd Edition), (1996), 577-647.
Lawson, N. D., “Recombinant Vesicular Stomatitis Viruses From DNA”, Proc. Natl. Acad. Sci. USA, 92(10), (1995), 4477-4481.
Lazarovits, Janette, et al., “Endocytosis of Chimeric Influenza Virus Hemaggulutinin Proteins That Lack a Cytoplasmic Recognition Feature for Coated Pits”, The Journal of Cell Biology, vol. 134, No. 2, (1996), 339-348.
Lee, C. W, et al., “Generation of reassortant influenza vaccines by reverse genetics that allows utilization of a DIVA (Differentiating Infected from Vaccinated Animals) strategy for the control of avian influenza”, Vaccine, vol. 22, (2004), 3175-3181.
Lee, Dong-Hun, et al., “Progress and hurdles in development of influenza virus-like particle vaccines for veterinary use”, Korean Vaccine Society, (2014), 133-139.
Levis, R., et al., “Deletion Mapping of Sindbis Virus DI RNAs Derived From cDNAs Defines the Sequences Essential for Replication and Packaging”, Cell, 44, (1986), 137-145.
Li, Y, et al., “Viral liposomes released from insect cells infected with recombinant baculovirus expressing the matrix protein of vesicular stomatitis virus”, Journal of Virology, 67 (7), (1993), 4415-4420.
Liu, Bo, et al., “[Comparison of three methods in construction fusion gene of influenza A virus Nucleoprotein].”, (English Abstract), Zhonghua Shi Yan He Lin Chuang Bing Du Xue Za Zhi, 26(1), 70-74, (Feb. 2012), 1 pg.
Lu, Xiuhua, et al., “Cross-protective immunity in mice induced by live-attenuated or inactivated vaccines against highly pathogenic influenza A (H5N1) viruses”, Vaccine, 24(44-46), (2006), 6588-6593.
Luo, M., “Inhibitors of Influenza Virus Neuraminidase”, Abstract No. WO296, from a paper presented at the Annual Meeting of the American Crystallographic Association, http://www.hwi.buffalo.edu/ACA/ACA98/abstracts/text/WO296.html, (Observed Feb. 27, 2003), 1 pg.
Luytjes, W., “Amplification, Expression, and Packaging of a Foreign Gene by Influenza Virus”, Cell, 59(6), (1989), 1107-1113.
Manicassamy, Balaji, et al., “Analysis of in vivo dynamics of influenza virus infection in mice using a GFP reporter virus”, Proc Natl Acad Sci. USA, 107(25), (2010), 11531-11536.
Manz, Benjamin, et al., “Disruption of the Viral Polymerase Complex Assembly as a Novel Approach to Attenuate Influenza A Virus”, The Journal of Biological Chemistry, 286(10), (2011), 8414-8424.
Mark, A, et al., “Effect of Mutations and Deletions in a Bicistronic mRNA on the Synthesis of Influenza B Virus NB and NA Glycoproteins”, Journal of Virology, vol. 77, No. 10, (May 2003), 6050-6054.
Matsuoka, et al., “Neuraminidase Stalk Length and Additional Glycosylation of the Hemagglutinin Influence the Virulence of Influenza H5N1 Viruses for Mice”, Journal of Virology, vol. 83, No. 9 (2009), pp. 4704-4708.
McCown, M F, et al., “The influenza a virus M2 cytoplasmic tail is required for infectious virus production and efficient genome packaging.”, J Virol., 79(6), (Mar. 2005), 3595-605.
Mccown, M. F, et al., “Distinct domains of the influenza A virus M2 protein cytoplasmic tail mediate binding to the M1 protein and facilitate infectious virus production.”, J Virol., 80(16), (Aug. 2006), 8178-89.
McKimm, J. L., et al., “Mutations in a Conserved Residue in the Influenza Virus Neuraminidase Active Site Decreases Sensitivity to Neu5Ac2en-Derived Inhibitors”, Journal of Virology, 72(3), (1998), 2456-2462.
Mebatsion, Teshome, et al., “Budding of Rabies Virus Particles in the Absence of the Spike Glycoprotein”, Cell, 84(6), (1996), 941-951.
Mebatsion, Teshome, et al., “Matrix Protein of Rabies Virus Is Responsible for the Assembly and Budding of Bullet-Shaped Particles and Interacts with the Transmembrane Spike Glycoprotein G”, Journal of Virology, 73 (1), (Jan. 1999), 242/250.
Mena, I., “Rescue of a Synthetic Choramphenicol Acetyltransferase RNA into influenza Virus-Like Particles obtained from recombinant plasmids”, Journal of Virology, 70(8), (1996), 5016-5024.
Mena, I., et al., “Synthesis of Biologically Active Influenza Virus Core Proteins Using a Vaccinia Virus-T7 RNA Polymerase Expression System”, Journal of General Virology, 75, (1994), 2109-2114.
Mitnaul, et al., “The Cytoplasmic Tail of Influenza a Virus Neuraminidase (NA) Affects NA Incorporation into Virons, Viron Morphology, and Virulence in Mice but is not essential for Virus Replication”, Journal of Virology, 70 (2), (1996), 873-879.
Monto, Arnold S, et al., “Comparative efficacy of inactivated and live attenuated influenza vaccines.”, N Engl J Med., 361(13), (Sep. 24, 2009), 1260-7.
Moyer, S. A., et al., “Assembly and Transcription of Synthetic Vesicular Stomatitis Virus Nucleocapsids”, Journal of Virology, 65(5), (1991), 2170-2178.
Murphy, Brian R, et al., “Virulence of Avian Influenza A Viruses for Squirrel Monkeys”, Infection and Immunity 37 (3), (Sep. 1982), 1119-1126.
Muster, T., et al., “An Influenza A Virus Containing Influenza B Virus 5' and 3' Noncoding Regions on the Neuraminidase Gene is Attenuated in Mice”, Proc. Natl. Acad. Sci. USA, 88, (1991), 5177-5181.

(56) References Cited

OTHER PUBLICATIONS

Naito, S., et al., "Function and Structure of RNA Polymerase From Vesicular Stomatitis Virus", The Journal of Biological Chemistry, 251(14), (1976), 4307-4314.
Nara, P. L., et al., "Simple, Rapid, Quantitative, Syncytium-Forming Microassay for the Detection of Human Immunodeficiency Virus Neutralizing Antibody", Aids Research and Human Retroviruses, 3(3), (1987), 283-302.
Neirynck, S., "A universal influenza A vaccine based on the extracellular domain of the M2 protein", Nature Medicine, 5 (10), (Oct. 1999), pp. 1157-1163.
Nemeroff, M. E., et al., "Influenza Virus NS1 Protein Interacts With the Cellular 30 kDa Subunit of CPSF and Inhibits 3' End Formation of Cellular Pre-mRNAs", Molecular Cell, 1(7), (1998), 991-1000.
Neumann, G., et al., "Generation of influenza A virus from cloned cDNAs—historical perspective and outlook for the new millenium.", Rev Med Virol., 12(1), XP002314285, (Jan.-Feb. 2002), 13-30.
Neumann, G., et al., "Generation of influenza A viruses entirely from cloned cDNAs", Proc. Natl. Acad. Sci. USA., 96(16), (1999), 9345-9350.
Neumann, G., et al., "Plasmid-driven formation of influenza virus-like particles", J Virol., 74(1), [Online] Retrieved From Internet: <http://www.ncbi.nlm.nih.gov/pmc/articles/PMC111569/>, (Jan. 2000), 547-551.
Neumann, G., et al., "RNA Polymerase I-Mediated Expression of Influenza Viral RNA Molecules", Virology, 202(1), (1994), 477-479.
Neumann, Gabriele, et al., "Reverse Genetics Demonstrates that Proteolytic Processing of the Ebola Virus Glycoprotein Is Not Essential for Replication in Cell Culture", Journal of Virology, 76 (1), (Jan. 2002), 406-410.
Noda, Takeshi, et al., "Three-dimensional analysis of ribonucleoprotein complexes in influenza A virus", Nature Communications, 3, (2012), 1-6.
Odagiri, T., et al., "Nucleotide Sequence of the PA Gene of Influenza A/WSN/33 (H1N1)", Nucleic Acids Research, 18 (3), Department of Virology, (Jan. 9, 1990).
Orkin, S. H, et al., "Report and Recommendations of the Panel to Assess the NIH Investment in Research on Gene Therapy", http://www.nih.gov/news/panelrep.html, (Dec. 7, 1995), 37 pgs.
Palese, P., et al., "47. Orthomyxoviridae: The Viruses and Their Replication", In: Fields Virology (5th Edition), (2007), 90 pgs.
Palese, P., "Negative-Strand RNA Viruses: Genetic Engineering and Applications", Proc. Natl. Acad. Sci. USA, 93(21), (1996), 11354-11358.
Park, Eun K., et al., "The M2 Ectodomain is important for its incorporation into influenza A virions", J. of Virology, vol. 72, No. 3, XP002196797, (Mar. 1998), 2449-2455.
Park, K. H., et al., "Rescue of a Foreign Gene by Sendai Virus", Proc. Natl. Acad. Sci. USA, 88, (1991), 5537-5541.
Pattnaik, A. K., et al., "Cells That Express All Five Proteins of Vesicular Stomatitis Virus From Cloned cDNAs Support Replication, Assembly, and Budding of Defective Interfering Particles", Proc. Natl. Acad. Sci. USA, 88(4), (1991), 1379-1383.
Peeters, B. P. H., et al., "Rescue of Newcastle Disease Virus From Cloned cDNA: Evidence That Cleavability of the Fusion Protein Is a Major Determinant for Virulence", Journal of Virology, 73(6), (1999), 5001-5009.
Pekosz, A., "Commentary—Reverse Genetics of Negative-Strand RNA Viruses: Closing the Circle", Proc. Natl. Acad. Sci. USA, 96, (1999), 8804-8806.
Pekosz, A., et al., "Influenza C virus CM2 integral membrane glycoprotein is produced from a polypeptide precursor by cleavage of an internal signal sequence", PNAS, vol. 95, XP002196653, (Oct. 1998), 13233-13238.
Percy, N., et al., "Expression of a Foreign Protein by Influenza A Virus", Journal of Virology, 68(7), (1994), 4486-4492.
Perez, Jasmine T., et al., "Unit 15G.4—Insertion of a GFP Reporter Gene in Influenza Virus", Curr Protoc Microbiol., (2013), 20 pgs.
Piller, S C., et al., "Vpr protein of human immunodeficiency virus type 1 forms cation-selective channels in planar lipid bilayers", PNAS, 93, (1996), 111-1115.
Ping, J, et al., "Development of high-yield influenza A virus vaccine viruses", Nature Communications, [online]. Retrieved from the Internet: <http://www.nature.eom/article-assets/npg/ncomms/2015/150902/ncomms9148/extref/ncomms9148-sl.pdf>, (Sep. 2, 2015), 50 pgs.
Ping, J., et al., "Development of high-yield influenza B virus vaccine viruses", Proc. Natl. Acad. Sci. USA, 113(51), (2016), E8296-E8305, and 25 pgs of Supplemental Material.
Pinto, L. H., et al., "Influenza Virus M2 Protein Has Ion Channel Activity", Cell, 69, (May 1992), pp. 517-528.
Plant, E P, et al., "Mutations to A/PuertoRico/8/34 PB1 gene improves seasonal reassortant influenza A virus growth kinetics", Vaccine, vol. 31, No. 1, (Dec. 1, 2012), 207-212 pgs.
Pleschka, S., et al., "A Plasmid-Based Reverse Genetics System for Influenza A Virus", Journal of Virology, 70(6), (1996), 4188-4192.
Qiu, Y., et al., "The Influenza Virus NS1 Protein Binds to a Specific Region in Human U6 snRNA and Inhibits U6-U2 and U6-U4 snRNA Interactions During Splicing", RNA, 1, (1995), 304-316.
Qiu, Y., et al., "The Influenza Virus NS1 Protein Is a Poly(A)-Binding Protein That Inhibits Nuclear Export of mRNAs Containing Poly(A)", Journal of Virology, 68(4), (1994), 2425-2432.
Racaniello, V. R., et al., "Cloned Poliovirus Complimentary DNA Is Infectious in Mammalian Cells", Science, 214, (1981).
Radecke, F., et al., "Rescue of Measles Viruses From Cloned DNA", The EMBO Journal, 14(23), (1995), 5773-5784.
Radecke, F., et al., "Reverse Genetics Meets the Nonsegmented Negative-Strand RNA Viruses", Reviews in Medical Virology, 7, (1997), 49-63.
Roberts, A., et al., "Minireview—Recovery of Negative-Strand RNA Viruses From Plasmid DNAs: A Positive Approach Revitalizes a Negative Field", Virology, 247(1), (1998), 1-6.
Rose, J. K., "Positive Strands to the Rescue Again: A Segmented Negative-Strand RNA Virus Derived From Cloned cDNAs", Proc. Natl. Acad. Sci. USA, 94, (1996), 14998-15000.
Ruigrok, R W, et al., "Characterization of three highly purified influenza virus strains by electron microscopy", J Gen Virol 65 ( Pt 4), (Apr. 1984), 799-802.
Ruigrok, R W, et al., "Structural Characterization and Membrane Binding Properties of the Matrix Protein VP40 of Ebola Virus", Journal of Molecular Biology, 300(1), (2000), 103-112.
Sansom, M. S., et al., "Influenza virus M2 Protein: a molecular modelling study of the ion channel", Protein Engineering, 6 (1), (1993), pp. 65-74.
Schickli, J. H, et al., "Plasmid-only Rescue of Influenza A Virus Vaccine Candidates", Philosophical Transactions of the Royal Society of London. Series B, Biological Sciences, 356(1416), (Dec. 29, 2001), 1965-1973.
Schlesinger, S., "RNA Viruses as Vectors for the Expression of Heterologous Proteins", Molecular Biotechnology, 3(2), (1995), 155-165.
Schnell, M. J., "Infectious Rabies Viruses From Cloned cDNA", The EMBO Journal, 13(18), (1994), 4195-4203.
Schnell, Matthias J, et al., "Requirement for a non-specific glycoprotein cytoplasmic domain sequence to drive efficient budding of vesicular stomatitis virus", EMBO Journal, 17 (5), (1998), 1289-1296.
Schotsaert, M, et al., "Universal M2 ectodomain-based influenza A vaccines: preclinical and clinical developments", Expert Rev V accines. Apr. 2009;8(4):, 499-508.
Seong, B. L., et al., "A New Method for Reconstituting Influenza Polymerase and RNA in Vitro: A Study of the Promoter Elements for cRNA and vRNA Synthesis in Vitro and Viral Rescue in Vivo", Virology, 186(1), (1992), 247-260.
Shinya, Kyoko, et al., "Characterization of a Neuraminidase-Deficient Influenza A Virus as a Potential Gene Delivery Vector and a Live Vaccine", Journal of Virology, 78(6), (2004), 3083-3088.
Sidhu, M. S., et al., "Rescue of Synthetic Measles Virus Minireplicons: Measles Genomic Termini Direct Efficient Expression and Propagation of a Reporter Gene", Virology, 208, (1995), 800-807.

(56) References Cited

OTHER PUBLICATIONS

Skehel, J. J., et al., "On the Mechanism of Inhibition of Influenza Virus Replication by Amantadine Hydrochloride", The Journal of General Virology, 38 (1), (1977), pp. 97-110.
Smeenk, et al., "Mutations in the Hemagglutinin and Matrix Genes of a Virulent Influenza Virus Variant, A/FM/1/47-MA, Control Different Stages in Pathogenesis", Virus Research 44, (1996), 79-95.
Subbarao, E. K., et al., "Sequential Addition of Temperature-Sensitive Missense Mutations into the PB2 Gene of Influenza A Transfectant Viruses Can Effect an Increase in Temperature Sensitivity and Attenuation and Permits the Rational Design of a Genetically Engineered Live Influen", Journal of Virology, 69(10), (1995), 5969-5977.
Subbarao, K., et al., "Evaluation of a Genetically Modified Reassortant H5N1 Influenza A Virus Vaccine Candidate Generated by Plasmid-based Reverse Genetics", Virology, vol. 305(1), (Jan. 5, 2003), 192-200.
Sugrue, R. J., et al., "Specific structural alteration of the influenza haemagglutinin by amantadine", The EMBO Journal, 9 (11), (1990), pp. 3469-3476.
Sugrue, R. J., et al., "Structural Characteristics of the M2 Protein of Influenza A Viruses: Evidence That It Forms a Tetrameric Channel", Virology, 180, (1991), pp. 617-624.
Suguitan, A. L, et al., "Live, Attenuated Influenza A H5N1 Candidate Vaccines Provide Broad Cross-Protection in Mice and Ferrets", PLoS Med., 3(9), (2006), 1541-1555.
Sunstrom, N. A., et al., "Ion Channels formed by NB, an influenza B virus Protein", J. of Membrane Biology, vol. 150, XP002196654, (Dec. 1996), 127-132.
Sweet, T. M., et al., "Creation of amantadine resistant clones of influenza type A virus using a new transfection procedure.", J Virol Methods., 69(1-2), (Dec. 1997), 103-11.
Szewczyk, B., "Purification, Thioredoxin Renaturation, and Reconstituted Activity of the Three Subunits of the Influenza A Virus RNA Polymerase", Proc. Natl. Acad. Sci. USA, 85, (1988), 7907-7911.
Takeda, M., et al., "Influenza a virus M2 ion channel activity is essential for efficient replication in tissue culture.", J Virol., 76(3), (Feb. 2002), 1391-9.
Takeuchi, K., et al., "Influenza Virus M2 Protein Ion Channel Activity Stabilizes the Native Form of Fowl Plague Virus Hemagglutinin during Intracellular Transport", Journal of Virology, 68 (2), (Feb. 1994), pp. 911-919.
Tannock, G. A, et al., "Relative immunogenicity of the cold-adapted influenza virus A/Ann Arbor/6/60 (A/AA/6/60-ca), recombinants of A/AA/6/60-ca, and parental strains with similar surface antigens.", Infect Immun., 43(2), (Feb. 1984), 457-62.
Taylor, J., et al., "Newcastle Disease Virus Fusion Protein Expressed in a Fowlpox Virus Recombinant Confers Protection in Chickens", Journal of Virology, 64(4), (1990), 1441-1450.
Tobler, K, "Effect of cytoplasmic tail truncations on the activity of the M(2) ion channel of influenza A virus", J Virol., (1999), 9695-701.
Uraki, R., et al., "A Novel Bivalent Vaccine Based on a PB2-Knockout Influenza Virus Protects Mice from Pandemic H1N1 and Highly Pathogenic H5N1 Virus Challenges", Journal of Virology, 87(14), (2013), 7874-7881.
Verma, I. M, et al., "Gene Therapy—Promises, Problems and Prospects", Nature, 389, (1997), 239-242.
Voeten, J. T, et al., "Characterization of high-growth reassortant influenza A viruses generated in MDCK cells cultured in serum-free medium", Vaccine, vol. 17, (1999), 1942-1950.
Volchkov, Viktor E, et al., "Recovery of Infectious Ebola Virus from Complementary DNA: RNA Editing of the GP Gene and Viral Cytotoxicity", Science Magazine, 291, (Mar. 2001), 1965-1969.
Wagner, R., et al., "Interdependence of hemagglutinin glycosylation and neuraminidase as regulators of influenza virus growth: a study by reverse genetics", Journal of Virology, 74 (14), (Jul. 2000), 6316-6323.
Wang, C., et al., "Ion Channel Activity of Influenza A Virus M2 Protein: Characterization of the Amantadine Block", Journal of Virology, 67 (9), (Sep. 1993), pp. 5585-5594.
Wang, Wenlig, et al., "Robust Immunity and Heterologous Protection against Influenza in Mice Elicited by a Novel Recombinant NP-M2e Fusion Protein Expressed in *E. coli*", PLoS One 7(12): e52488, (Dec. 2012), 1-13.
Ward, C. D., et al., "Direct Measurement of the Poliovirus RNA Polymerase Error Frequency In Vitro", Journal of Virology, 62(2), (1988), 558-562.
Wareing, M. D, et al., "Immunogenic and isotype-specific responses to Russian and US cold-adapted influenza a vaccine donor strains A/Leningrad/134/17/57, A/Leningrad/134/47/57, and A/Ann Arbor/6/60 (H2N2) in mice.", J Med Virol., 65(1), (Sep. 2001), 171-7.
Watanabe, et al., "Novel Approach to the Development of Effective H5N1 In?uenza A Virus Vaccines: Use of M2 Cytoplasmic Tail Mutants", Journal of Virology, 82(5), (2008), 2486-2492.
Watanabe, S., et al., "Influenza A Virus Lacking M2 Protein as a Live Attenuated Vaccine", Journal of Virology, 83(11), (2009), 5947-5950.
Watanabe, T., et al., "Influenza A virus can undergo multiple cycles of replication without M2 ion channel activity", J Virol., 75(12), (Jun. 2001), 5656-62.
Watanabe, T., et al., "Influenza A Virus with Defective M2 Ion Channel Activity as a Live Vaccine", Virology, 299(2), (Aug. 1, 2002), 266-270.
Watanabe, Tokiko, et al., "Exploitation of Nucleic Acid Packaging Signals to Generate a Novel In?uenza Virus-Based Vector Stably Expressing Two Foreign Genes", Journal of Virology, 77(19), (Oct. 2003), 10575-10583.
Watanabe, Tokiko, et al., "Influenza A Virus Can Undergo Multiple Cycles of Replication without M2 Ion Channel Activity", Journal of Virology 75(12), (2001), 5656-5662.
Wei, Hung-Ju, et al., "Fabrication of influenza virus-like particles using M2 fusion proteins for imaging single viruses and designing vaccines", Vaccine, 29, (2011), 7163-7172.
Whelan, S. P. J., et al., "Efficient Recovery of Infectious Vesicular Stomatitis Virus Entirely from cDNA Clones", Proc. Natl. Acad. Sci. USA, 92, (1995), 8388-8392.
Williams, Mark A., et al., "Effect of Mutations and Deletions in a Bicistronic mRNA on the Synthesis of Influenza B Virus NB and NA Glycoproteins", Journal of Virology, 63(1), (1989), 28-35.
Wilson, Julie A, et al., "Epitopes Involved in Antibody-Mediated Protection from Ebola Virus", Science, 287, (Mar. 2000), 1664-1666.
Winter, G., et al., "The use of synthetic oligodeoxynucleotide primers in cloning and sequencing segment 8 of influenza virus (A/PR/8/34)", Nucleic Acids Res., 9(2), (1981), 237-245.
Wu, Rui, et al., "A live bivalent influenza vaccine based on a H9N2 virus strain", Vaccine, 28, (2010), 673-680.
Yamanaka, K., et al., "In vivo Analysis of the Promoter Structure of the Influenza Virus RNA Genome Using a Transfection System With an Engineered RNA", Proc. Natl. Acad. Sci. USA, 88, (1991), 5369-5373.
Yannarell, Dean A., et al., "Factors affecting the yield of cold-adapted influenza virus vaccine", Journal of Virological Methods, vol. 64, 161-169, (1997), 1 pg.
Yu, Q., et al., "Functional cDNA Clones of the Human Respiratory Syncytial (RS) Virus N, P, and L Proteins Support Replication of RS Virus Genomic RNA Analogs and Define Minimal trans-Acting Requirements for RNA Replication", Journal of Virology, 69(4), (1995), 2412-2419.
Yusoff, K., et al., "Nucleotide Sequence Analysis of the L Gene of Newcastle Disease Virus: Homologies With Sendai and Vesicular Stomatitis Viruses", Nucleic Acids Research, 15(10), (1987), 3961-3976.
Zaghouani, H, et al., "Induction of Antibodies to the Envelope Protein of the Human Immunodeficiency Virus by Immunization With Monoclonal Anti-Idiotypes", Proc. Natl. Acad. Sci. USA, 88, (1991), 5645-5649.
Zaghouani, H., et al., "Cells Expressing an H Chain 1g Gene Carrying a Viral T Cell Epitope are Lysed by Specific Cytolytic T Cells", The Journal of Immunology, 148(11), (1992), 3604-3609.

(56) References Cited

OTHER PUBLICATIONS

Zebedee, S. L, et al., "Characterization of the Influenza Virus M2 Integral Membrane Protein and Expression at the Infected-Cell Surface from Cloned cDNA", Journal of Virology, 56(2), (Nov. 1985), 502-511.
Zhang, H., et al., "Expression of Functional Influenza Virus A Polymerase Proteins and Template From Cloned cDNAs in Recombinant Vaccinia Virus Infected Cells", Biochemical and Biophysical Research Communications, 200(1), (1994), 95-101.
Zobel, A., et al., "RNA Polymerase I Catalysed Transcription of Insert Viral cDNA", Nucleic Acids Research, 21(16), (1993), 3607-3614.
"European Application Serial No. 10777154.5, Response filed Jul. 29, 2019 to Communication Pursuant to Article 94(3) EPC dated Jun. 11, 2019", 57 pgs.

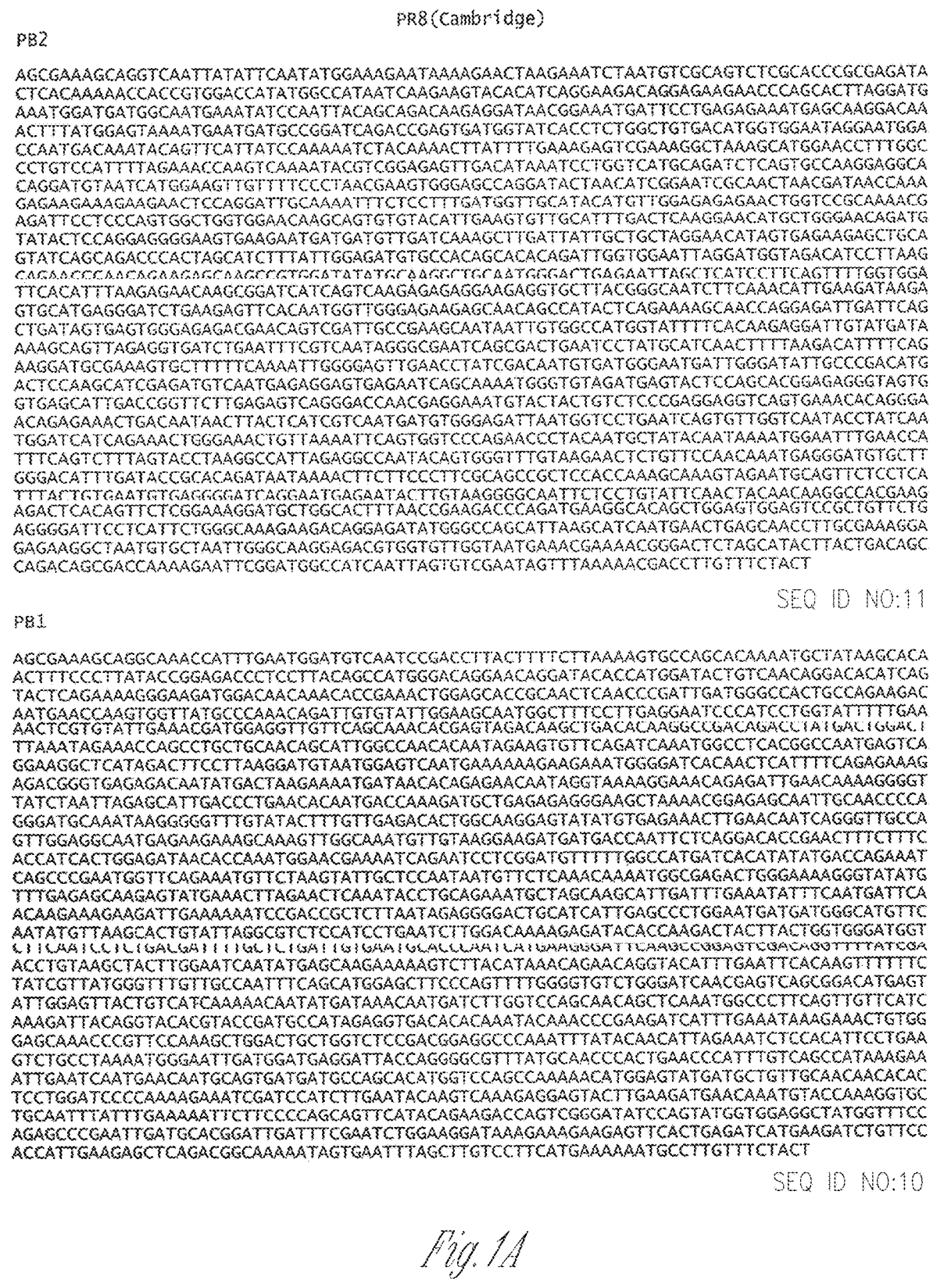

PR8(Cambridge)

PB2

AGCGAAAGCAGGTCAATTATATTCAATATGGAAAGAATAAAAGAACTAAGAAATCTAATGTCGCAGTCTCGCACCCGCGAGATA
CTCACAAAAACCACCGTGGACCATATGGCCATAATCAAGAAGTACACATCAGGAAGACAGGAGAAGAACCCAGCACTTAGGATG
AAATGGATGATGGCAATGAAATATCCAATTACAGCAGACAAGAGGATAACGGAAATGATTCCTGAGAGAAATGAGCAAGGACAA
ACTTTATGGAGTAAAATGAATGATGCCGGATCAGACCGAGTGATGGTATCACCTCTGGCTGTGACATGGTGGAATAGGAATGGA
CCAATGACAAATACAGTTCATTATCCAAAAATCTACAAAACTTATTTTGAAAGAGTCGAAAGGCTAAAGCATGGAACCTTTGGC
CCTGTCCATTTTAGAAACCAAGTCAAAATACGTCGGAGAGTTGACATAAATCCTGGTCATGCAGATCTCAGTGCCAAGGAGGCA
CAGGATGTAATCATGGAAGTTGTTTTCCCTAACGAAGTGGGAGCCAGGATACTAACATCGGAATCGCAACTAACGATAACCAAA
GAGAAGAAAGAAGAACTCCAGGATTGCAAAATTTCTCCTTTGATGGTTGCATACATGTTGGAGAGAGAACTGGTCCGCAAAACG
AGATTCCTCCCAGTGGCTGGTGGAACAAGCAGTGTGTACATTGAAGTGTTGCATTTGACTCAAGGAACATGCTGGGAACAGATG
TATACTCCAGGAGGGGAAGTGAAGAATGATGATGTTGATCAAAGCTTGATTATTGCTGCTAGGAACATAGTGAGAAGAGCTGCA
GTATCAGCAGACCCACTAGCATCTTTATTGGAGATGTGCCACAGCACACAGATTGGTGGAATTAGGATGGTAGACATCCTTAAG
CAGAACCCAACAGAAGAGCAAGCCGTGGATATATGCAAGGCTGCAATGGGACTGAGAATTAGCTCATCCTTCAGTTTTGGTGGA
TTCACATTTAAGAGAACAAGCGGATCATCAGTCAAGAGAGAGGAAGAGGTGCTTACGGGCAATCTTCAAACATTGAAGATAAGA
GTGCATGAGGGATCTGAAGAGTTCACAATGGTTGGGAGAAGAGCAACAGCCATACTCAGAAAAGCAACCAGGAGATTGATTCAG
CTGATAGTGAGTGGGAGAGACGAACAGTCGATTGCCGAAGCAATAATTGTGGCCATGGTATTTTCACAAGAGGATTGTATGATA
AAAGCAGTTAGAGGTGATCTGAATTTCGTCAATAGGGCGAATCAGCGACTGAATCCTATGCATCAACTTTTAAGACATTTTCAG
AAGGATGCGAAAGTGCTTTTTCAAAATTGGGGAGTTGAACCTATCGACAATGTGATGGGAATGATTGGGATATTGCCCGACATG
ACTCCAAGCATCGAGATGTCAATGAGAGGAGTGAGAATCAGCAAAATGGGTGTAGATGAGTACTCCAGCACGGAGAGGGTAGTG
GTGAGCATTGACCGGTTCTTGAGAGTCAGGGACCAACGAGGAAATGTACTACTGTCTCCCGAGGAGGTCAGTGAAACACAGGGA
ACAGAGAAACTGACAATAACTTACTCATCGTCAATGATGTGGGAGATTAATGGTCCTGAATCAGTGTTGGTCAATACCTATCAA
TGGATCATCAGAAACTGGGAAACTGTTAAAATTCAGTGGTCCCAGAACCCTACAATGCTATACAATAAAATGGAATTTGAACCA
TTTCAGTCTTTAGTACCTAAGGCCATTAGAGGCCAATACAGTGGGTTTGTAAGAACTCTGTTCCAACAAATGAGGGATGTGCTT
GGGACATTTGATACCGCACAGATAATAAAACTTCTTCCCTTCGCAGCCGCTCCACCAAAGCAAAGTAGAATGCAGTTCTCCTCA
TTTACTGTGAATGTGAGGGGATCAGGAATGAGAATACTTGTAAGGGGCAATTCTCCTGTATTCAACTACAACAAGGCCACGAAG
AGACTCACAGTTCTCGGAAAGGATGCTGGCACTTTAACCGAAGACCCAGATGAAGGCACAGCTGGAGTGGAGTCCGCTGTTCTG
AGGGGATTCCTCATTCTGGGCAAAGAAGACAGGAGATATGGGCCAGCATTAAGCATCAATGAACTGAGCAACCTTGCGAAAGGA
GAGAAGGCTAATGTGCTAATTGGGCAAGGAGACGTGGTGTTGGTAATGAAACGAAAACGGGACTCTAGCATACTTACTGACAGC
CAGACAGCGACCAAAAGAATTCGGATGGCCATCAATTAGTGTCGAATAGTTTAAAAACGACCTTGTTTCTACT

SEQ ID NO:11

PB1

AGCGAAAGCAGGCAAACCATTTGAATGGATGTCAATCCGACCTTACTTTTCTTAAAAGTGCCAGCACAAAATGCTATAAGCACA
ACTTTCCCTTATACCGGAGACCCTCCTTACAGCCATGGGACAGGAACAGGATACACCATGGATACTGTCAACAGGACACATCAG
TACTCAGAAAAGGGAAGATGGACAACAAACACCGAAACTGGAGCACCGCAACTCAACCCGATTGATGGGCCACTGCCAGAAGAC
AATGAACCAAGTGGTTATGCCCAAACAGATTGTGTATTGGAAGCAATGGCTTTCCTTGAGGAATCCCATCCTGGTATTTTTGAA
AACTCGTGTATTGAAACGATGGAGGTTGTTCAGCAAACACGAGTAGACAAGCTGACACAAGGCCGACAGACCTATGACTGGACT
TTAAATAGAAACCAGCCTGCTGCAACAGCATTGGCCAACACAATAGAAGTGTTCAGATCAAATGGCCTCACGGCCAATGAGTCA
GGAAGGCTCATAGACTTCCTTAAGGATGTAATGGAGTCAATGAAAAAAGAAGAAATGGGGATCACAACTCATTTTCAGAGAAAG
AGACGGGTGAGAGACAATATGACTAAGAAAATGATAACACAGAGAACAATAGGTAAAAGGAAACAGAGATTGAACAAAAGGGGT
TATCTAATTAGAGCATTGACCCTGAACACAATGACCAAAGATGCTGAGAGAGGGAAGCTAAAACGGAGAGCAATTGCAACCCCA
GGGATGCAAATAAGGGGGTTTGTATACTTTGTTGAGACACTGGCAAGGAGTATATGTGAGAAACTTGAACAATCAGGGTTGCCA
GTTGGAGGCAATGAGAAGAAAGCAAAGTTGGCAAATGTTGTAAGGAAGATGATGACCAATTCTCAGGACACCGAACTTTCTTTC
ACCATCACTGGAGATAACACCAAATGGAACGAAAATCAGAATCCTCGGATGTTTTTGGCCATGATCACATATATGACCAGAAAT
CAGCCCGAATGGTTCAGAAATGTTCTAAGTATTGCTCCAATAATGTTCTCAAACAAAATGGCGAGACTGGGAAAAGGGTATATG
TTTGAGAGCAAGAGTATGAAACTTAGAACTCAAATACCTGCAGAAATGCTAGCAAGCATTGATTTGAAATATTTCAATGATTCA
ACAAGAAAGAAGATTGAAAAAATCCGACCGCTCTTAATAGAGGGGACTGCATCATTGAGCCCTGGAATGATGATGGGCATGTTC
AATATGTTAAGCACTGTATTAGGCGTCTCCATCCTGAATCTTGGACAAAAGAGATACACCAAGACTACTTACTGGTGGGATGGT
CTTCAATCCTCTGACGATTTTGCTCTGATTGTGAATGCACCCAATCATGAAGGGATTCAAGCCGGAGTCGACAGGTTTTATCGA
ACCTGTAAGCTACTTGGAATCAATATGAGCAAGAAAAAGTCTTACATAAACAGAACAGGTACATTTGAATTCACAAGTTTTTTC
TATCGTTATGGGTTTGTTGCCAATTTCAGCATGGAGCTTCCCAGTTTTGGGGTGTCTGGGATCAACGAGTCAGCGGACATGAGT
ATTGGAGTTACTGTCATCAAAAACAATATGATAAACAATGATCTTGGTCCAGCAACAGCTCAAATGGCCCTTCAGTTGTTCATC
AAAGATTACAGGTACACGTACCGATGCCATAGAGGTGACACACAAATACAAACCCGAAGATCATTTGAAATAAAGAAACTGTGG
GAGCAAACCCGTTCCAAAGCTGGACTGCTGGTCTCCGACGGAGGCCCAAATTTATACAACATTAGAAATCTCCACATTCCTGAA
GTCTGCCTAAAATGGGAATTGATGGATGAGGATTACCAGGGGCGTTTATGCAACCCACTGAACCCATTTGTCAGCCATAAAGAA
ATTGAATCAATGAACAATGCAGTGATGATGCCAGCACATGGTCCAGCCAAAAACATGGAGTATGATGCTGTTGCAACAACACAC
TCCTGGATCCCCAAAAGAAATCGATCCATCTTGAATACAAGTCAAAGAGGAGTACTTGAAGATGAACAAATGTACCAAAGGTGC
TGCAATTTATTTGAAAAATTCTTCCCCAGCAGTTCATACAGAAGACCAGTCGGGATATCCAGTATGGTGGAGGCTATGGTTTCC
AGAGCCCGAATTGATGCACGGATTGATTTCGAATCTGGAAGGATAAAGAAAGAAGAGTTCACTGAGATCATGAAGATCTGTTCC
ACCATTGAAGAGCTCAGACGGCAAAAATAGTGAATTTAGCTTGTCCTTCATGAAAAAATGCCTTGTTTCTACT

SEQ ID NO:10

*Fig. 1A*

PR8(Cambridge)

PA

AGCGAAAGCAGGTACTGATTCAAAATGGAAGATTTTGTGCGACAATGCTTCAATCCGATGATTGTCGAGCTTGCGGAAAAAACA
ATGAAAGAGTATGGGGAGGACCTGAAAATCGAAACAAACAAATTTGCAGCAATATGCACTCACTTGGAAGTATGCTTCATGTAT
TCAGATTTCCACTTCATCAATGAGCAAGGCGAGTCAATAATCGTAGAACTTGGTGATCCTAATGCACTTTTGAAGCACAGATTT
GAAATAATCGAGGGAAGAGATCGCACAATGGCCTGGACAGTAGTAAACAGTATTTGCAACACTACAGGGGCTGAGAAACCAAAG
TTTCTACCAGATTTGTATGATTACAAGGAAAATAGATTCATCGAAATTGGAGTAACAAGGAGAGAAGTTCACATATACTATCTG
GAAAAGGCCAATAAAATTAAATCTGAGAAAACACACATCCACATTTTCTCGTTCACTGGGGAAGAAATGGCCACAAGGGCCGAC
TACACTCTCGATGAAGAAAGCAGGGCTAGGATCAAAACCAGGCTATTCACCATAAGACAAGAAATGGCCAGCAGAGGCCTCTGG
GATTCCTTTCGTCAGTCCGAGAGAGGAGAAGAGACAATTGAAGAAAGGTTTGAAATCACAGGAACAATGCGCAAGCTTGCCGAC
CAAAGTCTCCCGCCGAACTTCTCCAGCCTTGAAAATTTTAGAGCCTATGTGGATGGATTCGAACCGAACGGCTACATTGAGGGC
AAGCTGTCTCAAATGTCCAAAGAAGTAAATGCTAGAATTGAACCTTTTTTGAAAACAACACCACGACCACTTAGACTTCCGAAT
GGGCCTCCCTGTTCTCAGCGGTCCAAATTCCTGCTGATGGATGCCTTAAAATTAAGCATTGAGGACCCAAGTCATGAAGGAGAG
GGAATACCGCTATATGATGCAATCAAATGCATGAGAACATTCTTTGGATGGAAGGAACCCAATGTTGTTAAACCACACGAAAAG
GGAATAAATCCAAATTATCTTCTGTCATGGAAGCAAGTACTGGCAGAACTGCAGGACATTGAGAATGAGGAGAAAATTCCAAAG
ACTAAAAATATGAAAAAAACAAGTCAGCTAAAGTGGGCACTTGGTGAGAACATGGCACCAGAAAAGGTAGACTTTGACGACTGT
AAAGATGTAGGTGATTTGAAGCAATATGATAGTGATGAACCAGAATTGAGGTCGCTTGCAAGTTGGATTCAGAATGAGTTCAAC
AAGGCATGCGAACTGACAGATTCAAGCTGGATAGAGCTTGATGAGATTGGAGAAGATGTGGCTCCAATTGAACACATTGCAAGC
ATGAGAAGGAATTATTTCACATCAGAGGTGTCTCACTGCAGAGCCACAGAATACATAATGAAGGGGGTGTACATCAATACTGCC
TTACTTAATGCATCTTGTGCAGCAATGGATGATTTCCAATTAATTCCAATGATAAGCAAGTGTAGAACTAAGGAGGGAAGGCGA
AAGACCAACTTGTATGGTTTCATCATAAAAGGAAGATCCCACTTAAGGAATGACACCGACGTGGTAAACTTTGTGAGCATGGAG
TTTTCTCTCACTGACCCAAGACTTGAACCACACAAATGGGAGAAGTACTGTGTTCTTGAGATAGGAGATATGCTTCTAAGAAGT
GCCATAGGCCAGGTTTCAAGGCCCATGTTCTTGTATGTGAGGACAAATGGAACCTCAAAAATTAAAATGAAATGGGGAATGGAG
ATGAGGCGTTGTCTCCTCCAGTCACTTCAACAAATTGAGAGTATGATTGAAGCTGAGTCCTCTGTCAAAGAGAAAGACATGACC
AAAGAGTTCTTTGAGAACAAATCAGAAACATGGCCCATTGGAGAGTCTCCCAAAGGAGTGGAGGAAAGTTCCATTGGGAAGGTC
TGCAGGACTTTATTAGCAAAGTCGGTATTTAACAGCTTGTATGCATCTCCACAACTAGAAGGATTTTCAGCTGAATCAAGAAAA
CTGCTTCTTATCGTTCAGGCTCTTAGGGACAATCTGGAACCTGGGACCTTTGATCTTGGGGGGCTATATGAAGCAATTGAGGAG
TGCCTAATTAATGATCCCTGGGTTTTGCTTAATGCTTCTTGGTTCAACTCCTTCCTTACACATGCATTGAGTTAGTTGTGGCAG
TGCTACTATTTGCTATCCATACTGTCCAAAAAAGTACCTTGTTTCTACT

SEQ ID NO:12

NP

AGCAAAAGCAGGGTAGATAATCACTCACTGAGTGACATCAAAATCATGGCGTCCCAAGGCACCAAACGGTCTTACGAACAGATG
GAGACTGATGGAGAACGCCAGAATGCCACTGAAATCAGAGCATCCGTCGGAAAAATGATTGGTGGAATTGGACGATTCTACATC
CAAATGTGCACAGAACTTAAACTCAGTGATTATGAGGGACGGTTGATCCAAAACAGCTTAACAATAGAGAGAATGGTGCTCTCT
GCTTTTGACGAAAGGAGAAATAAATACCTGGAAGAACATCCCAGTGCGGGGAAAGATCCTAAGAAAACTGGAGGACCTATATAC
AGAAGAGTAAACGGAAAGTGGATGAGAGAACTCATCCTTTATGACAAAGAAGAAATAAGGCGAATCTGGCGCCAAGCTAATAAT
GGTGACGATGCAACGGCTGGTCTGACTCACATGATGATCTGGCATTCCAATTTGAATGATGCAACTTATCAGAGGACAAGGGCT
CTTGTTCGCACCGGAATGGATCCCAGGATGTGCTCTCTGATGCAAGGTTCAACTCTCCCTAGGAGGTCTGGAGCCGCAGGTGCT
GCAGTCAAAGGAGTTGGAACAATGGTGATGGAATTGGTCAGGATGATCAAACGTGGGATCAATGATCGGAACTTCTGGAGGGGT
GAGAATGGACGAAAAACAAGAATTGCTTATGAAAGAATGTGCAACATTCTCAAAGGGAAATTTCAAACTGCTGCACAAAAAGCA
ATGATGGATCAAGTGAGAGAGAGCCGGAACCCAGGGAATGCTGAGTTCGAAGATCTCACTTTTCTAGCACGGTCTGCACTCATA
TTGAGAGGGTCGGTTGCTCACAAGTCCTGCCTGCCTGCCTGTGTGTATGGACCTGCCGTAGCCAGTGGGTACGACTTTGAAAGA
GAGGGATACTCTCTAGTCGGAATAGACCCTTTCAGACTGCTTCAAAACAGCCAAGTGTACAGCCTAATCAGACCAAATGAGAAT
CCAGCACACAAGAGTCAACTGGTGTGGATGGCATGCCATTCTGCCGCATTTGAAGATCTAAGAGTATTGAGCTTCATCAAAGGG
ACGAAGGTGGTCCCAAGAGGGAAGCTTTCCACTAGAGGAGTTCAAATTGCTTCCAATGAAAATATGGAGACTATGGAATCAAGT
ACACTTGAACTGAGAAGCAGGTACTGGGCCATAAGGACCAGAAGTGGAGGAAACACCAATCAACAGAGGGCATCTGCGGGCCAA
ATCAGCATACAACCTACGTTCTCAGTACAGAGAAATCTCCCTTTTGACAGAACAACCGTTATGGCAGCATTCACTGGGAATACA
GAGGGGAGAACATCTGACATGAGGACCGAAATCATAAGGATGATGGAAAGTGCAAGACCAGAAGATGTGTCTTTCCAGGGGCGG
GGAGTCTTCGAGCTCTCGGACGAAAAGGCAGCGAGCCCGATCGTGCCTTCCTTTGACATGAGTAATGAAGGATCTTATTTCTTC
GGAGACAATGCAGAGGAGTACGACAATTAAAGAAAAATACCCTTGTTTCTACT

SEQ ID NO:13

M

AGCAAAAGCAGGTAGATATTGAAAGATGAGTCTTCTAACCGAGGTCGAAACGTACGTTCTCTCTATCATCCCGTCAGGCCCCCT
CAAAGCCGAGATCGCACAGAGACTTGAAGATGTCTTTGCAGGGAAGAACACCGATCTTGAGGTTCTCATGGAATGGCTAAAGAC
AAGACCAATCCTGTCACCTCTGACTAAGGGGATTTTAGGATTTGTGTTCACGCTCACCGTGCCCAGTGAGCGAGGACTGCAGCG
TAGACGCTTTGTCCAAAATGCCCTTAATGGGAACGGGGATCCAAATAACATGGACAAAGCAGTTAAACTGTATAGGAAGCTCAA
GAGGGAGATAACATTCCATGGGGCCAAAGAAATCTCACTCAGTTATTCTGCTGGTGCACTTGCCAGTTGTATGGGCCTCATATA
CAACAGGATGGGGGCTGTGACCACTGAAGTGGCATTTGGCCTGGTATGTGCAACCTGTGAACAGATTGCTGACTCCCAGCATCG

Fig. 1B

PR8(Cambridge)

GTCTCATAGGCAAATGGTGACAACAACCAACCCACTAATCAGACATGAGAACAGAATGGTTTTAGCCAGCACTACAGCTAAGGC
TATGGAGCAAATGGCTGGATCGAGTGAGCAAGCAGCAGAGGCCATGGAGGTTGCTAGTCAGGCTAGGCAAATGGTGCAAGCGAT
GAGAACCATTGGGACTCATCCTAGCTCCAGTGCTGGTCTGAAAAATGATCTTCTTGAAAATTTGCAGGCCTATCAGAAACGAAT
GGGGGTGCAGATGCAACGGTTCAAGTGATCCTCTCGCTATTGCCGCAAATATCATTGGGATCTTGCACTTGATATTGTGGATTC
TTGATCGTCTTTTTTTCAAATGCATTTACCGTCGCTTTAAATACGGACTGAAAGGAGGGCCTTCTACGGAAGGAGTGCCAAAGT
CTATGAGGGAAGAATATCGAAAGGAACAGCAGAGTGCTGTGGATGCTGACGATGGTCATTTTGTCAGCATAGAGCTGGAGTAAA
AAACTACCTTGTTTCTACT

SEQ ID NO:14

NS

AGCAAAAGCAGGGTGACAAAGACATAATGGATCCAAACACTGTGTCAAGCTTTCAGGTAGATTGCTTTCTTTGGCATGTCCGCA
AACGAGTTGCAGACCAAGAACTAGGTGATGCCCCATTCCTTGATCGGCTTCGCCGAGATCAGAAATCCCTAAGAGGAAGGGGCA
GCACTCTTGGTCTGGACATCGAGACAGCCACACGTGCTGGAAAGCAGATAGTGGAGCGGATTCTGAAAGAAGAATCCGATGAGG
CACTTAAAATGACCATGGCCTCTGTACCTGCGTCGCGTTACCTAACCGACATGACTCTTGAGGAAATGTCAAGGGAATGGTCCA
TGCTCATACCCAAGCAGAAAGTGGCAGGCCCTCTTTGTATCAGAATGGACCAGGCGATCATGGATAAAAACATCATACTGAAAG
CGAACTTCAGTGTGATTTTTGACCGGCTGGAGACTCTAATATTGCTAAGGGCTTTCACCGAAGAGGGAGCAATTGTTGGCGAAA
TTTCACCATTGCCTTCTCTTCCAGGACATACTGCTGAGGATGTCAAAAATGCAGTTGGAGTCCTCATCGGAGGACTTGAATGGA
ATGATAACACAGTTCGAGTCTCTGAAACTCTACAGAGATTCGCTTGGAGAAGCAGTAATGAGAATGGGAGACCTCCACTCACTC
CAAAACAGAAACGAGAAATGGCGGGAACAATTAGGTCAGAAGTTTGAAGAAATAAGATGGTTGATTGAAGAAGTGAGACACAAA
CTGAAGGTAACAGAGAATAGTTTTGAGCAAATAACATTTATGCAAGCCTTACATCTATTGCTTGAAGTGGAGCAAGAGATAAGA
ACTTTCTCATTTCAGCTTATTTAATAATAAAAAACACCCTTGTTTCTACT

SEQ ID NO:15

Fig.1C

COMPARISON OF AMINO ACID SEQUENCES
BETWEEN WT AND PR8-VERO

| | POSITION | WT | PR8-VERO |
|---|---|---|---|
| HA2 | 117 | N | D |
| NA | 255 | N | Y |
| PB2 | 740 | D | N(2/4) |

Fig.3

POSITION OF HA2 117 IN THE 3D STRUCTURE OF HA

1934 HUMAN H1 HEMAGGLUTININ (MMDB ID: 26941, PDB ID: 1RU7)

THE HA2 N117D MUTANT FUSED CELLS AT A HIGHER PH THAN DID WT.

THE PRINCIPAL OF THE METHOD OF COMPARISON OF ENDOSOMAL pH BETWEEN TWO DIFFERENT CELLS (MDCK VS. VERO CELLS)

FLUORESCENCE INTENSITY OF OREGON GREEN IS SENSITIVE TO LOW PH ALTHOUGH INTENSITY OF ALEXA647 IS NOT SENSITIVE TO PH VALUE.

PH CAN BE COMPARED BY MEASURING THE INTENSITY AND CALCULATING THE RATIO BETWEEN ALEXA647 AND OREGON GREEN.

THE A/KAWASAKI/173/2001 (H1N1) 6:2 REASSORTANT WITH A PR8 DONOR IN VERO CELLS

THE A/KAWASAKI/UTK-4/2009 (H1N1) 6:2 REASSORTANT WITH A PR8 DONOR IN VERO CELLS.

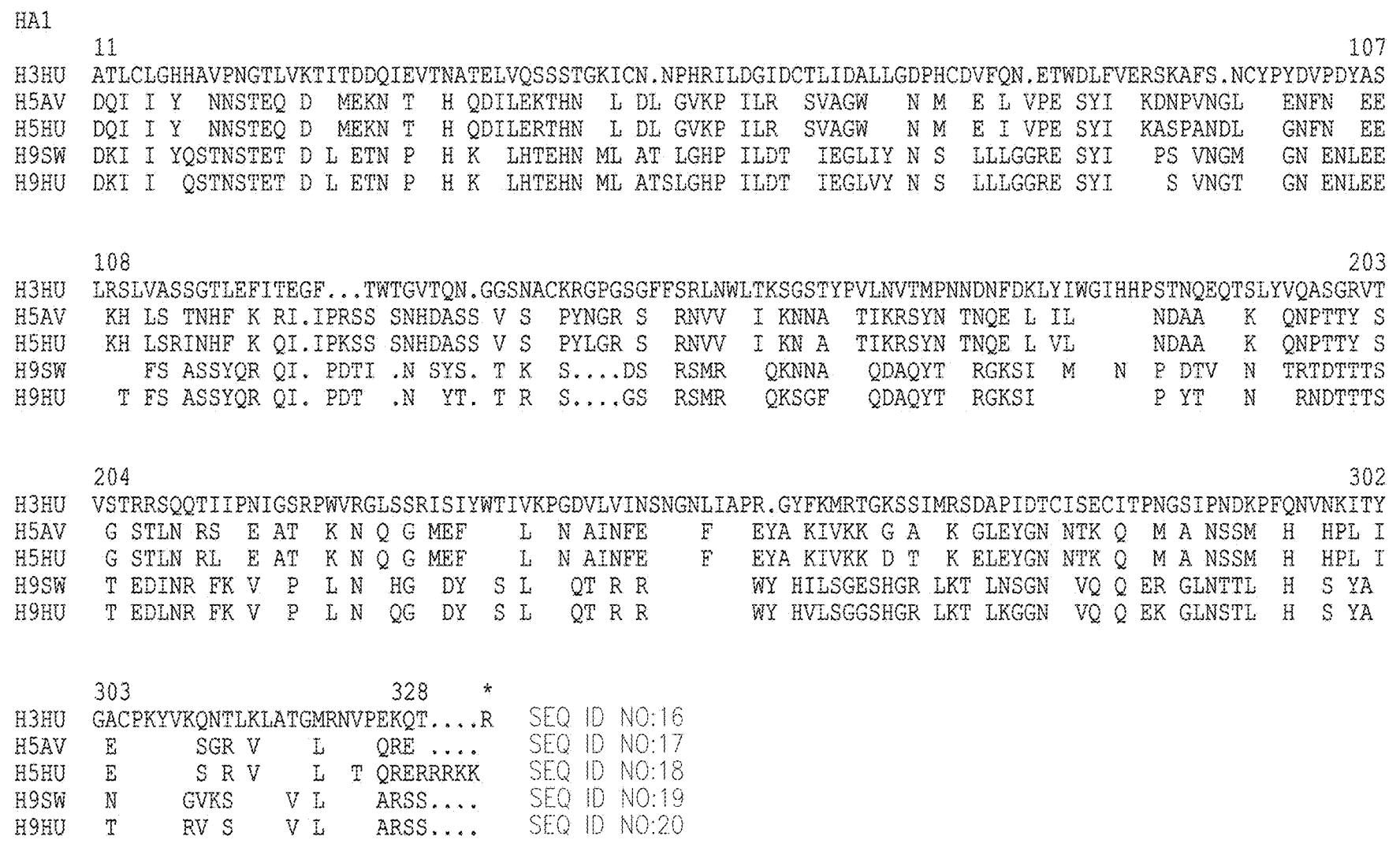

```
HA1
      11                                                                                           107
H3HU  ATLCLGHHAVPNGTLVKTITDDQIEVTNATELVQSSSTGKICN.NPHRILDGIDCTLIDALLGDPHCDVFQN.ETWDLFVERSKAFS.NCYPYDVPDYAS
H5AV  DQI I Y  NNSTEQ D  MEKN T  H QDILEKTHN  L DL GVKP ILR  SVAGW   N M  E L VPE SYI  KDNPVNGL   ENFN  EE
H5HU  DQI I Y  NNSTEQ D  MEKN T  H QDILERTHN  L DL GVKP ILR  SVAGW   N M  E I VPE SYI  KASPANDL   GNFN  EE
H9SW  DKI I YQSTNSTET D L ETN P  H K  LHTEHN ML AT LGHP ILDT  IEGLIY N S  LLLGGRE SYI   PS VNGM   GN ENLEE
H9HU  DKI I  QSTNSTET D L ETN P  H K  LHTEHN ML ATSLGHP ILDT  IEGLVY N S  LLLGGRE SYI    S VNGT   GN ENLEE

      108                                                                                          203
H3HU  LRSLVASSGTLEFITEGF...TWTGVTQN.GGSNACKRGPGSGFFSRLNWLTKSGSTYPVLNVTMPNNDNFDKLYIWGIHHPSTNQEQTSLYVQASGRVT
H5AV   KH LS TNHF K RI.IPRSS SNHDASS V S  PYNGR S  RNVV  I KNNA  TIKRSYN TNQE L IL      NDAA   K  QNPTTY S
H5HU   KH LSRINHF K QI.IPKSS SNHDASS V S  PYLGR S  RNVV  I KN A  TIKRSYN TNQE L VL      NDAA   K  QNPTTY S
H9SW     FS ASSYQR QI. PDTI .N SYS. T K  S....DS  RSMR   QKNNA   QDAQYT  RGKSI  M   N  P DTV   N  TRTDTTTS
H9HU    T FS ASSYQR QI. PDT  .N  YT. T R  S....GS  RSMR   QKSGF   QDAQYT  RGKSI         P YT   N   RNDTTTS

      204                                                                                          302
H3HU  VSTRRSQQTIIPNIGSRPWVRGLSSRISIYWTIVKPGDVLVINSNGNLIAPR.GYFKMRTGKSSIMRSDAPIDTCISECITPNGSIPNDKPFQNVNKITY
H5AV   G STLN RS   E AT   K N Q G MEF    L  N AINFE    F   EYA KIVKK G A  K GLEYGN NTK Q  M A NSSM  H  HPL I
H5HU   G STLN RL   E AT   K N Q G MEF    L  N AINFE    F   EYA KIVKK D T  K ELEYGN NTK Q  M A NSSM  H  HPL I
H9SW   T EDINR FK V  P  L N  HG  DY  S L   QT R R         WY HILSGESHGR LKT LNSGN  VQ Q ER GLNTTL  H  S YA
H9HU   T EDLNR FK V  P  L N  QG  DY  S L   QT R R         WY HVLSGGSHGR LKT LKGGN  VQ Q EK GLNSTL  H  S YA

      303                      328    *
H3HU  GACPKYVKQNTLKLATGMRNVPEKQT....R   SEQ ID NO:16
H5AV   E       SGR V    L    QRE ....   SEQ ID NO:17
H5HU   E        S R V    L  T QRERRRKK   SEQ ID NO:18
H9SW   N      GVKS    V L    ARSS....   SEQ ID NO:19
H9HU   T      RV S    V L    ARSS....   SEQ ID NO:20
```

Fig. 12A

```
HA2
      1                                                                                                 100
H3HU  GLFGAIAGFIENGWEGMIDGWYGFRHQNSEGTGQAADLKSTQAAIDQINGKLNRVIEKTNEKFHQIEKEFSEVEGRIQDLEKYVEDTKIDLWSYNAELLV
H5AV             G  Q          H S EQ S Y   KE   K   GTTN V S  D M TQ EA G   NNL R  EN N KM  GFL V T
H5HU             G  Q          H S EQ S Y   KE   K   G TN V S  N M TQ EA GR  NNL R  EN N KM  GFL V T
H9SW             G  P L A      Q S DQ V M   RD   K   K TS V N  D M KQ GI DH      T LNMINNK D QIQ I T
H9HU             G  P L A      Q S DQ V M   RD   K   K TS V N  D M KQ EI DH      T LNMINNK D QIQ V A

      101                                                                                               199
H3HU  ALENQHTIDLTDSEMNKLFEKTRRQLRENAEEMGNGCFKIYHKCDNACIESIRNGTYDHDVYRDEALNNRFQIKGVELKSGYKDWILWI.SFAISCFLLC
H5AV  LM  ER L FH  NVKN  D V L   D  K L     EF      E M    K     YPQ SE  RL  EE S  K E MGIYQ  S Y TVA SLA A
H5HU  LM  ER L FH  NVKN  D V L   D  K L     EF      E M    K     YPQ SE  RL  EE S  K E MGTYQ  S Y TVA SLA A
H9SW  L     K L EH ANV N  N VK A GS  M D K   EL     DQ M T       NRRK KE SKLE QK E  K E EGTYK  T Y TVA SLVIA
H9HU  L     K L EH ANV N  N VK A GS  M D K   EL     DQ M T       NRRK  E SRLE QK E -------------------------

      200                 221
H3HU  VVLLGFIMWACQRGNIRCNICI   SEQ ID NO:23
H5AV   MIA LSL M SN SLQ R     SEQ ID NO:24
H5HU   MVA LSL M SN SLQ R     SEQ ID NO:25
H9SW  MGFAA LF  MS----------  SEQ ID NO:26
H9HU  ----------------------  SEQ ID NO:27
```

*Fig. 12A CONT'D*

```
  1 MKAILVVLLY TFATANADTL CIGYHANNST DTVDTVLEKN VTVTHSVNLL EDKHNGKLCK
 61 LRGVAPLHLG KCNIAGWILG NPECESLSTA SSWSYIVETP SSDNGTCYPG DFIDYEELRE
121 QLSSVSSFER FEIFPKTSSW PNHDSNKGVT AACPHAGAKS FYKNLIWLVK KGNSYPKLSK
181 SYINDKGKEV LVLWGIHHPS TSADQQSLYQ NADAYVFVGS SRYSKKFKPE IAIRPKVRDQ
241 EGRMNYYWTL VEPGDKITFE ATGNLVVPRY AFAMERNAGS GIIISDTPVH DCNTTCQTPK
301 GAINTSLPFQ NIHPITIGKC PKYVKSTKLR LATGLRNIPS IQSRGLFGAI AGFIEGGWTG
361 MVDGWYGYHH QNEQGSGYAA DLKSTQNAID EITNKVNSVI EKMNTQFTAV GKEFNHLEKR
421 IENLNKKVDD GFLDIWTYNA ELLVLLENER TLDYHDSNVK NLYEKVRSQL KNNAKEIGNG
481 CFEFYHKCDN TCMESVKNGT YDYPKYSEEA KLNREEIDGV KLESTRIYQI LAIYSTVASS
541 LVLVVSLGAI SFWMCSNGSL QCRICI SEQ ID NO:21
```

Fig. 12B

A/Kawasaki/173/2001 (H1N1)
GLFGAIAGFIEGGWTGMVDGWYGYHHQNEQGSGYAADQKSTQNAINGITNKVNSVIEKMNTQFTAVG
KEFNKLERRMENLNKKVDDGFLDIWTYNAELLVLLENERTLDFHDSNVKDLYEKVKSQLKNNAKEIGNGCF
EFYHKCNNECMESVKNGTYDYPKYSEESKLNREKIDGVKLESMGVYQILAIYSTVASSLVLLVSLGAISFWM
CSNGSLQCRICI
SEQ ID NO:28

A/Kawasaki/UTK-4/2009 (H1N1)
GLFGAIAGFIEGGWTGMVDGWYGYHHQNEQGSGYAADQKSTQNAINGITNKVNSVIEKMNTQFTAVG
KEFNKLERRMENLNKKVDDGFIDIWTYNAELLVLLENERTLDFHDSNVKDLYEKVKSQLKNNAKEIGNGCFE
FYHKCNDECMESVKNGTYDYPKYSEESKLNREKIDGVKLESMGVYQILAIYSTVASSLVLLVSLGAISFWMC
SNGSLQCRICI
SEQ ID NO:29

A/Yokohama/2017/2003 (H3N2)
GIFGAIAGFIENGWEGMVDGWYGFRHQNSEGTGQAADLKSTQAAINQINGKLNRLIGKTNEKFHQIEKEF
SEVEGRIQDLEKYVEDTKIDLWSYNAELLVALENQHTIDLTDSEMDKLFERTKKQLRENAEDMGNGCFKIYH
KCDNACIESIRNGTYDHDVYRDEALNNRFQIKGVELKSGYKDWILWISFAISCFLLCVALLGFIMWACQKGN
IRCNICI
SEQ ID NO:30

Fig. 13

HIGH TITER RECOMBINANT INFLUENZA VIRUSES WITH ENHANCED REPLICATION IN VERO CELLS

CROSS-REFERENCE TO RELATED APPLICATIONS

This application is a continuation of U.S. patent application Ser. No. 14/816,807, filed Aug. 3, 2015, which is a continuation of U.S. patent application Ser. No. 12/912,411, filed Oct. 26, 2010, which claims the benefit of the filing date of U.S. application Ser. No. 61/254,795, filed on Oct. 26, 2009, the disclosure of which is incorporated by reference herein.

STATEMENT OF GOVERNMENT RIGHTS

This invention was made with government support Under AI069274 awarded by the National Institutes of Health. The government has certain rights in the invention.

BACKGROUND

Influenza is a major respiratory disease in some mammals including horses and is responsible for substantial morbidity and economic losses each year. In addition, influenza virus infections can cause severe systemic disease in some avian species, leading to death. The segmented nature of the influenza virus genome allows for reassortment of segments during virus replication in cells infected with two or more influenza viruses. The reassortment of segments, combined with genetic mutation and drift, can give rise to a myriad of divergent strains of influenza virus over time. The new strains exhibit antigenic variation in their hemagglutinin (HA) and/or neuraminidase (NA) proteins, and in particular the gene coding for the HA protein has a high rate of variability. The predominant current practice for the prevention of flu is vaccination. Most commonly, whole virus vaccines are used. As the influenza HA protein is the major target antigen for the protective immune responses of a host to the virus and is highly variable, the isolation of influenza virus and the identification and characterization of the HA antigen in viruses associated with recent outbreaks is important for vaccine production. Based on prevalence and prediction, a vaccine is designed to stimulate a protective immune response against the predominant and expected influenza virus strains (Park et al., 2004).

There are three general types of influenza viruses, Type A, Type B and Type C, which are defined by the absence of serological crossreactivity between their internal proteins. Influenza Type A viruses are further classified into subtypes based on antigenic and genetic differences of their glycoproteins, the HA and NA proteins. All the known HA and NA subtypes (H1 to H15 and N1 to N9) have been isolated from aquatic birds, which are though to act as a natural reservoir for influenza. The H1N1 "swine flu" virus has recently been declared to be a pandemic. While this virus may be less virulent than some circulating influenza viruses in certain populations, it is ubiquitous and has become the subject of significant public health efforts. Unfortunately, this virus appears to be less amenable than other viruses to high titer productions which may lead to challenges in vacine manufacture.

SUMMARY OF THE INVENTION

The invention provides isolated recombinant, e.g., reassortant, influenza viruses with selected amino acid residues at specified positions in HA2, NA and/or PB2. In one embodiment, the recombinant reassortant influenza virus has an amino acid residue at position 117 in HA2 (position is based on H1 HA2 numbering; for example, position 117 in H1 HA2 corresponds to position 116 in H3 HA2) that results in enhanced growth in Vero cells relative to a corresponding virus with, for instance, an asparagine at position 117 in HA2, wherein the numbering for HA2 residues is that for H1 HA2. In one embodiment, the recombinant influenza virus has an amino acid residue at position 117 in HA2 that results in fusion of the virus with membranes in endosomes, e.g., late endosomes, at a higher pH relative to a corresponding virus with, for instance, an asparagine at position 117 in HA2, wherein the numbering for HA2 residues is that for H1 HA2. In one embodiment, the invention provides an isolated recombinant reassortant influenza virus having six "internal" gene segments from a vaccine influenza virus, a NA gene segment selected from a first influenza virus isolate, and a HA gene segment selected to encode an aspartic acid or glutamic acid at position 117 in HA2, wherein the numbering for HA2 residues is that for H1 HA2. For example, the NA and HA gene segments may be from a strain for a seasonal flu vaccine or from a pandemic strain, and in one embodiment, the HA2 sequence in the HA gene segment is mutated to encode an aspartic acid or glutamic acid at position 117 in HA2, wherein the numbering for HA2 residues is that for H1 HA2.

As described herein, an influenza virus isolate useful as a vaccine virus (A/Puerto Rico/8/34 (PR8) to carry heterologous gene segments for NA and/or HA was serially passaged in Vero cells to obtain virus with enhanced replication in those cells. In one embodiment, viruses obtained after serial passage which have enhanced replication, have titers that are at least 2, 3, 4 or 5 logs higher than viruses that were not serially passaged. In one embodiment, viruses obtained after serial passage had substitutions in three gene segments, NA, HA and PB2, relative to the parent virus. It was determined that the substitution in HA2 was primarily associated with the enhanced growth phenotype. PR8 virus with HA2 N117D had at least a three log enhancement in titer in Vero cells. The HA2 N117D mutant fused cells at a higher pH than did wild-type HA. Three different recombinant (6:2 mutant reassortant) influenza viruses were prepared that had the same PR8 "internal" genes (i.e., those other than the HA and NA genes), and the NA and HA from a single isolate, and where the residue at position 117 (or position 116 in the H3 reassortant) in HA2 was altered to aspartic acid. All of the 6:2 mutant reassortants showed enhanced growth in Vero cells relative to the corresponding parent 6:2 reassortant. Thus, for vaccine viruses that are to be grown or passaged in cells in culture, e.g., Vero cells, replacement of the residue at position 117 in HA2, wherein the numbering for HA2 residues is that for H1 HA2, e.g., by mutation, or selection of a HA gene segment with a residue that confers enhanced growth of the virus in cultured cells, can result in significantly higher viral titers. Thus, the invention provides a method to select for influenza viruses with enhanced replication in cell culture. The method includes providing cells suitable for influenza vaccine production; serially culturing one or more influenza virus isolates in the cells; and isolating serially cultured virus with enhanced growth relative to the one or more isolates prior to serial culture. In one embodiment, the cells are rodent or primate, e.g., human, cells. Also provided is a method to identify a HA2 that confers altered growth of a recombinant influenza virus. The method includes introducing one or more substitutions in influenza virus HA2 into a HA gene segment to yield a mutant HA gene segment; and identifying whether the mutant HA gene segment, when present in a replication competent recombinant influenza virus, results in enhanced replication of the recombinant influenza virus in a cell relative to a corresponding replication competent influenza virus without the one or more substitutions in HA2. In one embodiment, at least one substitution is at position 117 in HA2, wherein the numbering for HA2 residues is that for H1 HA2, e.g., the at least one substitution is to aspartic acid or glutamic acid. In one embodiment, the cells are rodent or primate cells. In one embodiment, the one or more substitutions are to an amino acid residue with an acidic side chain.

In one embodiment, the influenza virus of the invention is a recombinant influenza virus having a mutant HA2 protein with at least one substitution that replaces an amino acid residue with an aliphatic side chain, amide-containing side chain, basic side chain, or sulfur containing side chain with a residue with an aromatic side chain or acidic side chain (a nonconservative substitution), e.g., at position 117 in HA2, wherein the numbering for HA2 residues is that for H1 HA2. In one embodiment, the influenza virus is a recombinant influenza virus having a HA2 protein with a residue with an aromatic side chain or acidic side chain at position 117 in HA2, wherein the numbering for HA2 residues is that for H1 HA2. In one embodiment, the recombinant influenza virus has a mutant HA2 protein with at least one substitution that replaces a neutral or positively charged residue with a polar or negatively charged residue, e.g., at position 117 in HA2, wherein the numbering for HA2 residues is that for H1 HA2. In one embodiment, the influenza virus is a recombinant influenza virus having a HA2 protein with a residue with a polar or negatively charged residue at position 117 in HA2, wherein the numbering for HA2 residues is that for H1 HA2. The presence of the residue with the aromatic side chain or acidic side chain, or the polar or negatively charged residue, at position 117 in HA2 may alter the efficiency or rate of conformational change of HA or pH dependent membrane fusion. In one embodiment, the recombinant reassortant influenza virus comprises a HA gene segment selected to encode an aspartic acid or glutamic acid at position 117 in HA2, wherein recombinant virus has enhanced replication in Vero cells relative to a corresponding virus that does not have aspartic acid or glutamic acid at position 117 in HA2, e.g., where the corresponding virus has an alanine, asparagine, arginine or lysine at position 117 in HA2, wherein the numbering for HA2 residues is that for H1 HA2. In one embodiment, the recombinant virus has a NA gene segment with a tyrosine at position 255, wherein the numbering for NA residues is that for N1.

In one embodiment, the invention provides isolated influenza type A virus with a characteristic residue or substitution at position 117 of HA2, e.g., the residue at position 117 of HA2 is not asparagine, alanine, arginine or lysine, wherein the numbering for HA2 residues is that for H1 HA2. In one embodiment, the isolated influenza type A virus of the invention with a characteristic residue or substitution at position 117 of HA2, has an HA2 amino acid sequence with at least 80%, e.g., 90%, 92%, 95%, 97% or 99%, including any integer between 80 and 99, contiguous amino acid sequence identity to a polypeptide encoded by one of SEQ ID NOs:16-20 or 22. In one embodiment, the isolated influenza type A virus of the invention with a characteristic residue or substitution at position 117 of HA2, has an HA1 from any one of subtypes 1-15 of HA. In one embodiment, an isolated influenza A virus of the invention has a nonconservative substitution at residue 117 of HA2, e.g., an asparagine to an asparatic acid substitution, wherein the numbering for HA2 residues is that for H1 HA2. In one embodiment, the isolated influenza virus of the invention has an aspartic acid or glutamic acid at position 117 of HA2, wherein the numbering for HA2 residues is that for H1 HA2. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: threonine-valine-leucine-isoleucine-alanine; phenylalanine-tyrosine; lysine-arginine; alanine-valine; glutamic-aspartic; and asparagine-glutamine.

In one embodiment, a mutation is introduced into a HA gene segment of an influenza virus isolate, e.g., via recombinant DNA techniques including site-specific mutagenesis or replacing a portion of the HA coding sequence that includes residue 117 of HA2 with a portion that includes the characteristic residue(s), wherein the numbering for HA2 residues is that for H1 HA2.

In another embodiment, a HA gene segment with a residue that confers enhanced replication in Vero cells is combined with a compatible NA segment, and internal gene segments of an influenza vaccine virus. In one embodiment, the substitution(s) in the HA2 protein, or the characteristic residue in the HA2 protein, that results in the enhanced replication, is/are at or within about 1 to 10 residues, or any integer in between, for instance, at or within 1 to 5, residues, of residue 117 of the HA2 protein of influenza A virus, wherein the numbering for HA2 residues is that for H1 HA2. In one embodiment, a NA protein has at least one substitution, or has the characteristic residue discussed herein, such as one that results in enhanced replication, at or within about 1 to 10 residues, or any integer in between, e.g., at or within 1 to 5 residues of the codon for residue 255 of the NA protein of influenza A virus, wherein the numbering for NA residues is that for N1.

The invention provides a plurality of influenza virus vectors of the invention, e.g., those useful to prepare reassortant viruses including 6:1:1 reassortants, 6:2 reassortants and 7:1 reassortants. A 6:1:1 reassortant within the scope of the present invention is an influenza virus with 6 internal gene segments from a vaccine virus, a NA gene segment from a different (second) viral isolate, and a HA gene segment with a characteristic residue or substitution at position 117 of HA2 as described herein, where the HA gene segment is from a different viral source than the vaccine virus or the first viral isolate; a 6:2 reassortant within the scope of the present invention is an influenza virus with 6 internal gene segments from a vaccine virus, and a NA gene segment and a HA gene segment from a different (second) viral isolate, where the HA gene segment has the characteristic residue or a substitution at position 117 of HA2 as described herein; and a 7:1 reassortant within the scope of the present invention is an influenza virus with 6 internal gene segments and a NA gene segment from a vaccine virus, and a HA gene segment with a characteristic residue or substitution at position 117 of HA2 as described herein, where the HA gene segment is from a different viral source than the vaccine virus, or an influenza virus with 6 internal gene segments and a HA gene segment with the characteristic residue or substitution at position 117 of HA2 as described herein, and a NA gene segment is from a different viral source than the vaccine virus.

In one embodiment of the invention, the plurality includes vectors for vRNA production selected from a vector comprising a promoter operably linked to an influenza virus PA DNA linked to a transcription termination sequence, a vector comprising a promoter operably linked to an influenza virus PB1 DNA linked to a transcription termination sequence, a vector comprising a promoter operably linked to an influenza virus PB2 DNA linked to a transcription termination sequence, a vector comprising a promoter operably linked to an influenza virus HA DNA linked to a transcription termination sequence, a vector comprising a promoter operably linked to an influenza virus NP DNA linked to a transcription termination sequence, a vector comprising a promoter operably linked to an influenza virus NA DNA linked to a transcription termination sequence, a vector comprising a promoter operably linked to an influenza virus M DNA linked to a transcription termination sequence, and a vector comprising a operably linked to an influenza virus NS DNA linked to a transcription termination sequence. In one embodiment, the DNAs for vRNA production of PB1, PB2, PA, NP, M, and NS, have sequences from an influenza virus that replicates to high titers in cultured mammalian cells such as Vero cells or PER.C6® cells and also optionally embryonated eggs, and/or from a vaccine virus, e.g., one that does not cause significant disease in humans. The DNA for vRNA production of NA may be from any NA, e.g., any of N1-N9, and the DNA for vRNA production of HA may be from any HA, e.g., H1-H16. In one embodiment, the DNAs for vRNA production may be for an influenza B or C virus. For example, the DNAs for vRNA production include influenza B virus PA, PB1, PB2, NP, NS, and M or influenza B virus PA. PB1, PB2, NP, NS, M, and NA, wherein the vRNA for HA has a HA2 with a characteristic amino acid at position 117 in HA2, wherein the numbering for HA2 residues is that for H1 HA2. The DNAs for vRNA production of NA and HA may be from different strains or isolates (6:1:1 reassortants) or from the same strain or isolate (6:2 reassortants), or the NA may be from the same strain or isolate as that for the internal genes (7:1 reassortant), where the HA2 sequence is selected to result in enhanced replication in Vero cells relative to a corresponding virus with, for example, an asparagine at position 117 in HA2, wherein the numbering for HA2 residues is that for H1 HA2. The plurality also includes vectors for mRNA production selected from a vector encoding influenza virus PA, a vector encoding influenza virus PB1, a vector encoding influenza virus PB2, and a vector encoding influenza virus NP, and optionally one or more vectors encoding NP. NS, M, e.g., M1 and M2, HA or NA. The vectors encoding viral proteins may further include a transcription termination sequence.

Viruses that may provide the internal genes for reassortants within the scope of the invention include viruses that have high titers in Vero cells, e.g., titers of at least about $10^5$ PFU/mL, e.g., at least $10^6$ PFU/mL, $10^7$ PFU/mL or $10^8$ PFU/mL; high titers in embryonated eggs, e.g., titers of at least about $10^7$ $EID_{50}$/mL, e.g., at least $10^8$ $EID_{50}$/mL, $10^9$ $EID_{50}$/mL or $10^{10}$ $EID_{50}$/mL; high titers in MDCK cells, e.g., titers of at least about $10^7$ PFU/mL, e.g., at least $10^8$ PFU/mL, or high titers in two of more of those host cells.

In one embodiment, the titers of the reassortant viruses of the invention in cells such as Vero cells may be over 1 log, 2 logs, 3 logs, or greater, than titers of the corresponding virus without a HA2 substitution or that lacks the selected residue at position 117 of HA2, wherein the numbering for HA2 residues is that for H1 HA2.

Other reassortants with internal genes from other PR8 isolates or vaccine viruses may be employed in recombinant reassortant viruses of the invention. In particular, 5:1:2 reassortants having PR8(UW) PB1, PB2, PA, NP, and M ("5") and PR8(Cam) NS ("1"); 6:1:1 reassortants having PR8(UW) NA, PB1, PB2, PA, NP, and M ("6") and PR8 (Cam) NS ("1"); and 7:1 reassortants having PR8(UW) PB1. PB2. PA. NP, M, NA, and NS ("7") may be employed.

In one embodiment, the DNAs for the internal genes for PB1. PB2, PA, NP. M, and NS encode proteins with substantially the same activity as a corresponding polypeptide encoded by one of SEQ ID Nos:1-6 or 10-15. As used herein, "substantially the same activity" includes an activity that is about 0.1%, 1%, 10%, 30%, 50%, 90%, e.g., up to 100% or more, or detectable protein level that is about 80%, 90% or more, the activity or protein level, respectively, of the corresponding full-length polypeptide. In one embodiment, the nucleic acid a sequence encoding a polypeptide which is substantially the same as, e.g., having at least 80%, e.g., 90%, 92%, 95%, 97% or 99%, including any integer between 80 and 99, contiguous amino acid sequence identity to, a polypeptide encoded by one of SEQ ID NOs:1-6 or 10-15. In one embodiment, the isolated and/or purified nucleic acid molecule comprises a nucleotide sequence which is substantially the same as, e.g., having at least 50%, e.g., 60%, 70%, 80% or 90%, including any integer between 50 and 100, or more contiguous nucleic acid sequence identity to one of SEQ ID NOs:1-6 or 10-15 and, in one embodiment, also encodes a polypeptide having at least 80%, e.g., 90%, 92%, 95%, 97% or 99%, including any integer between 80 and 99, contiguous amino acid sequence identity to a polypeptide encoded by one of SEQ ID NOs:1-6 or 10-15. In one embodiment, the influenza virus polypeptide has one or more, for instance, 2, 5, 10, 15, 20 or more, conservative amino acids substitutions, e.g., conservative substitutions of up to 10% or 20% of the residues, relative to a polypeptide encoded by one of SEQ ID NOs:1-6 or 10-15. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine and tryptophan; a group of amino acids having basic side chains is lysine, arginine and histidine; and a group of amino acids having sulfur-containing side chain is cysteine and methionine. In one embodiment, conservative amino acid substitution groups are: valine-leucine-isoleucine; phenylalanine-tyrosine; lysine-arginine; alanine-valine; glutamic-aspartic; and asparagine-glutamine. In one embodiment, the influenza virus polypeptide has one or more, for instance, 2, 3 or 4, nonconservative amino acid substitutions, relative to a polypeptide encoded by one of SEQ ID NOs:1-6 or 10-15.

The invention thus includes the use of isolated and purified vectors or plasmids, which express or encode influenza virus proteins, or express or encode influenza vRNA, both native and recombinant vRNA. The vectors comprise influenza cDNA, e.g., influenza A (e.g., any influenza A gene including any of the 16 HA or 9 NA subtypes), B or C DNA (see Fields *Virology* (Fields et al. (eds.), Lippincott. Williams and Wickens (2006), which is specifically incorporated by reference herein). Any suitable promoter or transcription termination sequence may be employed to express a protein or peptide, e.g., a viral protein or peptide, a protein or peptide of a nonviral pathogen, or a therapeutic protein or peptide.

A composition or plurality of vectors of the invention may also comprise a heterologous gene or open reading frame of interest, e.g., a foreign gene encoding an immunogenic peptide or protein useful as a vaccine or in gene replacement, fro instance imay encode an epitope useful in a cancer therapy or vaccine, or a peptide or polypeptide useful in gene therapy. When preparing virus, the vector or plasmid comprising the gene or cDNA of interest may substitute for a vector or plasmid for an influenza viral gene or may be in addition to vectors or plasmids for all influenza viral genes. Thus, another embodiment of the invention comprises a composition or plurality of vectors as described above in which one of the vectors is replaced with, or further comprises, 5' influenza virus sequences optionally including 5' influenza virus coding sequences or a portion thereof, linked to a desired nucleic acid sequence, e.g., a desired cDNA, linked to 3' influenza virus sequences optionally including 3' influenza virus coding sequences or a portion thereof. In one embodiment, the desired nucleic acid sequence such as a cDNA is in an antisense (antigenomic) orientation. The introduction of such a vector in conjunction with the other vectors described above to a host cell permissive for influenza virus replication results in recombinant virus comprising vRNA corresponding to the heterologous sequences of the vector.

The promoter in a vector for vRNA production may be a RNA polymerase I promoter, a RNA polymerase II promoter, a RNA polymerase III promoter, a T7 promoter, or a T3 promoter, and optionally the vector comprises a transcription termination sequence such as a RNA polymerase I transcription termination sequence, a RNA polymerase II transcription termination sequence, a RNA polymerase III transcription termination sequence, or a ribozyme. Ribozymes within the scope of the invention include, but are not limited to, tetrahymena ribozymes, RNase P, hammerhead ribozymes, hairpin ribozymes, hepatitis ribozyme, as well as synthetic ribozymes. In one embodiment, the RNA polymerase I promoter is a human RNA polymerase I promoter.

The promoter or transcription termination sequence in a vRNA or virus protein expression vector may be the same or different relative to the promoter or any other vector. In one embodiment, the vector or plasmid which expresses influenza vRNA comprises a promoter suitable for expression in at least one particular host cell, e.g., avian or mammalian host cells such as canine, feline, equine, bovine, ovine, or primate cells including human cells, or for expression in more than one host.

In one embodiment, at least one vector for vRNA comprises a RNA polymerase II promoter linked to a ribozyme sequence linked to viral coding sequences linked to another ribozyme sequences, optionally linked to a RNA polymerase II transcription termination sequence. In one embodiment, at least 2, e.g., 3, 4, 5, 6, 7 or 8, vectors for vRNA production comprise a RNA polymerase II promoter, a first ribozyme sequence, which is 5' to a sequence corresponding to viral sequences including viral coding sequences, which is 5' to a second ribozyme sequence, which is 5' to a transcription termination sequence. Each RNA polymerase II promoter in each vRNA vector may be the same or different as the RNA polymerase II promoter in any other vRNA vector. Similarly, each ribozyme sequence in each vRNA vector may be the same or different as the ribozyme sequences in any other vRNA vector. In one embodiment, the ribozyme sequences in a single vector are not the same.

In one embodiment, the invention provides a plurality of influenza virus vectors for a reassortant, comprising a vector for vRNA production comprising a promoter operably linked to an influenza virus PA DNA linked to a transcription termination sequence, a vector for vRNA production comprising a promoter operably linked to an influenza virus PB1 DNA linked to a transcription termination sequence, a vector for vRNA production comprising a promoter operably linked to an influenza virus PB2 DNA linked to a transcription termination sequence, a vector for vRNA production comprising a promoter operably linked to an influenza virus HA DNA linked to a transcription termination sequence, a vector for vRNA production comprising a promoter operably linked to an influenza virus NP DNA linked to a transcription termination sequence, a vector for vRNA production comprising a promoter operably linked to an influenza virus NA DNA linked to a transcription termination sequence, a vector for vRNA production comprising a promoter operably linked to an influenza virus M DNA linked to a transcription termination sequence, and a vector for vRNA production comprising a promoter operably linked to an influenza virus NS cDNA linked to a transcription termination sequence, wherein the DNAs for PB1, PB2, PA, NP. NS, and M from one or more influenza vaccine seed viruses, wherein the DNA for NA has sequences for a heterologous NA, and wherein the DNA for HA selected to encode an aspartic acid or glutamic acid at position 117 in HA2, wherein the numbering for HA2 residues is that for H1 HA2; and a vector for mRNA production comprising a promoter operably linked to a DNA segment encoding influenza virus PA, a vector for mRNA production comprising a promoter operably linked to a DNA segment encoding influenza virus PB1, a vector for mRNA production comprising a promoter operably linked to a DNA segment encoding influenza virus PB2, and a vector for mRNA production comprising a promoter operably linked to a DNA segment encoding influenza virus NP, and optionally a vector for mRNA production comprising a promoter operably linked to a DNA segment encoding influenza virus HA, a vector for mRNA production comprising a promoter operably linked to a DNA segment encoding influenza virus NA, a vector for mRNA production comprising a promoter operably linked to a DNA segment encoding influenza virus M1, a vector for mRNA production comprising a promoter operably linked to a DNA segment encoding influenza virus M2, or a vector for mRNA production comprising a promoter operably linked to a DNA segment encoding influenza virus NS2. In one embodiment, at least one vector comprises sequences corresponding to those encoding PB1, PB2, PA, NP. M, or NS, or a portion thereof, having substantially the same activity as a corresponding polypeptide encoded by one of SEQ ID NOs:1-6 or 10-15, e.g., a sequence encoding a polypeptide with at least 80%, e.g., 85%, 90%, 92%, 95%, 98%, 99% or 100%, including any integer between 80 and 100, amino acid identity to a polypeptide encoded by one of SEQ ID NOs:1-6 or 10-15. Optionally, two vectors may he employed in place of the vector comprising a promoter operably linked to an influenza virus M cDNA linked to a transcription termination sequence, e.g., a vector comprising a promoter operably linked to an influenza virus M1 cDNA linked to a transcription termination sequence and a vector comprising a promoter operably linked to an influenza virus M2 cDNA linked to a transcription termination sequence.

A plurality of the vectors of the invention may be physically linked or each vector may be present on an individual plasmid or other, e.g., linear, nucleic acid delivery vehicle. In one embodiment, each vRNA production vector is on a separate plasmid. In one embodiment, each mRNA production vector is on a separate plasmid.

The invention also provides a method to prepare influenza virus. The method comprises contacting a cell with a plurality of the vectors of the invention, e.g., sequentially or simultaneously, in an amount effective to yield infectious influenza virus. The invention also includes isolating virus from a cell contacted with the plurality of vectors. Thus, the invention further provides isolated virus, as well as a host cell contacted with the plurality of vectors or virus of the invention. In another embodiment, the invention includes contacting the cell with one or more vectors, either vRNA or protein production vectors, prior to other vectors, either vRNA or protein production vectors. In one embodiment, the promoter for vRNA vectors employed in the method is a RNA polymerase I promoter, a RNA polymerase II promoter, a RNA polymerase III promoter, a T3 promoter or a T7 promoter. In one embodiment, the RNA polymerase I promoter is a human RNA polymerase I promoter. In one embodiment, each vRNA vector employed in the method is on a separate plasmid. In one embodiment, the vRNA vectors employed in the method are on one plasmid or on two or three different plasmids. In one embodiment, each mRNA vector employed in the method is on a separate plasmid. In one embodiment, the mRNA vectors for PA, PB1, PB2 and NP employed in the method are on one plasmid or on two or three different plasmids.

In one embodiment, the invention provides a method to select for influenza viruses with enhanced replication in cell culture. The method includes providing cells suitable for influenza vaccine production; serially culturing one or more influenza virus isolates in the cells; and isolating serially cultured virus with enhanced growth relative to the one or more isolates prior to serial culture. In one embodiment, the cells are rodent or primate cells.

Also provided is a method to identify a HA2 that confers altered growth of a recombinant influenza virus. The method includes introducing one or more substitutions in influenza virus HA2 into a HA gene segment to yield a mutant HA gene segment; and identifying whether the mutant HA gene segment, when present in a replication competent recombinant influenza virus, results in enhanced replication of the recombinant influenza virus in a cell relative to a corresponding replication competent influenza virus without the one or more substitutions in HA2. In one embodiment, at least one substitution is at position 117 in HA2, wherein the numbering for HA2 residues is that for H1 HA2, e.g., at least one substitution is to aspartic acid or glutamic acid. In one embodiment, the cell is a rodent or primate cell. In one embodiment, the one or more substitutions are to an amino acid residue with an acidic side chain.

In one embodiment, the invention provides a method to prepare a recombinant influenza virus with a HA gene segment having a mutant HA2. The method includes altering influenza virus HA nucleic acid at position 117 in HA2 to aspartic acid or glutamic acid; and expressing the altered nucleic acid in a cell having vectors for influenza vRNA production and viral protein production in an amount effective to yield recombinant influenza virus with a HA gene segment having the aspartic acid or glutamic acid at position 117 in HA2, wherein the numbering for HA2 residues is that for H1 HA2. In one embodiment, the cell is a mammalian, e.g., a human cell, or avian cell.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors). Thus, a virus for use in medical therapy (e.g., for a vaccine or gene therapy) is provided.

The invention also provides isolated viral polypeptides, and methods of preparing and using recombinant virus of the invention. The methods include administering to a host organism, e.g., a mammal, an effective amount of the influenza virus of the invention, e.g., an inactivated virus preparation, optionally in combination with an adjuvant and/or a carrier, e.g., in an amount effective to prevent or ameliorate infection of an animal such as a mammal by that virus or an antigenically closely related virus. In one embodiment, the virus is administered intramuscularly while in another embodiment, the virus is administered intranasally. In some dosing protocols, all doses may be administered intramuscularly or intranasally, while in others a combination of intramuscular and intranasal administration is employed. The vaccine may further contain other isolates of influenza virus including recombinant influenza virus, other pathogen(s), additional biological agents or microbial components, e.g., to form a multivalent vaccine. In one embodiment, intranasal vaccination, for instance containing with inactivated influenza virus, and a mucosal adjuvant may induce virus-specific IgA and neutralizing antibody in the nasopharynx as well as serum IgG.

The influenza virus of the invention may employed with other anti-virals, e.g., amantadine, rimantadine, and/or neuraminidase inhibitors, e.g., may be administered separately in conjunction with those anti-virals, for instance, administered before, during and/or after.

The invention also provides a method in which the pH of media in which cells suitable for propagating influenza virus are cultured, is altered during virus propagation to allow for enhanced influenza virus replication in those cells. Thus, for cells with late endosomes having a pH that is higher than that in MDCK cells, altering media pH to maintain a higher pH during virus replication over time, may enhance virus production in the absence of a HA2 protein with a characteristic residue, such as aspartic acid, at position 117, wherein the numbering for HA2 residues is that for H1 HA2.

BRIEF DESCRIPTION OF THE FIGURES

FIGS. 1A-C. Nucleotide sequence for PR8(Cambridge) genes (SEQ ID NOs:10-15).

FIG. 3. Comparison of amino acid sequence differences between PR8 and Vero cell-adapted PR8.

FIGS. 12A-B. A) Alignment of HA2 sequences from A/Aichi/2/68; A/Dk/Sing/97; A/HK/486/97; A/Sw/9/98; and A/HongKong/1073/99 (SEQ ID Nos.16-20 and 23-27). B) Amino acid sequence of HA sequence from A/California/08/2009 (SEQ ID NO:21). HA2 sequences correspond to residues 336-566 (SEQ ID NO:22).

FIG. 13. HA2 sequences for A/Kawasaki/173/2001, A/Kawasaki/UKT-4/2009, and A/Yokohama/2017/2003 (SEQ ID NOs:28-30). According to the NCBI database, influenza virus HA2 sequences for H1, H2, H3, H5, H7, and H9 HAs were generally conserved at position 116 or 117 (N116 or N117) (more than 99%).

DETAILED DESCRIPTION OF THE INVENTION

Definitions

Figure 2:
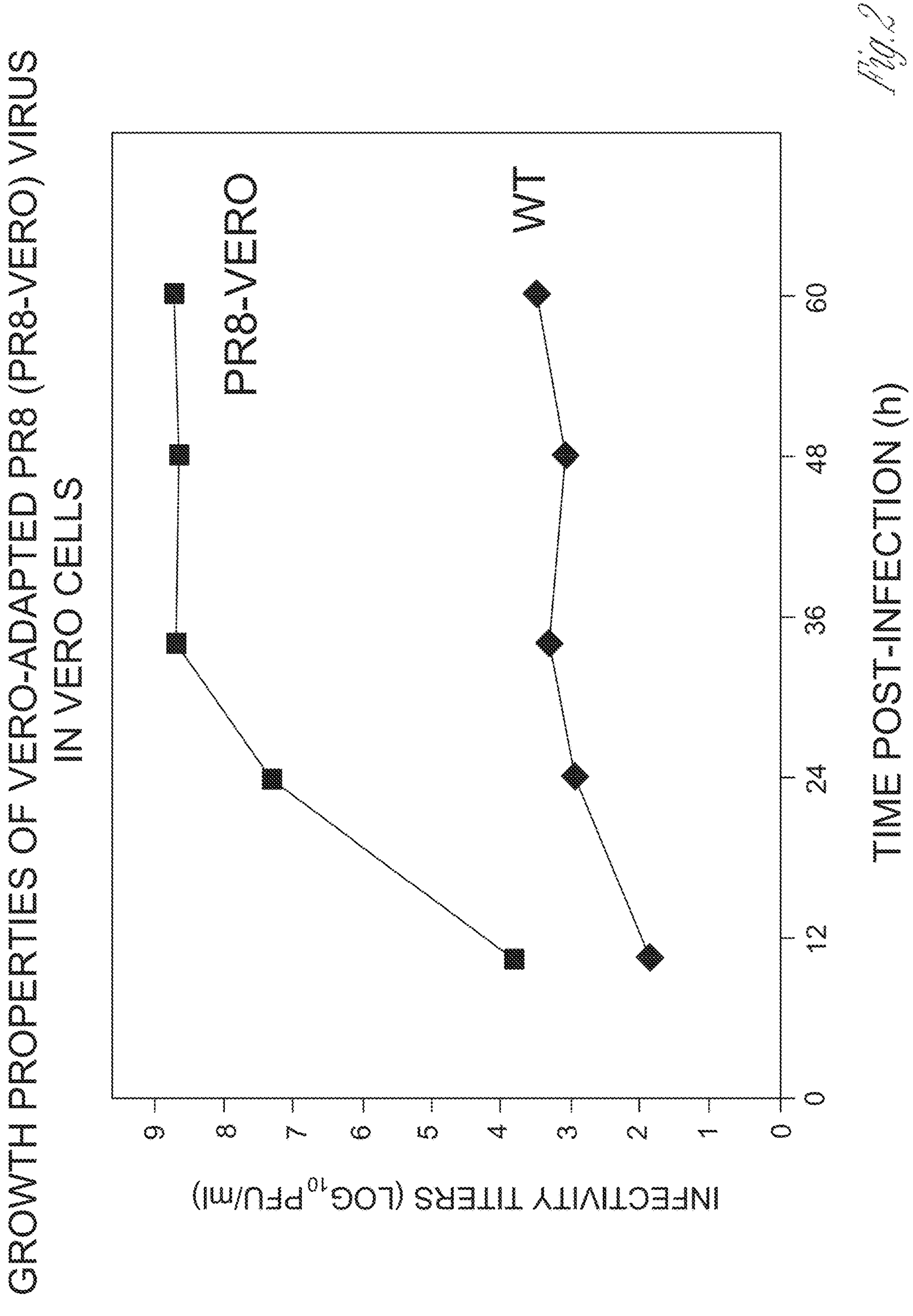
FIG. 2. Growth properties of Vero cell-adapted PR8 virus in Vero cells.

As used herein, the term "isolated" refers to in vitro preparation and/or isolation of a nucleic acid molecule, e.g., vector or plasmid, peptide or polypeptide (protein), or virus of the invention, so that it is not associated with in vivo substances, or is substantially purified from in vitro substances. An isolated virus preparation is generally obtained by in vitro culture and propagation, and/or via passage in eggs, and is substantially free from other infectious agents.

As used herein, "substantially purified" means the object species is the predominant species, e.g., on a molar basis it is more abundant than any other individual species in a composition, and preferably is at least about 80% of the species present, and optionally 90% or greater, e.g., 95%, 98%, 99% or more, of the species present in the composition.

As used herein, "substantially free" means below the level of detection for a particular infectious agent using standard detection methods for that agent.

A "recombinant" virus is one which has been manipulated in vitro, e.g., using recombinant DNA techniques, to introduce changes to the viral genome. Reassortant viruses can be prepared by recombinant or nonrecombinant techniques.

As used herein, the term "recombinant nucleic acid" or "recombinant DNA sequence or segment" refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA "derived" from a source, would be a DNA sequence that is identified as a useful fragment, and which is then chemically synthesized in essentially pure form. An example of such DNA "isolated" from a source would be a useful DNA sequence that is excised or removed from said source by chemical means, e.g., by the use of restriction endonucleases, so that it can be further manipulated, e.g., amplified, for use in the invention, by the methodology of genetic engineering.

As used herein, a "heterologous" influenza virus gene or gene segment is from an influenza virus source that is different than a majority of the other influenza viral genes or gene segments in a recombinant, e.g., reassortant, influenza virus.

The terms "isolated polypeptide", "isolated peptide" or "isolated protein" include a polypeptide, peptide or protein encoded by cDNA or recombinant RNA including one of synthetic origin, or some combination thereof.

The term "recombinant protein" or "recombinant polypeptide" as used herein refers to a protein molecule expressed from a recombinant DNA molecule. In contrast, the term "native protein" is used herein to indicate a protein isolated from a naturally occurring (i.e., a nonrecombinant) source. Molecular biological techniques may be used to produce a recombinant form of a protein with identical properties as compared to the native form of the protein.

Methods of alignment of sequences for comparison are well known in the art. Thus, the determination of percent identity between any two sequences can be accomplished using a mathematical algorithm.

Computer implementations of these mathematical algorithms can be utilized for comparison of sequences to determine sequence identity. Alignments using these programs can be performed using the default parameters. Software for performing BLAST analyses is publicly available through the National Center for Biotechnology Information (http://www.ncbi.nlm.nih.gov/). The algorithm may involve first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm may also perform a statistical analysis of the similarity between two sequences. One measure of similarity provided by the BLAST algorithm may be the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, more preferably less than about 0.01, and most preferably less than about 0.001.

The BLASTN program (for nucleotide sequences) may use as defaults a wordlength (W) of 11, an expectation (E) of 10, a cutoff of 100, M=5. N=−4, and a comparison of both strands. For amino acid sequences, the BLASTP program may use as defaults a wordlength (W) of 3, an expectation (E) of 10, and the BLOSUM62 scoring matrix. See http://www.ncbi.n1m.nih.gov. Alignment may also be performed manually by inspection.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

Influenza Virus Structure and Propagation

Influenza A viruses possess a genome of eight single-stranded negative-sense viral RNAs (vRNAs) that encode at least ten proteins. The influenza virus life cycle begins with binding of the hemagglutinin (HA) to sialic acid-containing receptors on the surface of the host cell, followed by receptor-mediated endocytosis. The low pH in late endosomes triggers a conformational shift in the HA, thereby exposing the N-terminus of the HA2 subunit (the so-called fusion peptide). The fusion peptide initiates the fusion of the viral and endosomal membrane, and the matrix protein (M1) and RNP complexes are released into the cytoplasm. RNPs consist of the nucleoprotein (NP), which encapsidates vRNA, and the viral polymerase complex, which is formed by the PA, PB1, and PB2 proteins. RNPs are transported into the nucleus, where transcription and replication take place. The RNA polymerase complex catalyzes three different reactions: synthesis of an mRNA with a 5' cap and 3' polyA structure, of a full-length complementary RNA (cRNA), and of genomic vRNA using the cRNA as a template. Newly synthesized vRNAs, NP, and polymerase proteins are then assembled into RNPs, exported from the nucleus, and transported to the plasma membrane, where budding of progeny virus particles occurs. The neuraminidase (NA) protein plays a crucial role late in infection by removing sialic acid from sialyloligosaccharides, thus releasing newly assembled virions from the cell surface and preventing the self aggregation of virus particles. Although virus assembly involves protein-protein and protein-vRNA interactions, the nature of these interactions is largely unknown.

Although influenza B and C viruses are structurally and functionally similar to influenza A virus, there are some differences. For example, influenza B virus does not have a M2 protein with ion channel activity but has BM2 and has a gene segment with both NA and NB sequences. Influenza C virus has only seven gene segments.

Cell Lines that can be Used in the Present Invention

Any cell, e.g., any avian or mammalian cell, such as a human, e.g., 293T or PER.C6® cells, or canine, bovine, equine, feline, swine, ovine, rodent, for instance mink, e.g., MvLu1 cells, or hamster, e.g., CHO cells, or non-human primate, e.g., Vero cells, including mutant cells, which supports efficient replication of influenza virus can be employed to isolate and/or propagate influenza viruses. Isolated viruses can be used to prepare a reassortant virus. In one embodiment, host cells for vaccine production are continuous mammalian or avian cell lines or cell strains. A complete characterization of the cells to be used, may be conducted so that appropriate tests for purity of the final product can be included. Data that can be used for the characterization of a cell includes (a) information on its origin, derivation, and passage history; (b) information on its growth and morphological characteristics; (c) results of tests of adventitious agents; (d) distinguishing features, such as biochemical, immunological and cytogenetic patterns which allow the cells to be clearly recognized among other cell lines; and (e) results of tests for tumorigenicity. In one embodiment, the passage level, or population doubling, of the host cell used is as low as possible.

In one embodiment, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity may be tested in cells that are at the same passage level as those used for vaccine production. The virus may be purified by a process that has been shown to give consistent results, before vaccine production (see, e.g., World Health Organization, 1982).

Virus produced by the host cell may be highly purified prior to vaccine or gene therapy formulation. Generally, the purification procedures result in extensive removal of cellular DNA and other cellular compoenents, and adventitious agents. Procedures that extensively degrade or denature DNA may also be used.

Influenza Vaccines

A vaccine of the invention includes an isolated recombinant influenza virus of the invention, and optionally one or more other isolated viruses including other isolated influenza viruses, one or more immunogenic proteins or glycoproteins of one or more isolated influenza viruses or one or more other pathogens, e.g., an immunogenic protein from one or more bacteria, non-influenza viruses, yeast or fungi, or isolated nucleic acid encoding one or more viral proteins (e.g., DNA vaccines) including one or more immunogenic proteins of the isolated influenza virus of the invention. In one embodiment, the influenza viruses of the invention may be vaccine vectors for influenza virus or other pathogens.

A complete virion vaccine may be concentrated by ultrafiltration and then purified by zonal centrifugation or by chromatography. Viruses other than the virus of the invention, such as those included in a multivalent vaccine, may be inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Laver & Webster, 1976); or a nonionic detergent such as that commercialized under the name TRITON X100. The hemagglutinin may also be isolated after treatment of the virions with a protease such as bromelin, and then purified. The subunit vaccine may be combined with an attenuated virus of the invention in a multivalent vaccine.

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done. The split vaccine may be combined with an attenuated virus of the invention in a multivalent vaccine.

Inactivated Vaccines. Inactivated influenza virus vaccines are provided by inactivating replicated virus using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines.

Live Attenuated Virus Vaccines. Live, attenuated influenza virus vaccines, such as those including a recombinant virus of the invention can be used for preventing or treating influenza virus infection. Attenuation may be achieved in a single step by transfer of attenuated genes from an attenuated donor virus to a replicated isolate or reassorted virus according to known methods. Since resistance to influenza A virus is mediated primarily by the development of an immune response to the HA and/or NA glycoproteins, the genes coding for these surface antigens come from the reassorted viruses or clinical isolates. The attenuated genes are derived from an attenuated parent. In this approach, genes that confer attenuation generally do not code for the HA and NA glycoproteins.

Viruses (donor influenza viruses) are available that are capable of reproducibly attenuating influenza viruses, e.g., a cold adapted (ca) donor virus can be used for attenuated vaccine production. Live, attenuated reassortant virus vaccines can be generated by mating the ca donor virus with a virulent replicated virus. Reassortant progeny are then selected at 25° C. (restrictive for replication of virulent virus), in the presence of an appropriate antiserum, which inhibits replication of the viruses bearing the surface antigens of the attenuated ca donor virus. Useful reassortants are: (a) infectious, (b) attenuated for seronegative non-adult mammals and immunologically primed adult mammals, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible mammals both adults and non-adult.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene. Thus, new donor viruses can also be generated bearing attenuating mutations introduced by site-directed mutagenesis, and such new donor viruses can be used in the production of live attenuated reassortants vaccine candidates in a manner analogous to that described above for the ca donor virus. Similarly, other known and suitable attenuated donor strains can be reassorted with influenza virus to obtain attenuated vaccines suitable for use in the vaccination of mammals.

In one embodiment, such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking pathogenicity to the degree that the vaccine causes minimal chance of inducing a serious disease condition in the vaccinated mammal.

The viruses in a multivalent vaccine can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and nucleic acid screening (such as probe hybridization or PCR) to confirm that donor genes encoding the antigenic determinants (e.g., HA or NA genes) are not present in the attenuated viruses.

Pharmaceutical Compositions

Pharmaceutical compositions of the present invention, suitable for inoculation, e.g., nasal, parenteral or oral administration, comprise one or more influenza virus isolates, e.g., one or more attenuated or inactivated influenza viruses, a subunit thereof, isolated protein(s) thereof, and/or isolated nucleic acid encoding one or more proteins thereof, optionally further comprising sterile aqueous or non-aqueous solutions, suspensions, and emulsions. The compositions can further comprise auxiliary agents or excipients, as known in the art. The composition of the invention is generally presented in the form of individual doses (unit doses).

Conventional vaccines generally contain about 0.1 to 200 μg, e.g., 30 to 100 μg, of HA from each of the strains entering into their composition. The vaccine forming the main constituent of the vaccine composition of the invention may comprise a single influenza virus, or a combination of influenza viruses, for example, at least two or three influenza viruses, including one or more reassortant(s).

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized.

Heterogeneity in a vaccine may be provided by mixing replicated influenza viruses for at least two influenza virus strains, such as 2-20 strains or any range or value therein. Vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferonβ, interferon-γ, tumor necrosis factor-alpha, thiosemicarbarzones, methisazone, rifampin, ribavirin, a pyrimidine analog, a purine analog, foscarnet, phosphonoacetic acid, acyclovir, dideoxynucleosides, a protease inhibitor, or ganciclovir.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the invention which are vaccines are provided before any symptom or clinical sign of a pathogen infection becomes manifest. The prophylactic administration of the composition serves to prevent or attenuate any subsequent infection. When provided prophylactically, the gene therapy compositions of the invention, are provided before any symptom or clinical sign of a disease becomes manifest. The prophylactic administration of the composition serves to prevent or attenuate one or more symptoms or clinical signs associated with the disease.

When provided therapeutically, a viral vaccine is provided upon the detection of a symptom or clinical sign of actual infection. The therapeutic administration of the compound(s) serves to attenuate any actual infection. When provided therapeutically, a gene therapy composition is provided upon the detection of a symptom or clinical sign of the disease. The therapeutic administration of the compound(s) serves to attenuate a symptom or clinical sign of that disease.

Thus, a vaccine composition of the present invention may be provided either before the onset of infection (so as to prevent or attenuate an anticipated infection) or after the initiation of an actual infection. Similarly, for gene therapy, the composition may be provided before any symptom or clinical sign of a disorder or disease is manifested or after one or more symptoms are detected.

A composition is said to be "pharmacologically acceptable" if its administration can be tolerated by a recipient mammal. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of mammals. Protection may be limited to mitigating the severity or rapidity of onset of symptoms or clinical signs of the influenza virus infection.

Pharmaceutical Administration

A composition of the present invention may confer resistance to one or more pathogens, e.g., one or more influenza virus strains, by either passive immunization or active immunization. In active immunization, an attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain. A gene therapy composition of the present invention may yield prophylactic or therapeutic levels of the desired gene product by active immunization.

In one embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a clinical sign or condition of the disease, or in the total or partial immunity of the individual to the disease. As used herein, a gene therapy composition is said to prevent or attenuate a disease if its administration results either in the total or partial attenuation (i.e., suppression) of a clinical sign or condition of the disease, or in the total or partial immunity of the individual to the disease.

A composition having at least one influenza virus of the present invention, including one which is attenuated and one or more other isolated viruses, one or more isolated viral proteins thereof, one or more isolated nucleic acid molecules encoding one or more viral proteins thereof, or a combination thereof, may be administered by any means that achieve the intended purposes.

For example, administration of such a composition may be by various parenteral routes such as subcutaneous, intravenous, intradermal, intramuscular, intraperitoneal, intranasal, oral or transdermal routes. Parenteral administration can be accomplished by bolus injection or by gradual perfusion over time.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a composition is one that is sufficient to achieve a desired effect. It is understood that the effective dosage may be dependent upon the species, age, sex, health, and weight of the recipient, kind of concurrent treatment, if any, frequency of treatment, and the nature of the effect wanted. The ranges of effective doses provided below are not intended to limit the invention and represent dose ranges.

The dosage of a live, attenuated or killed virus vaccine for an animal such as a mammalian adult organism may be from about $10^2$-$10^{15}$, e.g., $10^3$-$10^{12}$, plaque forming units (PFU)/kg, or any range or value therein. The dose of inactivated vaccine may range from about 0.1 to 1000, e.g., 30 to 100 μg, of HA protein. However, the dosage should be a safe and effective amount as determined by conventional methods, using existing vaccines as a starting point.

The dosage of immunoreactive HA in each dose of replicated virus vaccine may be standardized to contain a suitable amount, e.g., 30 to 100 μg or any range or value therein, or the amount recommended by government agencies or recognized professional organizations. The quantity of NA can also be standardized, however, this glycoprotein may be labile during purification and storage.

The dosage of immunoreactive HA in each dose of replicated virus vaccine can be standardized to contain a suitable amount, e.g., 1-50 μg or any range or value therein, or the amount recommended by the U.S. Public Heath Service (PHS), which is usually 15 μg, per component for children >3 years of age, and 7.5 μg per component for children <3 years of age. The quantity of NA can also be standardized, however, this glycoprotein can be labile during the processor purification and storage (Kendal et al., 1980; Kerr et al., 1975). Each 0.5-ml dose of vaccine may contains approximately 1-50 billion virus particles, and preferably 10 billion particles.

The invention will be described by the following nonlimiting examples.

EXAMPLE 1

Methods

Cells and Viruses 293T human embryonic kidney cells are maintained in Dulbecco's modified Eagle's minimal essential medium (DMEM) with 10% fetal calf serum and antibiotics. Madin-Darby canine kidney (MDCK) cells are grown in MEM with 5% newborn calf serum and antibiotics. African green monkey Vero WCB cells, which had been established after biosafety tests for use in human vaccine production (Sugawara et al., 2002), are maintained in serum-free VP-SFM medium (GIBCO-BRL) with antibiotics. Cells are maintained at 37° C., in 5% $CO_2$. A WHO-recommended vaccine seed virus is NIBRG-14.

Construction of Plasmids and Reverse Genetics

To generate reassortants of influenza A viruses, a plasmid-based reverse genetics (Neumann et al., 1999) is used. The full-length cDNAs were cloned into a plasmid under control of the human polymerase I promoter and the mouse RNA polymerase I terminator (PolI plasmids).

A previously produced series of PolI constructs, derived from A/WSN/33 (H5N1; WSN) or PR8 strains is used, for reverse genetics (Horimoto et al., 2006; Neumann et al., 1999). The World Health Organization (WHO) recommends A/Puerto Rico/8/34 (H1N1; PR8) as a donor virus, because of its safety in humans (Wood & Robertson, 2004; Webby & Webster, 2003).

Plasmids expressing WSN or PR8 NP, PA, PB1, or PB2 under control of the chicken β-actin promoter are used for all reverse genetics experiments (Horimoto et al., 2006; Neumann et al., 1999). Briefly, PolI plasmids and protein expression plasmids are mixed with a transfection reagent, Trans-IT 293T (Panvera), incubated at room temperature for 15 minutes, and then added to 293T cells. Transfected cells are incubated in Opti-MEM I (GIBCO-BRL) for 48 hours. For reverse genetics in Vero WCB cells, an electroporator (Amaxa) is used to transfect the plasmid mixtures according to the manufacturer's instructions. Sixteen hours after transfection, freshly prepared Vero WCB cells were added onto the transfected cells and TPCK-trypsin (1 μg/mL) is added to the culture 6 hours later. Transfected cells are incubated in serum-free VP-SFM for a total of 4 days. Supernatants containing infectious viruses are harvested, and may bebiologically cloned by limiting dilution.

A recombinant virus having the HA and NA genes from A/Hong Kong/213/2003 (H5N1) and the remainder of the type A influenza virus genes from PR8(UW) was prepared. The titer of the recombinant virus was $10^{10.67}$ $EID_{50}$/mL, and the HA titer was 1:1600

TABLE 1

| Virus possessing PR8 genes together with the following HA and NA | HA titer (HAU/mL) in each dilition | | | | | | |
|---|---|---|---|---|---|---|---|
| genes | 10-2 | 10-3 | 10-4 | 10-5 | 10-6 | 10-7 | 10-8 |
| WSN-HA NA | 160 | 40 | 40 | 320 | 40 | 640 | <1 |
| HK-HAavir NA | 400 | 800 | 400 | 400 | 400 | 800 | <1 |

The sequences of PR8 (UW) genes are as follows:

PA (SEQ ID NO: 1)

```
AGCGAAAGCA GGTACTGATC CAAAATGGAA GATTTTGTGC GACAATGCTT

CAATCCGATG ATTGTCGAGC TTGCGGAAAA AACAATGAAA GAGTATGGGG

AGGACCTGAA AATCGAAACA AACAAATTTG CAGCAATATG CACTCACTTG

GAAGTATGCT TCATGTATTC AGATTTTCAC TTCATCAATG AGCAAGGCGA

GTCAATAATC GTAGAACTTG GTGATCCAAA TGCACTTTTG AAGCACAGAT

TTGAAATAAT CGAGGGAAGA GATCGCACAA TGGCCTGGAC AGTAGTAAAC

AGTATTTGCA ACACTACAGG GGCTGAGAAA CCAAAGTTTC TACCAGATTT

GTATGATTAC AAGGAGAATA GATTCATCGA AATTGGAGTA ACAAGGAGAG

AAGTTCACAT ATACTATCTG GAAAAGGCCA ATAAAATTAA ATCTGAGAAA

ACACACATCC ACATTTTCTC GTTCACTGGG GAAGAAATGG CCACAAAGGC
```

-continued

AGACTACACT CTCGATGAAG AAAGCAGGGC TAGGATCAAA ACCAGACTAT

TCACCATAAG ACAAGAAATG GCCAGCAGAG GCCTCTGGGA TTCCTTTCGT

CAGTCCGAGA GAGGAGAAGA GACAATTGAA GAAAGGTTTG AAATCACAGG

AACAATGCGC AAGCTTGCCG ACCAAAGTCT CCCGCCGAAC TTCTCCAGCC

TTGAAAATTT TAGAGCCTAT GTGGATGGAT TCGAACCGAA CGGCTACATT

GAGGGCAAGC TGTCTCAAAT GTCCAAAGAA GTAAATGCTA GAATTGAACC

TTTTTTGAAA ACAACACCAC GACCACTTAG ACTTCCGAAT GGGCCTCCCT

GTTCTCAGCG GTCCAAATTC CTGCTGATGG ATGCCTTAAA ATTAAGCATT

GAGGACCCAA GTCATGAAGG AGAGGGAATA CCGCTATATG ATGCAATCAA

ATGCATGAGA ACATTCTTTG GATGGAAGGA ACCCAATGTT GTTAAACCAC

ACGAAAAGGG AATAAATCCA AATTATCTTC TGTCATGGAA GCAAGTACTG

GCAGAACTGC AGGACATTGA GAATGAGGAG AAAATTCCAA AGACTAAAAA

TATGAAGAAA ACAAGTCAGC TAAAGTGGGC ACTTGGTGAG AACATGGCAC

CAGAAAAGGT AGACTTTGAC GACTGTAAAG ATGTAGGTGA TTTGAAGCAA

TATGATAGTG ATGAACCAGA ATTGAGGTCG CTTGCAAGTT GGATTCAGAA

TGAGTTTAAC AAGGCATGCG AACTGACAGA TTCAAGCTGG ATAGAGCTCG

ATGAGATTGG AGAAGATGTG GCTCCAATTG AACACATTGC AAGCATGAGA

AGGAATTATT TCACATCAGA GGTGTCTCAC TGCAGAGCCA CAGAATACAT

AATGAAGGGA GTGTACATCA ATACTGCCTT GCTTAATGCA TCTTGTGCAG

CAATGGATGA TTTCCAATTA ATTCCAATGA TAAGCAAGTG TAGAACTAAG

GAGGGAAGGC GAAAGACCAA CTTGTATGGT TTCATCATAA AAGGAAGATC

CCACTTAAGG AATGACACCG ACGTGGTAAA CTTTGTGAGC ATGGAGTTTT

CTCTCACTGA CCCAAGACTT GAACCACATA AATGGGAGAA GTACTGTGTT

CTTGAGATAG GAGATATGCT TATAAGAAGT GCCATAGGCC AGGTTTCAAG

GCCCATGTTC TTGTATGTGA GAACAAATGG AACCTCAAAA ATTAAAATGA

AATGGGGAAT GGAGATGAGG CGTTGCCTCC TCCAGTCACT TCAACAAATT

GAGAGTATGA TTGAAGCTGA GTCCTCTGTC AAAGAGAAAG ACATGACCAA

AGAGTTCTTT GAGAACAAAT CAGAAACATG GCCCATTGGA GAGTCCCCCA

AAGGAGTGGA GGAAAGTTCC ATTGGGAAGG TCTGCAGGAC TTTATTAGCA

AAGTCGGTAT TCAACAGCTT GTATGCATCT CCACAACTAG AAGGATTTTC

AGCTGAATCA AGAAAACTGC TTCTTATCGT TCAGGCTCTT AGGGACAACC

TGGAACCTGG GACCTTTGAT CTTGGGGGGC TATATGAAGC AATTGAGGAG

TGCCTGATTA ATGATCCCTG GGTTTTGCTT AATGCTTCTT GGTTCAACTC

CTTCCTTACA CATGCATTGA GTTAGTTGTG GCAGTGCTAC TATTTGCTAT

CCATACTGTC CAAAAAAGTA CCTTGTTTCT ACT

PB1

(SEQ ID NO: 2)

AGCGAAAGCA GGCAAACCAT TTGAATGGAT GTCAATCCGA

CCTTACTTTT CTTAAAAGTG CCAGCACAAA ATGCTATAAG CACAACTTTC

CCTTATACTG GAGACCCTCC TTACAGCCAT GGGACAGGAA CAGGATACAC

CATGGATACT GTCAACAGGA CACATCAGTA CTCAGAAAAG GGAAGATGGA

CAACAAACAC CGAAACTGGA GCACCGCAAC TCAACCCGAT TGATGGGCCA

-continued

CTGCCAGAAG ACAATGAACC AAGTGGTTAT GCCCAAACAG ATTGTGTATT

GGAGGCGATG GCTTTCCTTG AGGAATCCCA TCCTGGTATT TTTGAAAACT

CGTGTATTGA AACGATGGAG GTTGTTCAGC AAACACGAGT AGACAAGCTG

ACACAAGGCC GACAGACCTA TGACTGGACT CTAAATAGAA ACCAACCTGC

TGCAACAGCA TTGGCCAACA CAATAGAAGT GTTCAGATCA AATGGCCTCA

CGGCCAATGA GTCTGGAAGG CTCATAGACT TCCTTAAGGA TGTAATGGAG

TCAATGAACA AAGAAGAAAT GGGGATCACA ACTCATTTTC AGAGAAAGAG

ACGGGTGAGA GACAATATGA CTAAGAAAAT GATAACACAG AGAACAATGG

GTAAAAAGAA GCAGAGATTG AACAAAAGGA GTTATCTAAT TAGAGCATTG

ACCCTGAACA CAATGACCAA AGATGCTGAG AGAGGGAAGC TAAAACGGAG

AGCAATTGCA ACCCCAGGGA TGCAAATAAG GGGGTTTGTA TACTTTGTTG

AGACACTGGC AAGGAGTATA TGTGAGAAAC TTGAACAATC AGGGTTGCCA

GTTGGAGGCA ATGAGAAGAA AGCAAAGTTG GCAAATGTTG TAAGGAAGAT

GATGACCAAT TCTCAGGACA CCGAACTTTC TTTCACCATC ACTGGAGATA

ACACCAAATG GAACGAAAAT CAGAATCCTC GGATGTTTTT GGCCATGATC

ACATATATGA CCAGAAATCA GCCCGAATGG TTCAGAAATG TTCTAAGTAT

TGCTCCAATA ATGTTCTCAA ACAAAATGGC GAGACTGGGA AAAGGGTATA

TGTTTGAGAG CAAGAGTATG AAACTTAGAA CTCAAATACC TGCAGAAATG

CTAGCAAGCA TCGATTTGAA ATATTTCAAT GATTCAACAA GAAAGAAGAT

TGAAAAAATC CGACCGCTCT TAATAGAGGG GACTGCATCA TTGAGCCCTG

GAATGATGAT GGGCATGTTC AATATGTTAA GCACTGTATT AGGCGTCTCC

ATCCTGAATC TTGGACAAAA GAGATACACC AAGACTACTT ACTGGTGGGA

TGGTCTTCAA TCCTCTGACG ATTTTGCTCT GATTGTGAAT GCACCCAATC

ATGAAGGGAT TCAAGCCGGA GTCGACAGGT TTFATCGAAC CTGTAAGCTA

CTTGGAATCA ATATGAGCAA GAAAAAGTCT TACATAAACA GAACAGGTAC

ATTTGAATTC ACAAGTTTTT TCTATCGTTA TGGGTTTGTT GCCAATTTCA

GCATGGAGCT TCCCAGTTTT GGGGTGTCTG GGATCAACGA GTCAGCGGAC

ATGAGTATTG GAGTTACTGT CATCAAAAAC AATATGATAA ACAATGATCT

TGGTCCAGCA ACAGCTCAAA TGGCCCTTCA GTTGTTCATC AAAGATTACA

GGTACACGTA CCGATGCCAT ATAGGTGACA CACAAATACA AACCCGAAGA

TCATTTGAAA TAAAGAAACT GTGGGAGCAA ACCCGTTCCA AAGCTGGACT

GCTGGTCTCC GACGGAGGCC CAAATTTATA CAACATTAGA AATCTCCACA

TTCCTGAAGT CTGCCTAAAA TGGGAATTGA TGGATGAGGA TTACCAGGGG

CGTTTATGCA ACCCACTGAA CCCATTTGTC AGCCATAAAG AAATTGAATC

AATGAACAAT GCAGTGATGA TGCCAGCACA TGGTCCAGCC AAAAACATGG

AGTATGATGC TGTTGCAACA ACACACTCCT GGATCCCCAA AAGAAATCGA

TCCATCTTGA ATACAAGTCA AAGAGGAGTA CTTGAGGATG AACAAATGTA

CCAAAGGTGC TGCAATTTAT TTGAAAAATT CTTCCCCAGC AGTTCATACA

GAAGACCAGT CGGGATATCC AGTATGGTGG AGGCTATGGT TTCCAGAGCC

CGAATTGATG CACGGATTGA TTTCGAATCT GGAAGGATAA AGAAAGAAGA

-continued

GTTCACTGAG ATCATGAAGA TCTGTTCCAC CATTGAAGAG CTCAGACGGC

AAAAATAGTG AATTTAGCTT GTCCTTCATG AAAAAATGCC TTGTTTCTAC

T

PB2

(SEQ ID NO: 3)

AGCGAAAGCA GGTCAATTAT ATTCAATATG GAAAGAATAA AAGAACTACG

AAATCTAATG TCGCAGTCTC GCACCCGCGA GATACTCACA AAAACCACCG

TGGACCATAT GGCCATAATC AAGAAGTACA CATCAGGAAG ACAGGAGAAG

AACCCAGCAC TTAGGATGAA ATGGATGATG GCAATGAAAT ATCCAATTAC

AGCAGACAAG AGGATAACGG AAATGATTCC TGAGAGAAAT GAGCAAGGAC

AAACTTTATG GAGTAAAATG AATGATGCCG GATCAGACCG AGTGATGGTA

TCACCTCTGG CTGTGACATG GTGGAATAGG AATGGACCAA TAACAAATAC

AGTTCATTAT CCAAAAATCT ACAAAACTTA TTTTGAAAGA GTCGAAAGGC

TAAAGCATGG AACCTTTGGC CCTGTCCATT TTAGAAACCA AGTCAAAATA

CGTCGGAGAG TTGACATAAA TCCTGGTCAT GCAGATCTCA GTGCCAAGGA

GGCACAGGAT GTAATCATGG AAGTTGTTTT CCCTAACGAA GTGGGAGCCA

GGATACTAAC ATCGGAATCG CAACTAACGA TAACCAAAGA GAAGAAAGAA

GAACTCCAGG ATTGCAAAAT TTCTCCTTTG ATGGTTGCAT ACATGTTGGA

GAGAGAACTG GTCCGCAAAA CGAGATTCCT CCCAGTGGCT GGTGGAACAA

GCAGTGTGTA CATTGAAGTG TTGCATTTGA CTCAAGGAAC ATGCTGGGAA

CAGATGTATA CTCCAGGAGG GGAAGTGAGG AATGATGATG TTGATCAAAG

CTTGATTATT GCTGCTAGGA ACATAGTGAG AAGAGCTGCA GTATCAGCAG

ATCCACTAGC ATCTTTATTG GAGATGTGCC ACAGCACACA GATTGGTGGA

ATTAGGATGG TAGACATCCT TAGGCAGAAC CCAACAGAAG AGCAAGCCGT

GGATATATGC AAGGCTGCAA TGGGACTGAG AATTAGCTCA TCCTTCAGTT

TTGGTGGATT CACATTTAAG AGAACAAGCG GATCATCAGT CAAGAGAGAG

GAAGAGGTGC TTACGGGCAA TCTTCAAACA TTGAAGATAA GAGTGCATGA

GGGATATGAA GAGTTCACAA TGGTTGGGAG AAGAGCAACA GCCATACTCA

GAAAAGCAAC CAGGAGATTG ATTCAGCTGA TAGTGAGTGG GAGAGACGAA

CAGTCGATTG CCGAAGCAAT AATTGTGGCC ATGGTATTTT CACAAGAGGA

TTGTATGATA AAAGCAGTCA GAGGTGATCT GAATTTCGTC AATAGGGCGA

ATCAACGATT GAATCCTATG CATCAACTTT TAAGACATTT TCAGAAGGAT

GCGAAAGTGC TTTTTCAAAA TTGGGGAGTT GAACCTATCG ACAATGTGAT

GGGAATGATT GGGATATTGC CCGACATGAC TCCAAGCATC GAGATGTCAA

TGAGAGGAGT GAGAATCAGC AAAATGGGTG TAGATGAGTA CTCCAGCACG

GAGAGGGTAG TGGTGAGCAT TGACCGTTTT TTGAGAATCC GGGACCAACG

AGGAAATGTA CTACTGTCTC CCGAGGAGGT CAGTGAAACA CAGGGAACAG

AGAAACTGAC AATAACTTAC TCATCGTCAA TGATGTGGGA GATTAATGGT

CCTGAATCAG TGTTGGTCAA TACCTATCAA TGGATCATCA GAAACTGGGA

AACTGTTAAA ATTCAGTGGT CCCAGAACCC TACAATGCTA TACAATAAAA

TGGAATTTGA ACCATTTCAG TCTTTAGTAC CTAAGGCCAT TAGAGGCCAA

TACAGTGGGT TTGTAAGAAC TCTGTTCCAA CAAATGAGGG ATGTGCTTGG

-continued

GACATTTGAT ACCGCACAGA TAATAAAACT TCTTCCCTTC GCAGCCGCTC
CACCAAAGCA AAGTAGAATG CAGTTCTCCT CATTTACTGT GAATGTGAGG
GGATCAGGAA TGAGAATACT TGTAAGGGGC AATTCTCCTG TATTCAACTA
TAACAAGGCC ACGAAGAGAC TCACAGTTCT CGGAAAGGAT GCTGGCACTT
TAACTGAAGA CCCAGATGAA GGCACAGCTG GAGTGGAGTC CGCTGTTCTG
AGGGGATTCC TCATTCTGGG CAAAGAAGAC AAGAGATATG GGCCAGCACT
AAGCATCAAT GAACTGAGCA ACCTTGCGAA AGGAGAGAAG GCTAATGTGC
TAATTGGGCA AGGAGACGTG GTGTTGGTAA TGAAACGGAA ACGGGACTCT
AGCATACTTA CTGACAGCCA GACAGCGACC AAAAGAATTC GGATGGCCAT
CAATTAGTGT CGAATAGTTT AAAAACGACC TTGTTTCTAC T

NP (SEQ ID NO: 4)

AGCAAAAGCA GGGTAGATAA TCACTCACTG AGTGACATCA
AAATCATGGC GTCTCAAGGC ACCAAACGAT CTTACGAACA GATGGAGACT
GATGGAGAAC GCCAGAATGC CACTGAAATC AGAGCATCCG TCGGAAAAAT
GATTGGTGGA ATTGGACGAT TCTACATCCA AATGTGCACC GAACTCAAAC
TCAGTGATTA TGAGGGACGG TTGATCCAAA ACAGCTTAAC AATAGAGAGA
ATGGTGCTCT CTGCTTTTGA CGAAAGGAGA AATAAATACC TTGAAGAACA
TCCCAGTGCG GGGAAAGATC CTAAGAAAAC TGGAGGACCT ATATACAGGA
GAGTAAACGG AAAGTGGATG AGAGAACTCA TCCTTTATGA CAAAGAAGAA
ATAAGGCGAA TCTGGCGCCA AGCTAATAAT GGTGACGATG CAACGGCTGG
TCTGACTCAC ATGATGATCT GGCATTCCAA TTTGAATGAT GCAACTTATC
AGAGGACAAG AGCTCTTGTT CGCACCGGAA TGGATCCCAG GATGTGCTCT
CTGATGCAAG GTTCAACTCT CCCTAGGAGG TCTGGAGCCG CAGGTGCTGC
AGTCAAAGGA GTTGGAACAA TGGTGATGGA ATTGGTCAGA ATGATCAAAC
GTGGGATCAA TGATCGGAAC TTCTGGAGGG GTGAGAATGG ACGAAAAACA
AGAATTGCTT ATGAAAGAAT GTGCAACATT CTCAAAGGGA AATTTCAAAC
TGCTGCACAA AAAGCAATGA TGGATCAAGT GAGAGAGAGC CGGAACCCAG
GGAATGCTGA GTTCGAAGAT CTCACTTTTC TAGCACGGTC TGCACTCATA
TTGAGAGGGT CGGTTGCTCA CAAGTCCTGC CTGCCTGCCT GTGTGTATGG
ACCTGCCGTA GCCAGTGGGT ACGACTTTGA AAGGGAGGGA TACTCTCTAG
TCGGAATAGA CCCTTTCAGA CTGCTTCAAA ACAGCCAAGT GTACAGCCTA
ATCAGACCAA ATGAGAATCC AGCACACAAG AGTCAACTGG TGTGGATGGC
ATGCCATTCT GCCGCATTTG AAGATCTAAG AGTATTAAGC TTCATCAAAG
GGACGAAGGT GCTCCCAAGA GGGAAGCTTT CCACTAGAGG AGTTCAAATT
GCTTCCAATG AAAATATGGA GACTATGGAA TCAAGTACAC TTGAACTGAG
AAGCAGGTAC TGGGCCATAA GGACCAGAAG TGGAGGAAAC ACCAATCAAC
AGAGGGCATC TGCGGGCCAA ATCAGCATAC AACCTACGTT CTCAGTACAG
AGAAATCTCC CTTTTGACAG AACAACCATT ATGGCAGCAT TCAATGGGAA
TACAGAGGGG AGAACATCTG ACATGAGGAC CGAAATCATA AGGATGATGG
AAAGTGCAAG ACCAGAAGAT GTGTCTTTCC AGGGGCGGGG AGTCTTCGAG

-continued

CTCTCGGACG AAAAGGCAGC GAGCCCGATC GTGCCTTCCT TTGACATGAG

TAATGAAGGA TCTTATTTCT TCGGAGACAA TGCAGAGGAG TACGACAATT

AAAGAAAAAT ACCCTTGTTT CTACT

M (SEQ ID NO: 5)

AGCAAAAGCA GGTAGATATT GAAAGATGAG TCTTCTAACC GAGGTCGAAA

CGTACGTACT CTCTATCATC CCGTCAGGCC CCCTCAAAGC CGAGATCGCA

CAGAGACTTG AAGATGTCTT TGCAGGGAAG AACACCGATC TTGAGGTTCT

CATGGAATGG CTAAAGACAA GACCAATCCT GTCACCTCTG ACTAAGGGGA

TTTTAGGATT TGTGTTCACG CTCACCGTGC CCAGTGAGCG AGGACTGCAG

CGTAGACGCT TTGTCCAAAA TGCCCTTAAT GGGAACGGGG ATCCAAATAA

CATGGACAAA GCAGTTAAAC TGTATAGGAA GCTCAAGAGG GAGATAACAT

TCCATGGGGC CAAAGAAATC TCACTCAGTT ATTCTGCTGG TGCACTTGCC

AGTTGTATGG GCCTCATATA CAACAGGATG GGGGCTGTGA CCACTGAAGT

GGCATTTGGC CTGGTATGTG CAACCTGTGA ACAGATTGCT GACTCCCAGC

ATCGGTCTCA TAGGCAAATG GTGACAACAA CCAATCCACT AATCAGACAT

GAGAACAGAA TGGTTTTAGC CAGCACTACA GCTAAGGCTA TGGAGCAAAT

GGCTGGATCG AGTGAGCAAG CAGCAGAGGC CATGGAGGTT GCTAGTCAGG

CTAGACAAAT GGTGCAAGCG ATGAGAACCA TTGGGACTCA TCCTAGCTCC

AGTGCTGGTC TGAAAAATGA TCTTCTTGAA AATTTGCAGG CCTATCAGAA

ACGAATGGGG GTGCAGATGC AACGGTTCAA GTGATCCTCT CACTATTGCC

GCAAATATCA TTGGGATCTT GCACTTGACA TTGTGGATTC TTGATCGTCT

TTTTTTCAAA TGCATTTACC GTCGCTTTAA ATACGGACTG AAAGGAGGGC

CTTCTACGGA AGGAGTGCCA AAGTCTATGA GGGAAGAATA TCGAAAGGAA

CAGCAGAGTG CTGTGGATGC TGACGATGGT CATTTTGTCA GCATAGAGCT

GGAGTAAAAA ACTACCTTGT TTCTACT

NS (SEQ ID NO: 6)

AGCAAAAGCA GGGTGACAAA AACATAATGG ATCCAAACAC TGTGTCAAGC

TTTCAGGTAG ATTGCTTTCT TTGGCATGTC CGCAAACGAG TTGCAGACCA

AGAACTAGGC GATGCCCCAT TCCTTGATCG GCTTCGCCGA GATCAGAAAT

CCCTAAGAGG AAGGGGCAGT ACTCTCGGTC TGGACATCAA GACAGCCACA

CGTGCTGGAA AGCAGATAGT GGAGCGGATT CTGAAAGAAG AATCCGATGA

GCACTTAAA ATGACCATGG CCTCTGTACC TGCGTCGCGT TACCTAACTG

ACATGACTCT TGAGGAAATG TCAAGGGACT GGTCCATGCT CATACCCAAG

CAGAAAGTGG CAGGCCCTCT TTGTATCAGA ATGGACCAGG CGATCATGGA

TAAGAACATC ATACTGAAAG CGAACTTCAG TGTGATTTTT GACCGGCTGG

AGACTCTAAT ATTGCTAAGG GCTTTCACCG AAGAGGGAGC AATTGTTGGC

GAAATTTCAC CATTGCCTTC TCTTCCAGGA CATACTGCTG AGGATGTCAA

AAATGCAGTT GGAGTCCTCA TCGGAGGACT TGAATGGAAT GATAACACAG

TTCGAGTCTC TGAAACTCTA CAGAGATTCG CTTGGAGAAG CAGTAATGAG

AATGGGAGAC CTCCACTCAC TCCAAAACAG AAACGAGAAA TGGCGGGAAC

AATTAGGTCA GAAGTTTGAA GAAATAAGAT GGTTGATTGA AGAAGTGAGA

```
CACAAACTGA AGATAACAGA GAATAGTTTT GAGCAAATAA CATTTATGCA

AGCCTTACAT CTATTGCTTG AAGTGGAGCA AGAGATAAGA ACTTTCTCGT

TTCAGCTTAT TTAGTACTAA AAAACACCCT TGTTTCTACT
```

HA (SEQ ID NO: 7)

```
AGCAAAAGCAGGGGAAAATAAAAACAACCAAAATGAAGGCAAACCTACTGGTCCTGTTATGTGC

ACTTGCAGCTGCAGAT

GCAGACACAATATGTATAGGCTACCATGCGAACAATTCAACCGACACTGTTGACACAGTACTCGA

GAAGAATGTGACAGT

GACACACTCTGTTAACCTGCTCGAAGACAGCCACAACGGAAAACTATGTAGATTAAAAGGAATA

GCCCCACTACAATTGG

GGAAATGTAACATCGCCGGATGGCTCTTGGGAAACCCAGAATGCGACCCACTGCTTCCAGTGAG

ATCATGGTCCTACATT

GTAGAAACACCAAACTCTGAGAATGGAATATGTTATCCAGGAGATTTCATCGACTATGAGGAGCT

GAGGGAGCAATTGAG

CTCAGTGTCATCATTCGAAAGATTCGAAATATTTCCCAAAGAAAGCTCATGGCCCAACCACAACA

CAAACGGAGTAACGG

CAGCATGCTCCCATGAGGGGAAAAGCAGTTTTTACAGAAATTTGCTATGGCTGACGGAGAAGGA

GGGCTCATACCCAAAG

CTGAAAAATTCTTATGTGAACAAAAAAGGGAAAGAAGTCCTTGTACTGTGGGGTATTCATCACCC

GCCTAACAGTAAGGA

ACAACAGAATCTCTATCAGAATGAAAATGCTTATGTCTCTGTAGTGACTTCAAATTATAACAGGA

GATTTACCCCGGAAA

TAGCAGAAAGACCCAAAGTAAGAGATCAAGCTGGGAGGATGAACTATTACTGGACCTTGCTAAA

ACCCGGAGACACAATA

ATATTTGAGGCAAATGGAAATCTAATAGCACCAATGTATGCTTTCGCACTGAGTAGAGGCTTTGG

GTCCGGCATCATCAC

CTCAAACGCATCAATGCATGAGTGTAACACGAAGTGTCAAACACCCCTGGGAGCTATAAACAGC

AGTCTCCCTTACCAGA

ATATACACCCAGTCACAATAGGAGAGTGCCCAAAATACGTCAGGAGTGCCAAATTGAGGATGGT

TACAGGACTAAGGAAC

ATTCCGTCCATTCAATCCAGAGGTCTATTTGGAGCCATTGCCGGTTTTATTGAAGGGGGATGGAC

TGGAATGATAGATGG

ATGGTATGGTTATCATCATCAGAATGAACAGGGATCAGGCTATGCAGCGGATCAAAAAAGCACA

CAAAATGCCATTAACG

GGATTACAAACAAGGTGAACACTGTTATCGAGAAAATGAACATTCAATTCACAGCTGTGGGTAA

AGAATTCAACAAATTA

GAAAAAAGGATGGAAAAITTAAATAAAAAAGTTGATGATGGATTTCTGGACATTTGGACATATA

ATGCAGAATTGTTAGT

TCTACTGGAAAATGAAAGGACTCTGGATTTCCATGACTCAAATGTGAAGAATCTGTATGAGAAAG

TAAAAAGCCAATTAA
```

-continued

AGAATAATGCCAAAGAAATCGGAAATGGATGTTTTGAGTTCTACCACAAGTGTGACAATGAATG

CATGGAAAGTGTAAGA

AATGGGACTTATGATTATCCCAAATATTCAGAAGAGTCAAAGTTGAACAGGGAAAAGGTAGATG

GAGTGAAATTGGAATC

AATGGGGATCTATCAGATTCTGGCGATCTACTCAACTGTCGCCAGTTCACTGGTGCTTTTGGTCTC

CCTGGGGGCAATCA

GTTTCTGGATGTGTTCTAATGGATCTTTGCAGTGCAGAATATGCATCTGAGATTAGAATTTCAGAG

ATATGAGGAAAAAC

ACCCTTGTTTCTACT

NA (SEQ ID NO: 8)

AGCAAAAGCAGGGGTTTAAAATGAATCCAAATCAGAAAATAATAACCATTGGATCAATCTGTCT

GGTAGTCGGACTAATT

AGCCTAATATTGCAAATAGGGAATATAATCTCAATATGGATTAGCCATTCAATTCAAACTGGAAG

TCAAAACCATACTGG

AATATGCAACCAAAACATCATTACCTATAAAAATAGCACCTGGGTAAAGGACACAACTTCAGTG

ATATTAACCGGCAATT

CATCTCTTTGTCCCATCCGTGGGTGGGCTATATACAGCAAAGACAATAGCATAAGAATTGGTTCC

AAAGGAGACGTTTTT

GTCATAAGAGAGCCCTTTATTTCATGTTCTCACTTGGAATGCAGGACCTTTTTTCTGACCCAAGGT

GCCTTACTGAATGA

CAAGCATTCAAGTGGGACTGTTAAGGACAGAAGCCCTTATAGGGCCTTAATGAGCTGCCCTGTCG

GTGAAGCTCCGTCCC

CGTACAATTCAAGATTTGAATCGGTTGCTTGGTCAGCAAGTGCATGTCATGATGGCATGGGCTGG

CTAACAATCGGAATT

TCAGGTCCAGATAATGGAGCAGTGGCTGTATTAAAATACAACGGCATAATAACTGAAACCATAA

AAAGTTGGAGGAAGAA

AATATTGAGGACACAAGAGTCTGAATGTGCCTGTGTAAATGGTTCATGTTTTACTATAATGACTG

ATGGCCCGAGTGATG

GGCTGGCCTCGTACAAAATTTTCAAGATCGAAAAGGGGAAGGTTACTAAATCAATAGAGTTGAA

TGCACCTAATTCTCAC

TATGAGGAATGTTCCTGTTACCCTGATACCGGCAAAGTGATGTGTGTGTGCAGAGACAATTGGCA

TGGTTCGAACCGGCC

ATGGGTGTCTTTCGATCAAAACCTGGATTATCAAATAGGATACATCTGCAGTGGGGTTTTCGGTG

ACAACCCGCGTCCCG

AAGATGGAACAGGCAGCTGTGGTCCAGTGTATGTTGATGGAGCAAACGGAGTAAAGGGATTTTC

ATATAGGTATGGTAAT

GGTGTTTGGATAGGAAGGACCAAAAGTCACAGTTCCAGACATGGGTTTGAGATGATTTGGGATCC

TAATGGATGGACAGA

GACTGATAGTAAGTTCTCTGTGAGGCAAGATGTTGTGGCAATGACTGATTGGTCAGGGTATAGCG

GAAGTTTCGTTCAAC

-continued

```
ATCCTGAGCTGACAGGGCTAGACTGTATGAGGCCGTGCTTCTGGGTTGAATTAATCAGGGGACGA

CCTAAAGAAAAAACA

ATCTGGACTAGTGCGAGCAGCATTTCTTTTTGTGGCGTGAATAGTGATACTGTAGATTGGTCTTGG

CCAGACGGTGCTGA

GTTGCCATTCAGCATTGACAAGTAGTCTGTTCAAAAAACTCCTTGTTTCTACT
```

High-titer A/PR/8/34 (H1N1, PR8(UW)) virus grows 10 times better than other A/PR/8/34 PR8 strains in eggs ($10^{10}$ $EID_{50}$/mL; HA titer:1:8.000). Thus, replacement of the HA and NA genes of PR8(UW) with those of a currently circulating strain of influenza virus results in a vaccine strain that can be safely produced, and validates the use of PR8 (UW) as a master vaccine strain.

Genes that contribute to different growth properties between PR8(UW) and PR8 (Cambridge), which provides the non-HA and -NA genes of the NIBRG-14 vaccine strain (FIGS. 1A-C), were determined. Higher titers in eggs were obtained when the majority of internal genes were from PR8(UW). Highest titers were with the M gene segment of PR8(UW) and the NS gene of PR8 (Cambridge). The NS gene in PR8(UW) has a K (lysine) at residue 55 while the NS gene in PR8(Cam) has a E (glutamic acid). The polymerase subunit (PA, PB1, and PB2) and NP genes of PR8(UW) enhanced the growth of an H5N1 vaccine seed virus in chicken embryonated eggs, and the NS gene of PR8(Cambridge) enhanced the growth of an H5N1 vaccine seed virus in chicken embryonated eggs. A tyrosine (Y) at position 360 in PB2 of PR8(UW) likely contributes to the high growth rate of that virus in MDCK cells.

EXAMPLE 2

To establish robust systems for influenza vaccine production, egg-free, cell culture-based systems are needed. Vero cells are approved for human use and so are candidate hosts for influenza virus vaccine production. To elucidate the molecular basis for efficient growth of influenza vaccine seed virus in Vero cells. A/Puerto Rico/8/34 (PR8) virus was passaged through Vero cells 12 times and the infectivity titer of the resulting virus was determined. Vero cell-adapted PR8 had over a 4 log increase in infectivity titers relative to non Vero cell-adapted PR8 (FIG. 2).

Figure 4:
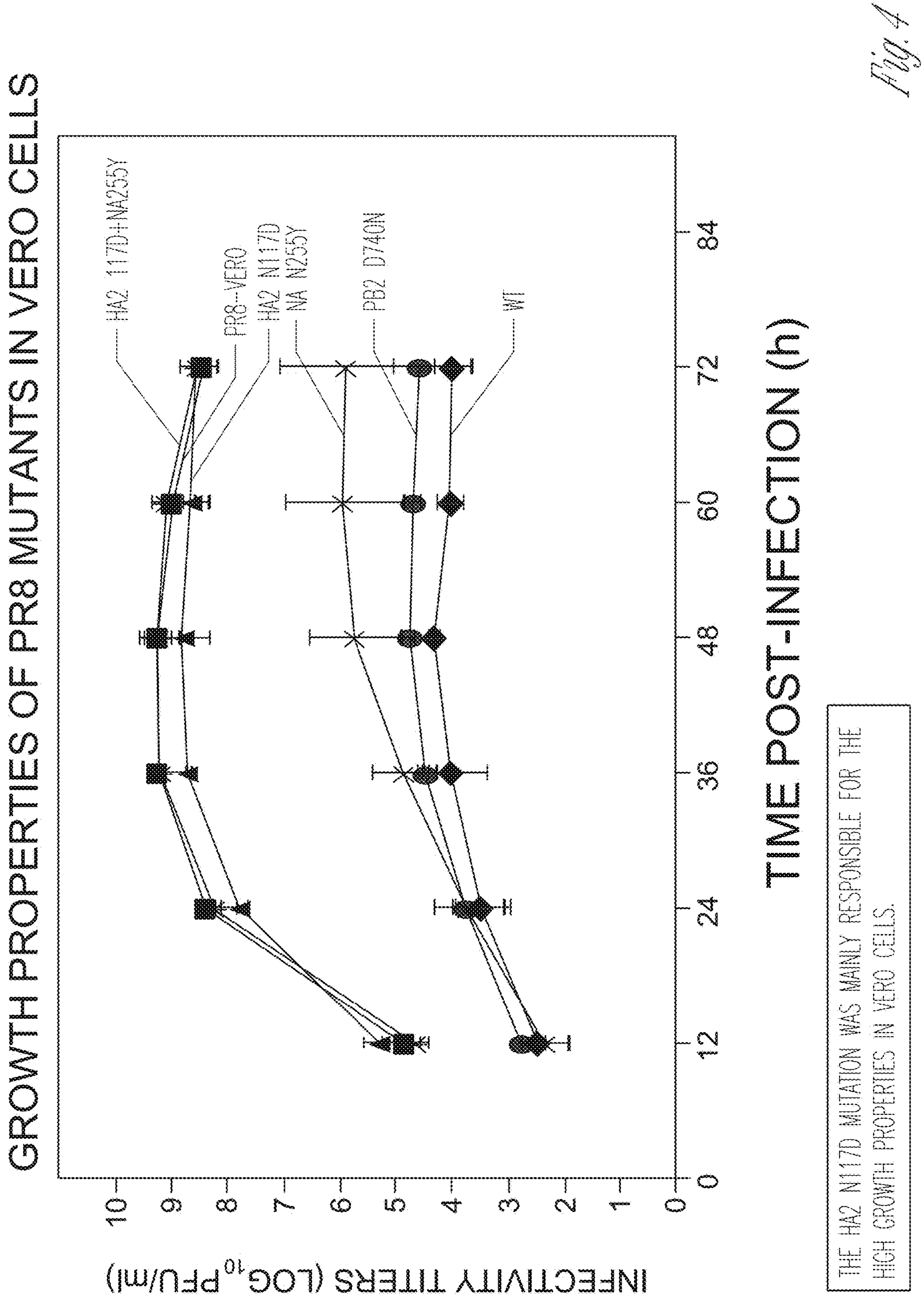
FIG. 4. Growth properties of Vero cell-adapted PR8, non Vero cell-adapted "wild-type" PR8, and recombinant viruses with one or two substitutions relative to wild-type virus in Vero cells.
Figure 5:
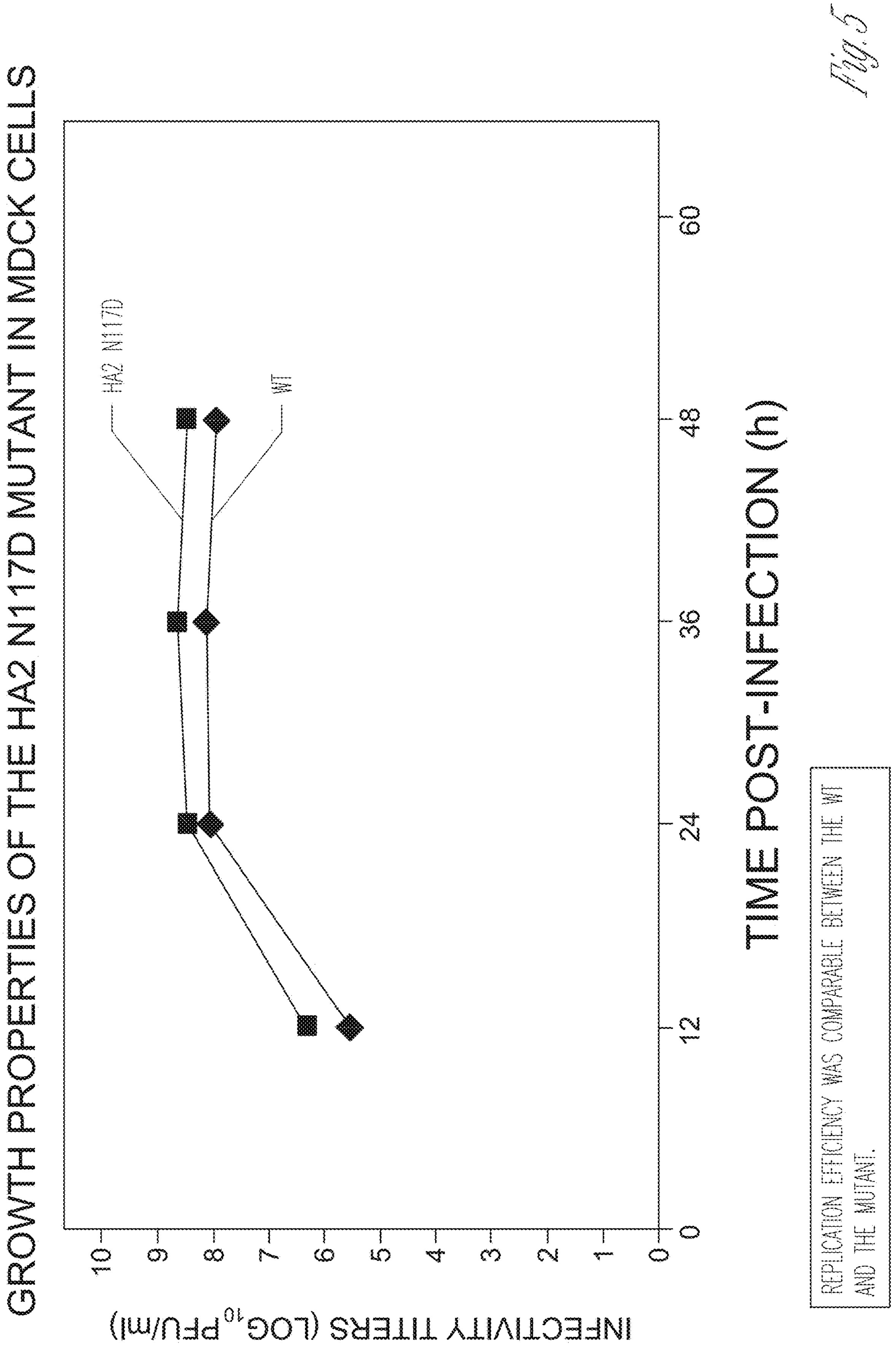
FIG. 5. Growth properties of HA2 N117D virus and wild-type PR8 in MDCK cells.
Figure 6:
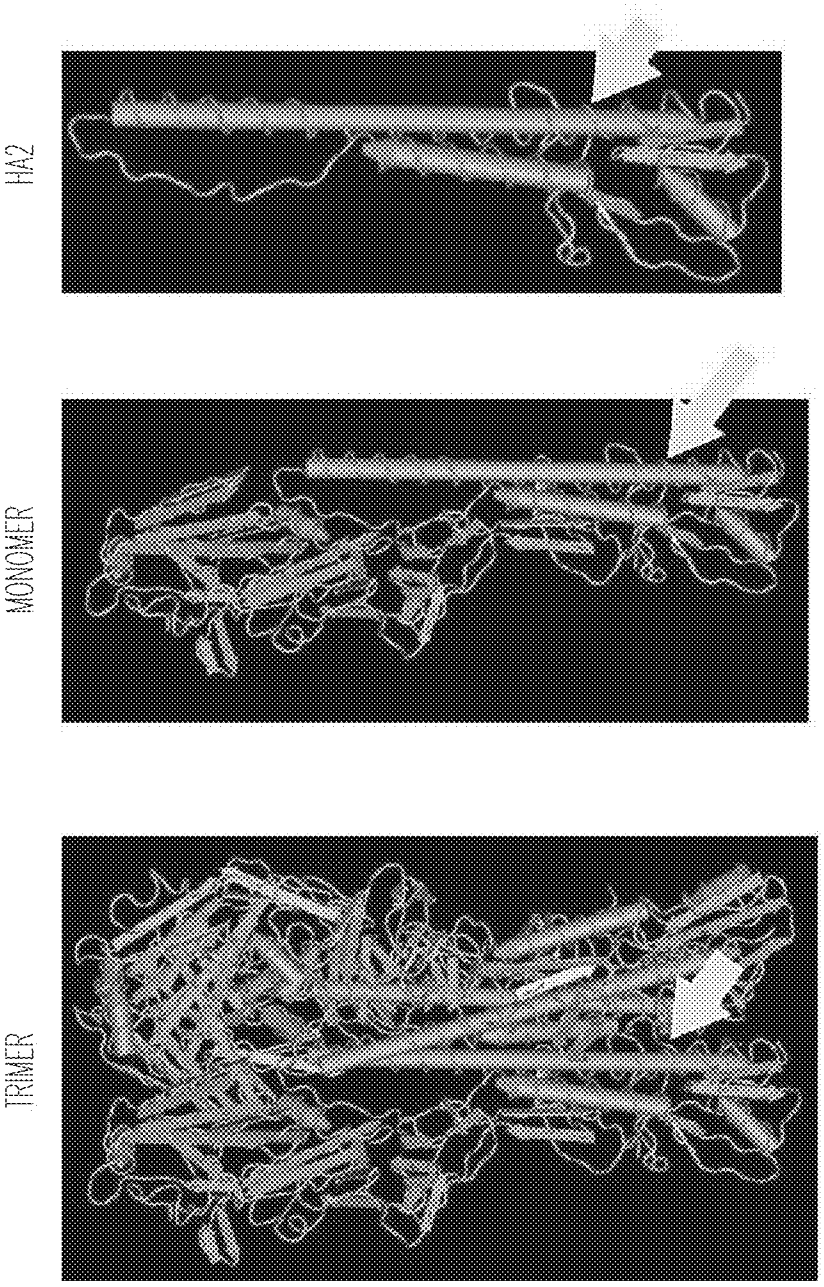
FIG. 6. Three dimensional structure of HA as a trimer (A), HA as a monomer (B) and HA2 (C).

To determine the molecular basis for that growth difference, the genomes of both isolates were sequenced. Three amino acid differences were found: one in HA2, one in NA and one in PB2 (FIG. 3). To identify the contribution of each individual substitution, and of a combination of two of the substitutions, recombinant viruses with the individual substitution(s) were prepared and the growth of those recombinant viruses was compared to Vero cell-adapted PR8 and non Vero cell-adapted PR8 (FIG. 4). The results indicated that the substitution in HA2 was primarily responsible for the enhanced growth in Vero cells. The substitution in HA2 (N117D) did not enhance growth in MDCK cells (FIG. 5).

Figure 7:
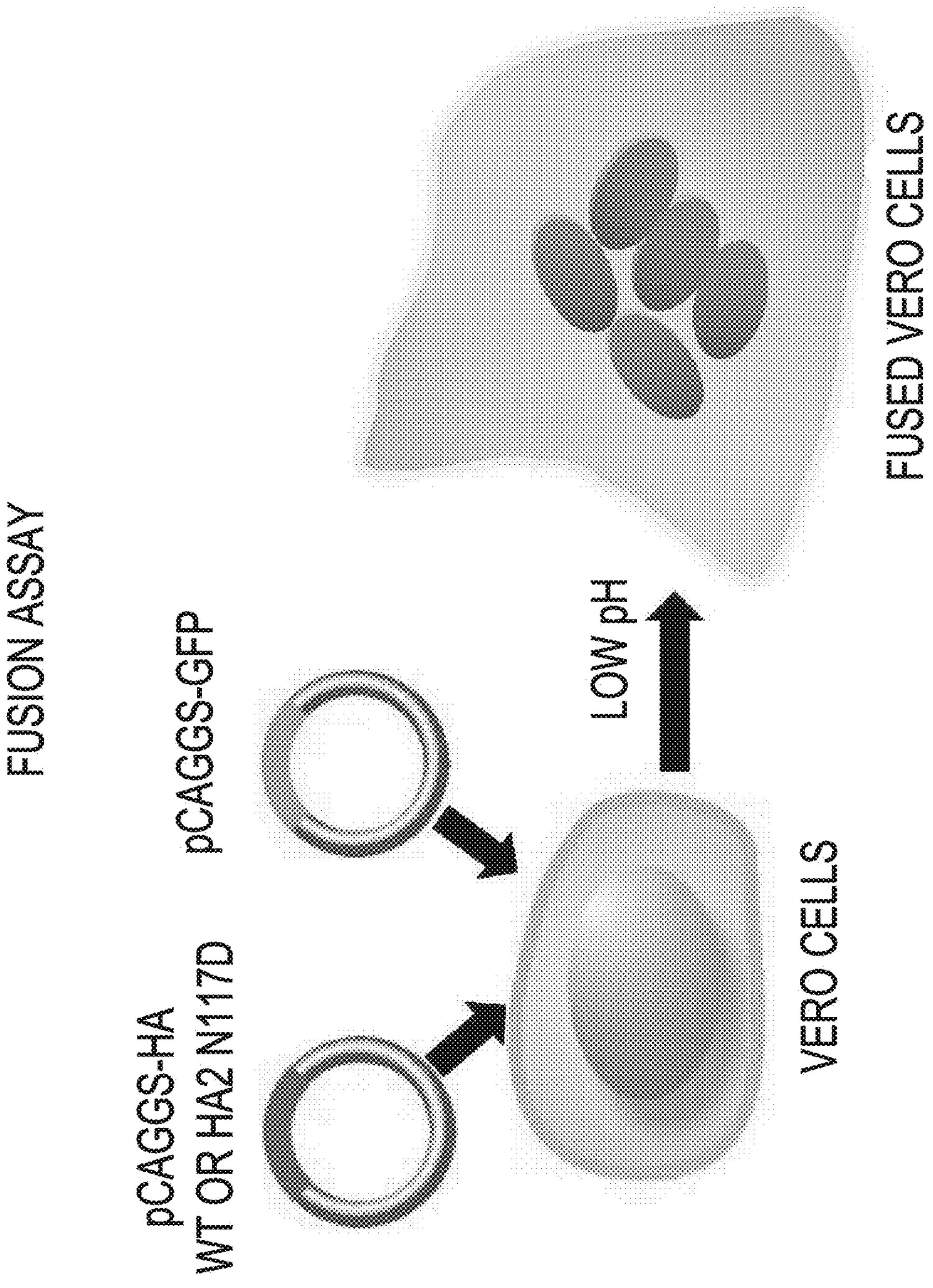
FIG. 7. Schematic of fusion assay which expresses full length HA.
Figure 8:
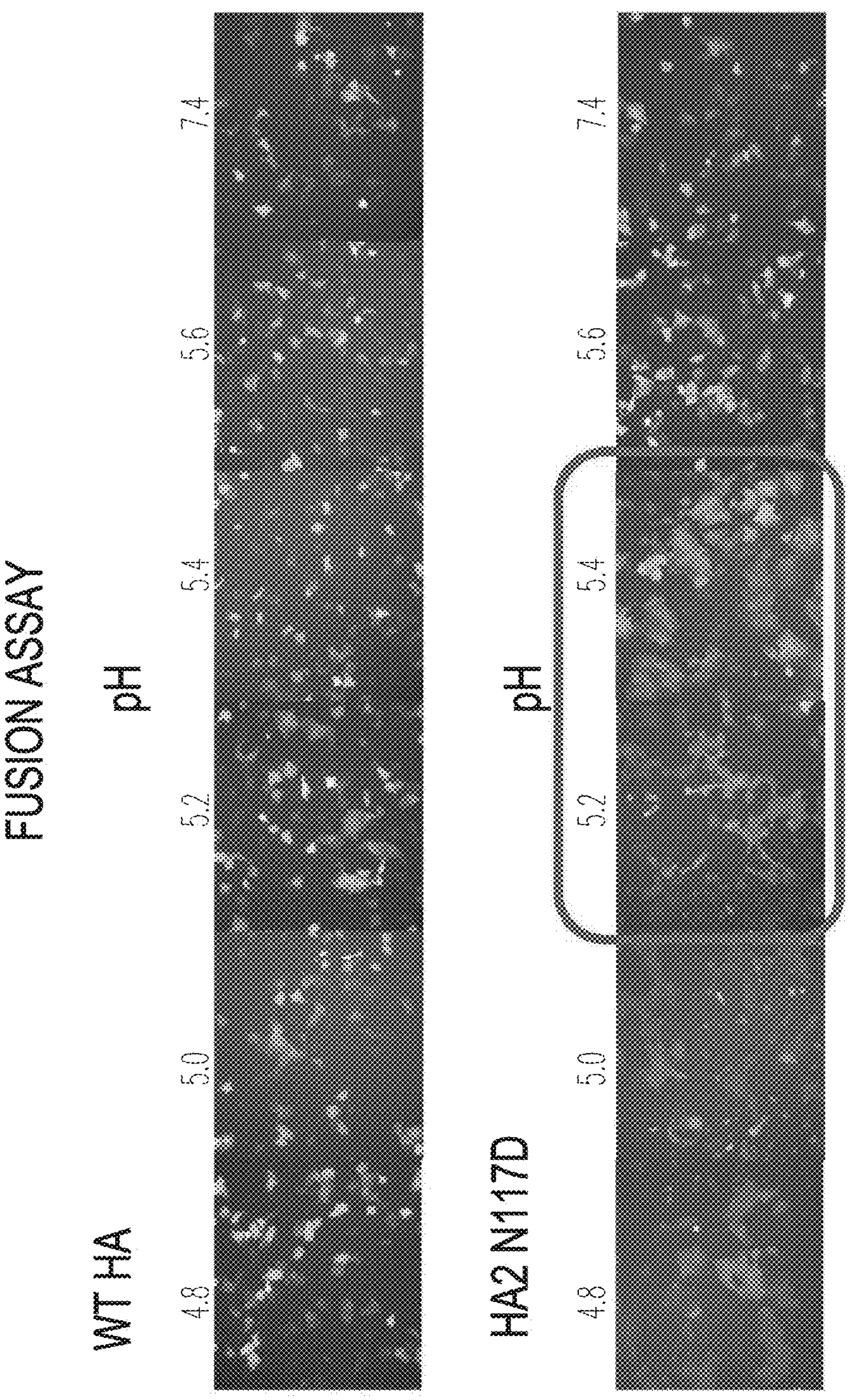
FIG. 8. Photomicrographs of Vero cells expressing wild-type PR8 HA or HA2 N117D virus at various pH conditions.
Figure 9A:
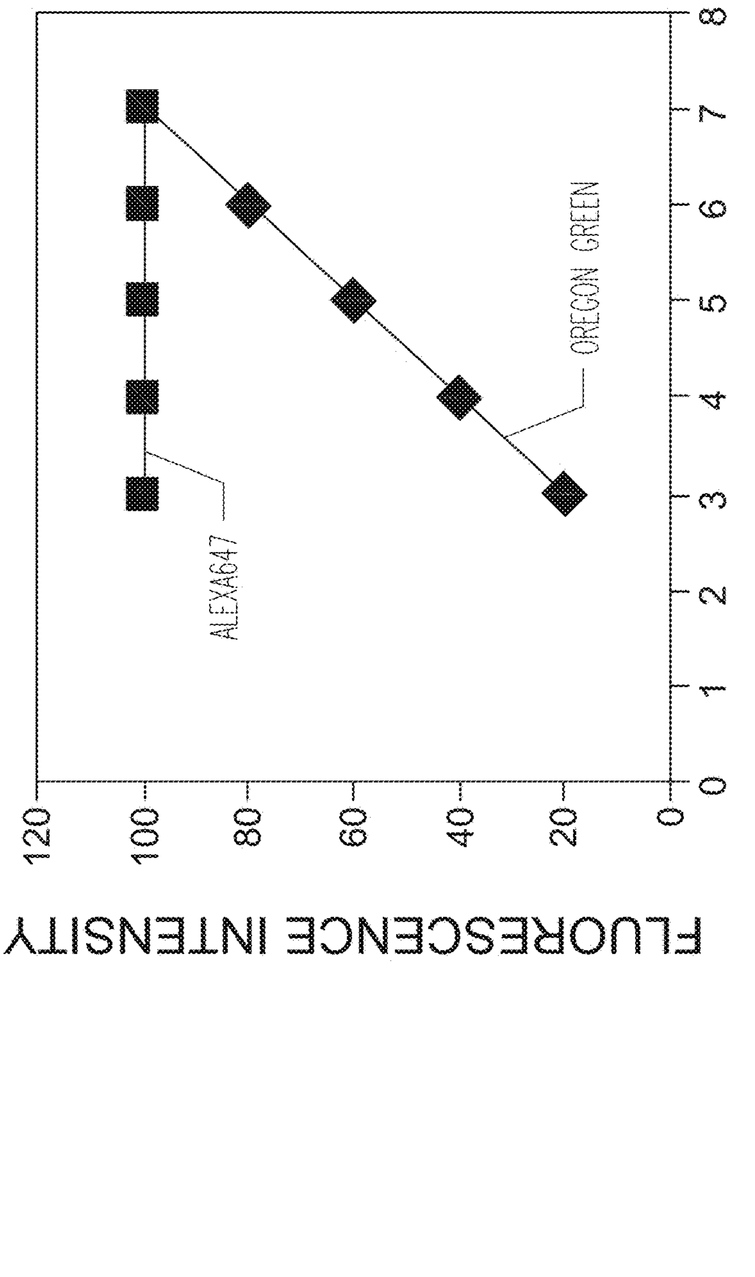
FIGS. 9A-B, pH sensitivity of Alexa647 and Oregon Green dyes. A) The fluorescence intensity of Oregon Green dye is sensitive to variations in pH while the fluorescence intensity of Alexa647 does not vary over pH 3 to 7. B) Schematic of assay to detect endosomal pH.
Figure 9B:
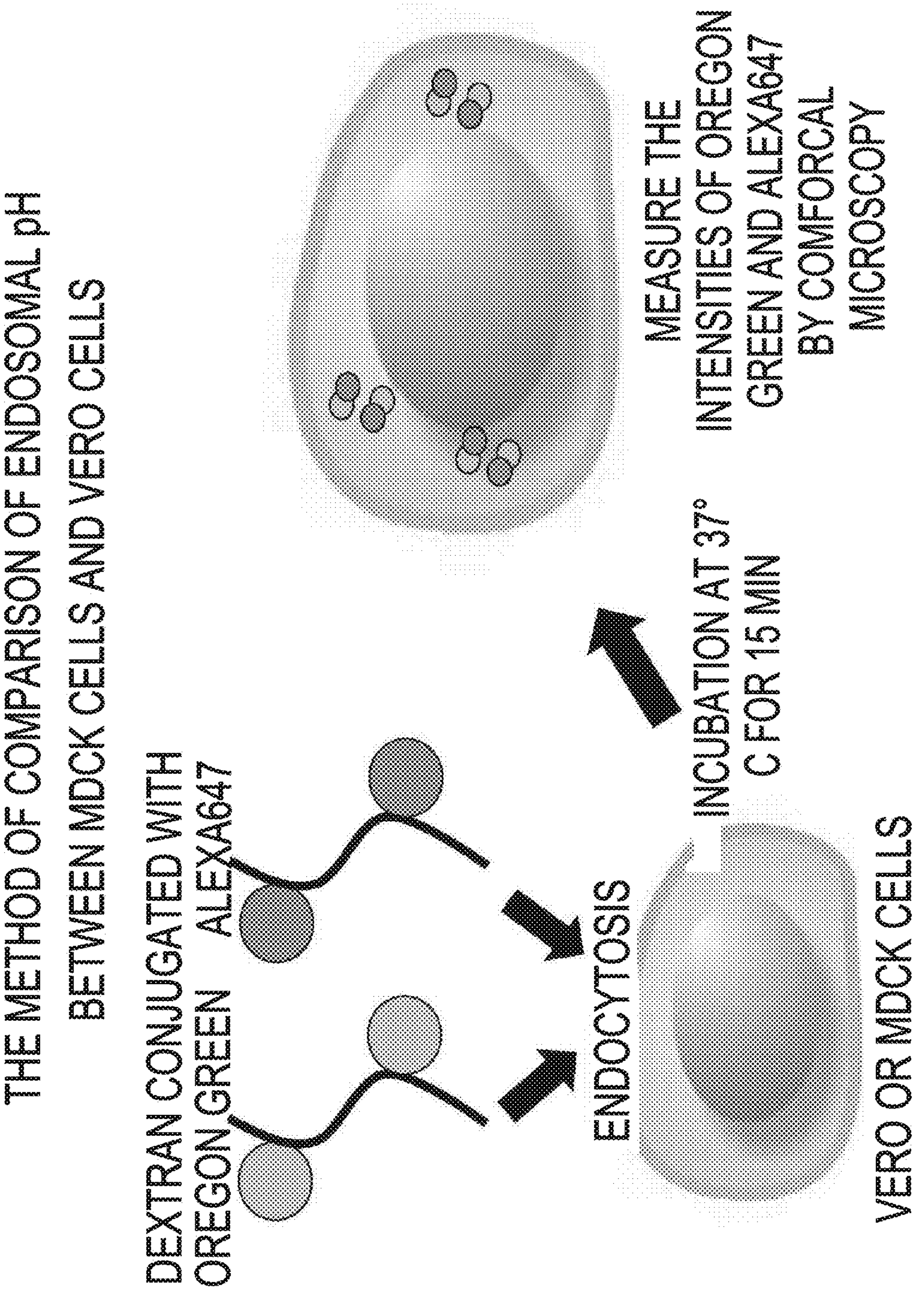
Figure 10:
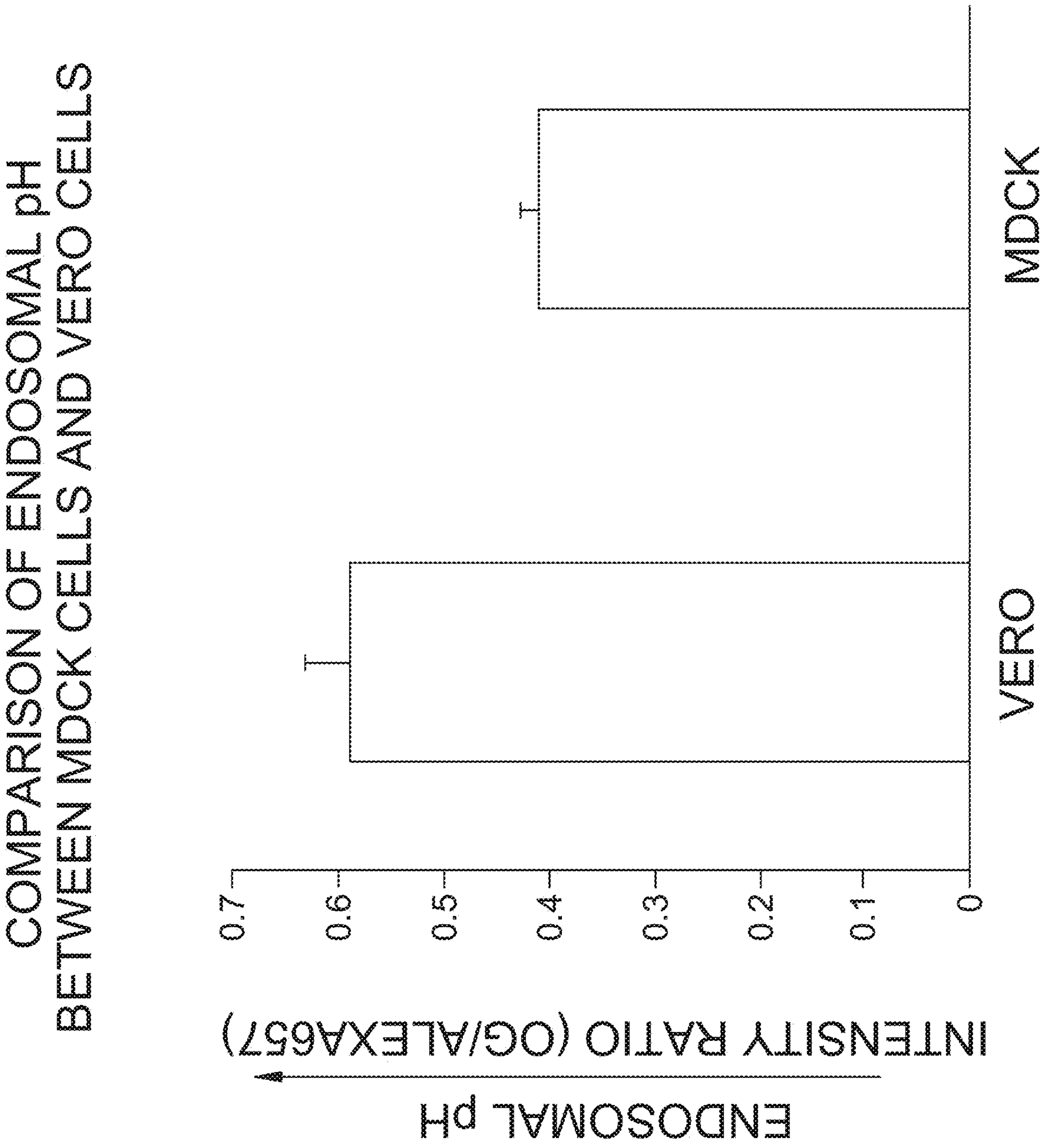
FIG. 10. Comparison of endosomal pH in MDCK cells and Vero cells.

Because HA2 has a fusion domain that is exposed after infection, a fusion assay was employed to compare the properties of wild-type PR8 HA2 and HA2 N117D (FIGS. 7-8). The HA2 N117D mutant fused Vero cells at a higher pH than wild-type PR8. The endosomal pH in Vero cells and MDCK cells was determined using pH sensitive and insensitive dyes (FIGS. 9-10). The endosomes of Vero cells likely have a higher pH than those from MDCK cells. Thus, the HA2 N117D mutation may elevate the optimal pH for membrane fusion mediated by HA2, thereby enhancing virus replication efficiency in Vero cells.

Figure 11A:
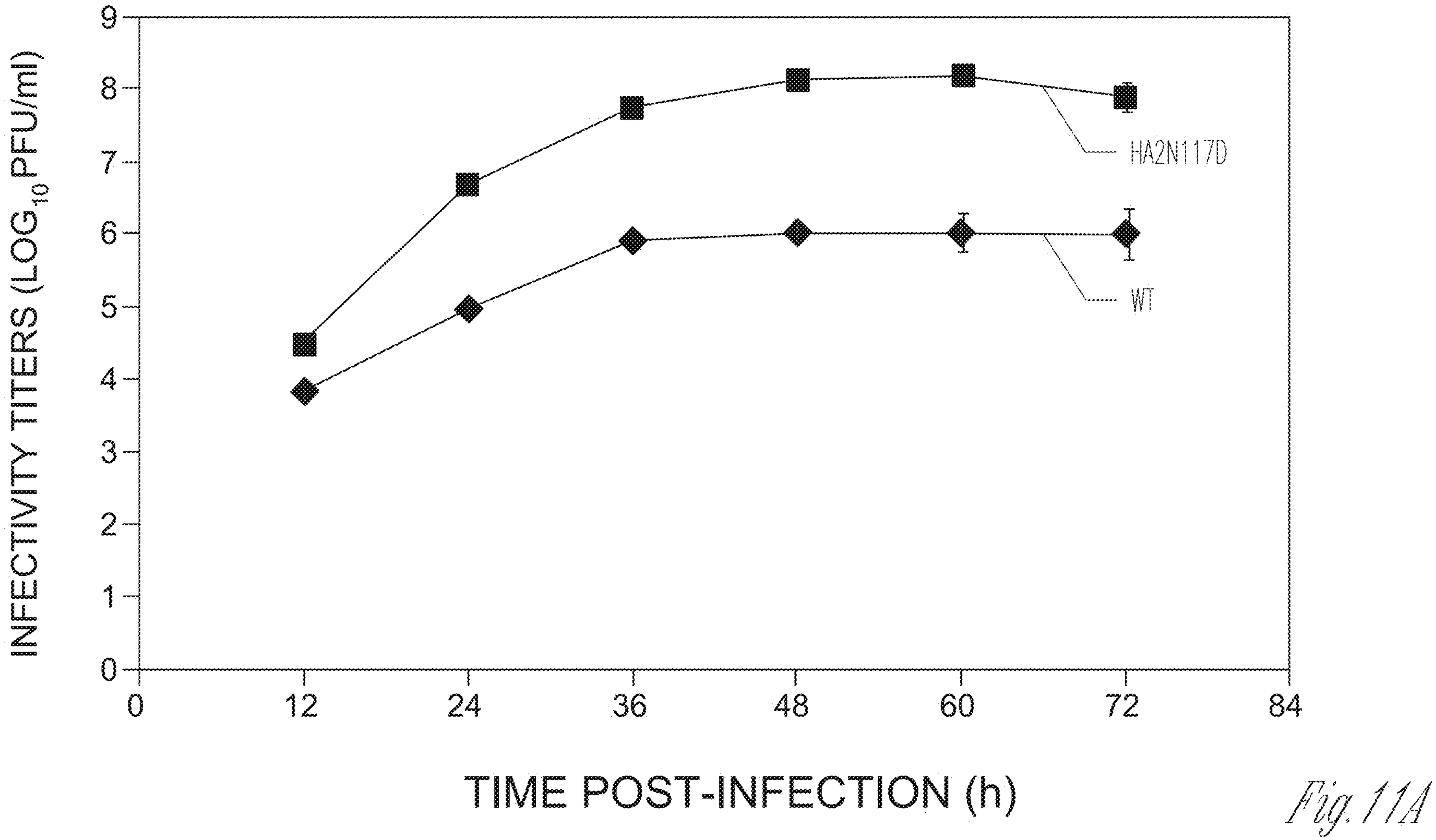
FIGS. 11A-C. HA2 N117D substitution mutants have enhanced infectivity titers in Vero cells. A) Vero cells were infected with A/Kawasaki/173/2001 (H1N1) and A/Kawasaki/173/2001 HA2 N117D and the titers over time determined. B) Vero cells were infected with A/Kawasaki/UTK-4/2009 (H1N1) and A/Kawasaki/UKT-4/2009 HA2 N117D and the titers over time determined. C) Vero cells were infected with A/Yokohama/2017/2003 (H3N2) and A/Yokohama/2017/2003 HA2 N116D and the titers over time determined.
Figure 11B:
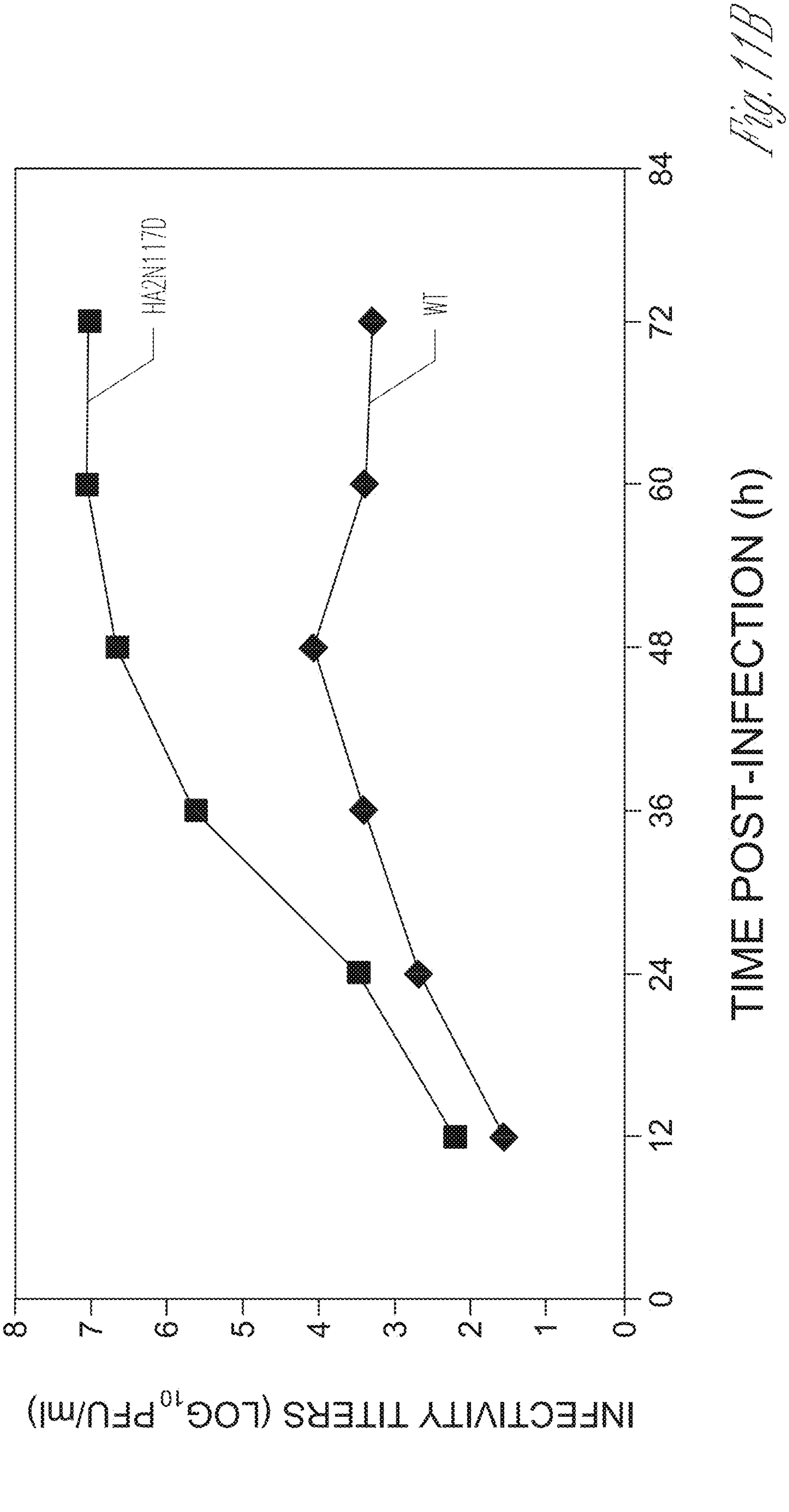
Figure 11C:
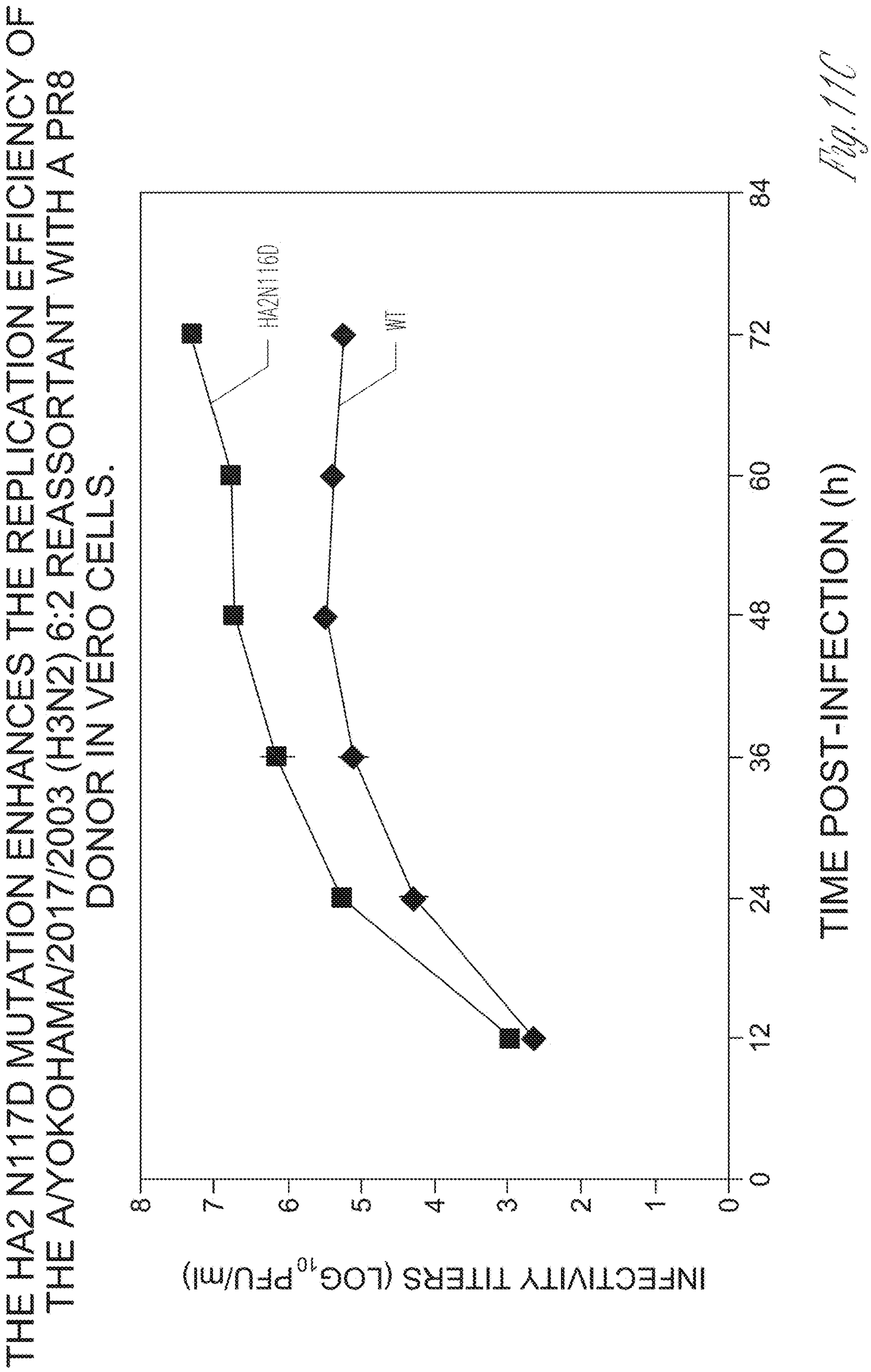

To determine if the HA2 N117D mutation alone could enhance virus replication efficiency in different viruses in Vero cells, that substitution was introduced into two different H1N1 viruses (a AAT to GAT mutation) and one H3N2 virus (a AAC to GAC mutation) in a PR8 background (six gene segments were from Vero cell-adapted PR8; PA, PB1, PB2, M. NS and NP) (FIG. 11). The HA2 N117D mutation enhanced the replication efficiency of all three tested viruses in Vero cells. Such a strategy may be employed to prepare vaccine viruses with enhanced replication in Vero cells.

REFERENCES

*Avery's Drug Treatment: Principles and Practice of Clinical Pharmacology and Therapeutics,* 3rd edition. ADIS Press, Ltd., Williams and Wilkins, Baltimore, Md. (1987).

Aymard-Henry et al., *Virology: A Practical Approach*, Oxford IRL Press, Oxford, 119-150 (1985).

Bachmeyer, *Intervirology,* 5:260 (1975).

Berkow et al., eds., *The Merck Manual.* 16th edition, Merck & Co., Rahway, N.J. (1992).

Hatta et al., *Science,* 293:1840 (2001).

Horimoto et al., *J. Virol.,* 68:3120 (1994).

Horimoto et al., *Vaccine,* 24:3669 (2006).

Keitel et al., in Textbook of Influenza, eds. Nickolson. K. G., Webster. R. G., and Hay, A. (Blackwell, Oxford), pp. 373-390 (1998).

Laver & Webster, *Virology.* 69:511 (1976).

Neumann et al., *Adv. Virus Res.,* 53:265 (1999).

Neumann et al., *J. Gen. Virol.,* 83:2635 (2002).

Neumann et al., *J. Virol.,* 71:9690 (1997).

Neumann et al., *Proc. Natl. Acad. Sci. USA,* 96:9345 (1999).

Neumann et al., *Virology,* 287:243 (2001).

Osol (ed.), *Remington's Pharmaceutical Sciences*, Mack Publishing Co., Easton, Pa. 1324-1341 (1980).

Sugawara et al., *Biologicals.* 30:303 (2002).

Webby & Webster et al., *Science.* 302:1519 (2003).

Wood & Robertson. *Nat. Rev. Microbiol.,* 2:842 (2004).

World Health Organization TSR No. 673 (1982).

World Health Organization. Confirmed human cases of avian influenza A (H5N1). http://www.who.int/csr/disease/avian_influenza/country/en/index.html All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An isolated Vero cell infected with a recombinant reassortant influenza virus having PA, PB1, PB2, NP, NS, and M gene segments from a first influenza vaccine virus isolate, an influenza virus NA gene segment, and an influenza virus HA gene segment selected to encode an aspartic acid or glutamic acid at position 117 in HA2, wherein the numbering for HA2residues is that for H1 HA.

2. The isolated cell of claim 1, wherein the NA gene segment and the HA gene segment in the reassortant virus are from the same influenza virus isolate and the HA gene segment in the reassortant virus is mutated to encode the aspartic acid or glutamic acid at position 117.

3. The isolated cell of claim 1, wherein the PA, PB1, PB2, NP, NS, and M gene segments in the reassortant virus comprise sequences for at least one of the following: a PB1 having the amino acid sequence encoded by SEQ ID NO:2 or PB1 with at least 95% amino acid sequence identity to the PB1 encoded by SEQ ID NO:2; a PB2 having the amino acid sequence encoded by SEQ ID NO:3 or PB2 with at least 95% amino acid sequence identity to the PB2encoded by SEQ NO:3; a PA having the amino acid sequence encoded by SEQ ID NO:1 or PA with at least 95% amino acid sequence identity to the PA encoded by SEQ ID NO:1; a NP having the amino acid sequence encoded by SEQ ID NO:4 or NP with at least 95% amino acid sequence identity to the NP encoded by SEQ ID NO:4; a M having the amino acid sequence encoded by SEQ ID NO:5 or M with at least 95% amino acid sequence identity to the M encoded by SEQ ID NO:5; or a NS having the amino acid sequence encoded by SEQ ID NO:6 or NS with at least 95% amino acid sequence identity to the NS encoded by SEQ ID NO:6.

4. The isolated cell of claim 1, wherein the PA, PB1, PB2, NP, NS, and M gene segments in the reassortant virus comprise sequences for at least one of the following: a PB1 having the amino acid sequence encoded by SEQ ID NO:10 or PB1 with at least 95% amino acid sequence identity to the PB1 encoded by SEQ NO:10; a PB2 having the amino acid sequence encoded by SEQ ID NO:11 or PB2 with at least 95% amino acid sequence identity to the PB2 encoded by SEQ ID NO:11; a PA having the amino acid sequence encoded by SEQ ID NO:12or PA with at least 95% amino acid sequence identity to the PA encoded by SEQ ID NO:12; a NP having the amino acid sequence encoded by SEQ ID NO:13 or NP with at least 95% amino acid sequence identity to the NP encoded by SEQ ID NO:13; a M having the amino acid sequence encoded by SEQ ID NO:14 or M with at least 95% amino acid sequence identity to the M encoded by SEQ ID NO:14; or a NS having the amino acid sequence encoded by SEQ ID NO:15 or NS with with at least 95% amino acid sequence identity to the NS encoded by SEQ ID NO:15.

5. The isolated cell of claim 1, wherein the HA gene segment is a H1, H2, H3, H5, H7, or H9 gene segment.

6. An isolated recombinant reassortant influenza virus having enhanced replication in Vero cells, prepared by:

providing a vector comprising sequences for a HA gene segment that does not encode an aspartic acid or glutamic: acid at position 117 in HA2, wherein the numbering for HA2 residues is that for H1 HA2;

altering the residue at position 117 in HA2 in the HA to aspartic acid or glutamic acid;

contacting cells with one or more vectors for expression of vRNAs for PA, PB1, PB2, NP, NS, M, HA and NA gene segments, wherein the vector for expression of HA vRNA comprises the sequences for a HA gene segment with the altered residue; and isolating from the cells recombinant reassortant influenza virus having enhanced replication in Vero cells.

7. The isolated recombinant virus of claim 6, wherein the HA gene segment is a H1, H2, H3, H5, H7, or H9 gene segment.

8. The isolated recombinant virus of claim 6, wherein the NA gene segment and the HA gene segment are from the same influenza virus isolate.

9. The isolated recombinant virus of claim 6, wherein the HA gene segment that does not encode an aspartic acid or glutamic acid at position 117 in HA2 has an alanine, asparagine, arginine or lysine at position 117 in HA2.

10. The isolated recombinant virus of claim 6, wherein the PA, PB1, PB2, NP, NS, and M gene segments are from the same influenza virus isolate.

11. The isolated recombinant virus of claim 6, wherein the PA, PB1, PB2, NP, NS, and M gene segments comprise sequences for a PB1 having the amino acid sequence encoded by SEQ ID NO:2; or PB1 with at least 90% amino acid sequence identity to the PB1encoded by SEQ ID NO:2; a PB2 having the amino acid sequence encoded by SEQ ID NO:3 or PB2 with at least 90% amino acid sequence identity to the PB2 encoded by SEQ ID NO:3; a PA having the amino acid sequence encoded by SEQ ID NO:1 or PA with at least 90% amino acid sequence identity to the PA encoded by SEQ NO:1; a NP having the amino acid sequence encoded by SEQ ID NO:4 or NP with at least 90% amino acid sequence identity to the NP encoded by SEQ ID NO:4; a M having the amino acid sequence encoded by SEQ ID NO:5 or M with at least 90% amino acid sequence identity to the M encoded by SEQ ID NO:5; or a NS having the amino acid sequence encoded by SEQ ID NO:6 or NS with at least 90% amino acid sequence identity to the NS encoded by SEQ ID NO:6.

12. The isolated recombinant virus of claim 6, wherein the PA, PB1, PB2, NP, NS, and M gene segments comprise sequences for a PB1 having the amino acid sequence encoded by SEQ ID NO:10 or PB1 with at least 90% amino acid sequence identity to the PB1encoded by SEQ ID NO:10; a PB2 having the amino acid sequence encoded by SEQ ID NO:11 or PB2 with at least 90% amino acid sequence identity to the PB2 encoded by SEQ ID NO:11; a PA having the amino acid sequence encoded by SEQ ID NO:12 or PA with at least 05% amino acid sequence identity to the PA encoded by SEQ ID NO:12; a NP having the amino acid sequence encoded by SEQ ID NO:13 or NP with at least 90% amino acid sequence identity to the NP encoded by SEQ ID NO:13; a M having the amino acid sequence encoded by SEQ ID NO:14 or M with at least 90% amino acid sequence identity to the M encoded by SEQ ID NO:14; or a NS having the amino acid sequence encoded by SEQ ID NO:15 or NS with at least 90% amino acid sequence identity to the NS encoded by SEQ ID NO:15.

13. The isolated recombinant of claim 6, wherein the cells are isolated avian cells.

14. The isolated recombinant virus of claim 6, wherein the cells are isolated mammalian cells.

15. The isolated recombinant virus of claim 14, wherein the isolated mammalian cells comprise a Vero cell, an isolated human cell or an isolated hamster cell.

16. The isolated recombine of claim 6, wherein the HA gene segment is a H1, H2, H3, H5, H7, or H9 gene segment.

17. A method to prepare an influenza virus with enhanced replication in Vero cells, comprising:

providing a vector comprising a recombinant nucleic acid molecule comprising sequences for an influenza virus HA gene segment from a first influenza virus isolate, which segment encodes an HA with an alanine, asparagine, arginine or lysine at position 117 in HA2, wherein the numbering for HA2 residues is that for H1 HA2;

modifying the HA gene segment to encode an aspartic acid or glutamic acid at position 117in HA2, thereby yielding a modified HA segment; and contacting a cell with a vector comprising promoter that yields full length, genomic influenza, virus RNA or its complement, operably linked to an influenza virus PA segment DNA linked to a transcription termination sequence, a vector comprising a promoter that yields full length, genomic influenza virus RNA or its complement operably linked to an influenza virus PB1 segment DNA linked to a transcription termination sequence, a vector comprising a promoter that yields full length, genomic influenza virus RNA or its complement operably linked to an influenza virus PB2 segment DNA linked to a transcription termination sequence, a vector comprising a promoter that yields full length, genomic influenza virus RNA or its complement operably linked to the modified HA segment linked to a transcription termination sequence, a vector comprising a promoter that yields full length, genomic influenza virus RNA or its complement operably linked to an influenza virus NP segment DNA linked to a transcription termination sequence, a vector comprising a promoter that yields full length, genomic influenza virus RNA or its complement operably linked to an influenza virus NA segment DNA linked to a transcription termination sequence, a vector comprising a promoter that yields full length, genomic influenza virus RNA or its complement operably linked to an influenza virus M segment DNA linked to a transcription termination sequence, and a vector comprising a promoter that yields full length, genomic influenza virus RNA or its complement operably linked to an influenza virus NS segment DNA linked to a transcription termination sequence; and a vector comprising a promoter that yields mRNA operably linked to a DNA segment encoding influenza virus PA, a vector comprising a promoter that yields mRNA operably linked to a DNA segment encoding influenza virus PB1, a vector comprising a promoter that yields mRNA operably linked to a DNA segment encoding influenza virus PB2, and a vector comprising a promoter that yields mRNA operably linked to a DNA segment encoding influenza virus NP, and optionally a vector comprising a promoter that yields mRNA operably linked to a DNA segment encoding influenza virus HA, a vector comprising a promoter that yields mRNA operably linked to a DNA segment encoding influenza virus NA, a vector comprising a promoter that yields mRNA operably linked to a DNA segment encoding influenza virus M1, a vector comprising a promoter that yields mRNA operably linked to a DNA segment encoding influenza virus M2, or a vector comprising a promoter that yields mRNA operably linked to a DNA segment encoding influenza virus NS1 or a vector comprising a promoter that yields mRNA operably linked to a DNA segment encoding influenza virus NS2;

in an amount effective to yield infectious influenza virus.

18. The method of claim 17, wherein the PA, PB1, PB2, NP, NS, and M segments are from an influenza vaccine virus isolate.

19. The method of claim 17, wherein the NA segment and the HA segment are from a different isolate than the PA, PB1, PB2, NR, NS, and M segments.

20. The method of claim 17, wherein the HA gene segment is a H1, H2, H3, H5,H7, or H9 gene segment.

* * * * *

SEQUENCE LISTING

<160> NUMBER OF SEQ ID NOS: 30

<210> SEQ ID NO 1
<211> LENGTH: 2233
<212> TYPE: DNA
<213> ORGANISM: Influenza virus

<400> SEQUENCE: 1
agcgaaagca ggtactgatc caaaatggaa gattttgtgc gacaatgctt caatccgatg 60
attgtcgagc ttgcggaaaa aacaatgaaa gagtatgggg aggacctgaa aatcgaaaca 120
aacaaatttg cagcaatatg cactcacttg gaagtatgct tcatgtattc agattttcac 180
ttcatcaatg agcaaggcga gtcaataatc gtagaacttg gtgatccaaa tgcacttttg 240
aagcacagat ttgaaataat cgagggaaga gatcgcacaa tggcctggac agtagtaaac 300
agtatttgca acactacagg ggctgagaaa ccaaagtttc taccagattt gtatgattac 360
aaggagaata gattcatcga aattggagta acaaggagag aagttcacat atactatctg 420
gaaaaggcca ataaaattaa atctgagaaa acacacatcc acatttttctc gttcactggg 480 gaagaaatgg ccacaaaggc agactacact ctcgatgaag aaagcagggc taggatcaaa 540
accagactat tcaccataag acaagaaatg gccagcagag gcctctggga ttcctttcgt 600
cagtccgaga gaggagaaga gacaattgaa gaaaggtttg aaatcacagg aacaatgcgc 660
aagcttgccg accaaagtct cccgccgaac ttctccagcc ttgaaaattt tagagcctat 720
gtggatggat tcgaaccgaa cggctacatt gagggcaagc tgtctcaaat gtccaaagaa 780
gtaaatgcta gaattgaacc ttttttgaaa acaacaccac gaccacttag acttccgaat 840
gggcctccct gttctcagcg gtccaaattc ctgctgatgg atgccttaaa attaagcatt 900
gaggacccaa gtcatgaagg agagggaata ccgctatatg atgcaatcaa atgcatgaga 960
acattctttg gatggaagga acccaatgtt gttaaaccac acgaaaaggg aataaatcca 1020
aattatcttc tgtcatggaa gcaagtactg gcagaactgc aggacattga gaatgaggag 1080
aaaattccaa agactaaaaa tatgaagaaa acaagtcagc taaagtgggc acttggtgag 1140
aacatggcac cagaaaaggt agactttgac gactgtaaag atgtaggtga tttgaagcaa 1200
tatgatagtg atgaaccaga attgaggtcg cttgcaagtt ggattcagaa tgagtttaac 1260
aaggcatgcg aactgacaga ttcaagctgg atagagctcg atgagattgg agaagatgtg 1320
gctccaattg aacacattgc aagcatgaga aggaattatt tcacatcaga ggtgtctcac 1380
tgcagagcca cagaatacat aatgaaggga gtgtacatca atactgcctt gcttaatgca 1440
tcttgtgcag caatggatga tttccaatta attccaatga taagcaagtg tagaactaag 1500
gagggaaggc gaaagaccaa cttgtatggt ttcatcataa aaggaagatc ccacttaagg 1560
aatgacaccg acgtggtaaa ctttgtgagc atggagtttt ctctcactga cccaagactt 1620
gaaccacata aatgggagaa gtactgtgtt cttgagatag gagatatgct tataagaagt 1680
gccataggcc aggtttcaag gcccatgttc ttgtatgtga gaacaaatgg aacctcaaaa 1740
attaaaatga aatggggaat ggagatgagg cgttgcctcc tccagtcact tcaacaaatt 1800
gagagtatga ttgaagctga gtcctctgtc aaagagaaag acatgaccaa agagttcttt 1860
gagaacaaat cagaaacatg gcccattgga gagtccccca aaggagtgga ggaaagttcc 1920
attgggaagg tctgcaggac tttattagca aagtcggtat tcaacagctt gtatgcatct 1980
ccacaactag aaggattttc agctgaatca agaaaactgc ttcttatcgt tcaggctctt 2040
agggacaacc tggaacctgg gacctttgat cttgggggc tatatgaagc aattgaggag 2100

-continued

```
tgcctgatta atgatccctg ggttttgctt aatgcttctt ggttcaactc cttccttaca   2160
catgcattga gttagttgtg gcagtgctac tatttgctat ccatactgtc caaaaaagta   2220
ccttgtttct act                                                      2233
```

<210> SEQ ID NO 2
<211> LENGTH: 2341
<212> TYPE: DNA
<213> ORGANISM: Influenza virus

<400> SEQUENCE: 2

```
agcgaaagca ggcaaaccat ttgaatggat gtcaatccga ccttactttt cttaaaagtg     60
ccagcacaaa atgctataag cacaactttc ccttatactg gagaccctcc ttacagccat    120
gggacaggaa caggatacac catggatact gtcaacagga cacatcagta ctcagaaaag    180
ggaagatgga caacaaacac cgaaactgga gcaccgcaac tcaacccgat tgatgggcca    240
ctgccagaag acaatgaacc aagtggttat gcccaaacag attgtgtatt ggaggcgatg    300
gctttccttg aggaatccca tcctggtatt tttgaaaact cgtgtattga aacgatggag    360
gttgttcagc aaacacgagt agacaagctg acacaaggcc gacagaccta tgactggact    420
ctaaatagaa accaacctgc tgcaacagca ttggccaaca caatagaagt gttcagatca    480
aatggcctca cggccaatga gtctggaagg ctcatagact tccttaagga tgtaatggag    540
tcaatgaaca aagaagaaat ggggatcaca actcattttc agagaaagag acgggtgaga    600
gacaatatga ctaagaaaat gataacacag agaacaatgg gtaaaaagaa gcagagattg    660
aacaaaagga gttatctaat tagagcattg accctgaaca caatgaccaa agatgctgag    720
agagggaagc taaaacggag agcaattgca accccaggga tgcaaataag gggggtttgta    780
tactttgttg agacactggc aaggagtata tgtgagaaac ttgaacaatc agggttgcca    840
gttggaggca atgagaagaa agcaaagttg gcaaatgttg taaggaagat gatgaccaat    900
tctcaggaca ccgaactttc tttcaccatc actggagata acaccaaatg gaacgaaaat    960
cagaatcctc ggatgttttt ggccatgatc acatatatga ccagaaatca gcccgaatgg   1020
ttcagaaatg ttctaagtat tgctccaata atgttctcaa acaaaaatggc gagactggga   1080
aaagggtata tgtttgagag caagagtatg aaacttagaa ctcaaatacc tgcagaaatg   1140
ctagcaagca tcgatttgaa atatttcaat gattcaacaa gaaagaagat tgaaaaaatc   1200
cgaccgctct taatagaggg gactgcatca ttgagccctg gaatgatgat gggcatgttc   1260
aatatgttaa gcactgtatt aggcgtctcc atcctgaatc ttggacaaaa gagatacacc   1320
aagactactt actggtggga tggtcttcaa tcctctgacg attttgctct gattgtgaat   1380
gcacccaatc atgaagggat tcaagccgga gtcgacaggt tttatcgaac ctgtaagcta   1440
cttggaatca atatgagcaa gaaaaagtct tacataaaca gaacaggtac atttgaattc   1500
acaagttttt tctatcgtta tgggtttgtt gccaatttca gcatggagct tcccagtttt   1560
ggggtgtctg ggatcaacga gtcagcggac atgagtattg gagttactgt catcaaaaac   1620
aatatgataa acaatgatct tggtccagca acagctcaaa tggcccttca gttgttcatc   1680
aaagattaca ggtacacgta ccgatgccat ataggtgaca cacaaataca aacccgaaga   1740
tcatttgaaa taaagaaact gtgggagcaa acccgttcca aagctggact gctggtctcc   1800
gacggaggcc caaatttata caacattaga aatctccaca ttcctgaagt ctgcctaaaa   1860
tgggaattga tggatgagga ttaccagggg cgtttatgca acccactgaa cccatttgtc   1920
```

```
agccataaag aaattgaatc aatgaacaat gcagtgatga tgccagcaca tggtccagcc   1980

aaaaacatgg agtatgatgc tgttgcaaca acacactcct ggatccccaa aagaaatcga   2040

tccatcttga atacaagtca aagaggagta cttgaggatg aacaaatgta ccaaaggtgc   2100

tgcaatttat ttgaaaaatt cttccccagc agttcataca gaagaccagt cgggatatcc   2160

agtatggtgg aggctatggt ttccagagcc cgaattgatg cacggattga tttcgaatct   2220

ggaaggataa agaaagaaga gttcactgag atcatgaaga tctgttccac cattgaagag   2280

ctcagacggc aaaaatagtg aatttagctt gtccttcatg aaaaaatgcc ttgtttctac   2340

t                                                                   2341
```

<210> SEQ ID NO 3
<211> LENGTH: 2341
<212> TYPE: DNA
<213> ORGANISM: Influenza virus

<400> SEQUENCE: 3

```
agcgaaagca ggtcaattat attcaatatg gaaagaataa aagaactacg aaatctaatg     60

tcgcagtctc gcacccgcga gatactcaca aaaaccaccg tggaccatat ggccataatc    120

aagaagtaca catcaggaag acaggagaag aacccagcac ttaggatgaa atggatgatg    180

gcaatgaaat atccaattac agcagacaag aggataacgg aaatgattcc tgagagaaat    240

gagcaaggac aaactttatg gagtaaaatg aatgatgccg gatcagaccg agtgatggta    300

tcacctctgg ctgtgacatg gtggaatagg aatggaccaa taacaaatac agttcattat    360

ccaaaaatct acaaaactta ttttgaaaga gtcgaaaggc taaagcatgg aacctttggc    420

cctgtccatt ttagaaacca agtcaaaata cgtcggagag ttgacataaa tcctggtcat    480

gcagatctca gtgccaagga ggcacaggat gtaatcatgg aagttgtttt ccctaacgaa    540

gtgggagcca ggatactaac atcggaatcg caactaacga taaccaaaga gaagaaagaa    600

gaactccagg attgcaaaat ttctcctttg atggttgcat acatgttgga gagagaactg    660

gtccgcaaaa cgagattcct cccagtggct ggtggaacaa gcagtgtgta cattgaagtg    720

ttgcatttga ctcaaggaac atgctgggaa cagatgtata ctccaggagg ggaagtgagg    780

aatgatgatg ttgatcaaag cttgattatt gctgctagga acatagtgag aagagctgca    840

gtatcagcag atccactagc atctttattg gagatgtgcc acagcacaca gattggtgga    900

attaggatgg tagacatcct taggcagaac ccaacagaag agcaagccgt ggatatatgc    960

aaggctgcaa tgggactgag aattagctca tccttcagtt ttggtggatt cacatttaag   1020

agaacaagcg gatcatcagt caagagagag gaagaggtgc ttacgggcaa tcttcaaaca   1080

ttgaagataa gagtgcatga gggatatgaa gagttcacaa tggttgggag aagagcaaca   1140

gccatactca gaaaagcaac caggagattg attcagctga tagtgagtgg gagagacgaa   1200

cagtcgattg ccgaagcaat aattgtggcc atggtatttt cacaagagga ttgtatgata   1260

aaagcagtca gaggtgatct gaatttcgtc aatagggcga atcaacgatt gaatcctatg   1320

catcaacttt taagacattt tcagaaggat gcgaaagtgc tttttcaaaa ttggggagtt   1380

gaacctatcg acaatgtgat gggaatgatt gggatattgc ccgacatgac tccaagcatc   1440

gagatgtcaa tgagaggagt gagaatcagc aaaatgggtg tagatgagta ctccagcacg   1500

gagagggtag tggtgagcat tgaccgtttt ttgagaatcc gggaccaacg aggaaatgta   1560

ctactgtctc ccgaggaggt cagtgaaaca cagggaacag agaaactgac aataacttac   1620

tcatcgtcaa tgatgtggga gattaatggt cctgaatcag tgttggtcaa tacctatcaa   1680
```

tggatcatca gaaactggga aactgttaaa attcagtggt cccagaaccc tacaatgcta 1740
tacaataaaa tggaatttga accatttcag tctttagtac ctaaggccat tagaggccaa 1800
tacagtgggt ttgtaagaac tctgttccaa caaatgaggg atgtgcttgg gacatttgat 1860
accgcacaga taataaaact tcttcccttc gcagccgctc caccaaagca aagtagaatg 1920
cagttctcct catttactgt gaatgtgagg ggatcaggaa tgagaatact tgtaaggggc 1980
aattctcctg tattcaacta taacaaggcc acgaagagac tcacagttct cggaaaggat 2040
gctggcactt taactgaaga cccagatgaa ggcacagctg gagtggagtc cgctgttctg 2100
aggggattcc tcattctggg caaagaagac aagagatatg ggccagcact aagcatcaat 2160
gaactgagca accttgcgaa aggagagaag gctaatgtgc taattgggca aggagacgtg 2220
gtgttggtaa tgaaacggaa acgggactct agcatactta ctgacagcca gacagcgacc 2280
aaaagaattc ggatggccat caattagtgt cgaatagttt aaaaacgacc ttgtttctac 2340
t 2341

<210> SEQ ID NO 4
<211> LENGTH: 1565
<212> TYPE: DNA
<213> ORGANISM: Influenza virus

<400> SEQUENCE: 4
agcaaaagca gggtagataa tcactcactg agtgacatca aaatcatggc gtctcaaggc 60
accaaacgat cttacgaaca gatggagact gatggagaac gccagaatgc cactgaaatc 120
agagcatccg tcggaaaaat gattggtgga attggacgat tctacatcca aatgtgcacc 180
gaactcaaac tcagtgatta tgagggacgg ttgatccaaa acagcttaac aatagagaga 240
atggtgctct ctgcttttga cgaaaggaga aataaatacc ttgaagaaca tcccagtgcg 300
gggaaagatc ctaagaaaac tggaggacct atatacagga gagtaaacgg aaagtggatg 360
agagaactca tcctttatga caaagaagaa ataaggcgaa tctggcgcca agctaataat 420
ggtgacgatg caacggctgg tctgactcac atgatgatct ggcattccaa tttgaatgat 480
gcaacttatc agaggacaag agctcttgtt cgcaccggaa tggatcccag gatgtgctct 540
ctgatgcaag gttcaactct ccctaggagg tctggagccg caggtgctgc agtcaaagga 600
gttggaacaa tggtgatgga attggtcaga atgatcaaac gtgggatcaa tgatcggaac 660
ttctggaggg gtgagaatgg acgaaaaaca agaattgctt atgaaagaat gtgcaacatt 720
ctcaaaggga aatttcaaac tgctgcacaa aaagcaatga tggatcaagt gagagagagc 780
cggaacccag ggaatgctga gttcgaagat ctcacttttc tagcacggtc tgcactcata 840
ttgagagggt cggttgctca caagtcctgc ctgcctgcct gtgtgtatgg acctgccgta 900
gccagtgggt acgactttga aagggaggga tactctctag tcggaataga ccctttcaga 960
ctgcttcaaa acagccaagt gtacagccta atcagaccaa atgagaatcc agcacacaag 1020
agtcaactgg tgtggatggc atgccattct gccgcatttg aagatctaag agtattaagc 1080
ttcatcaaag ggacgaaggt gctcccaaga gggaagcttt ccactagagg agttcaaatt 1140
gcttccaatg aaaatatgga gactatggaa tcaagtacac ttgaactgag aagcaggtac 1200
tgggccataa ggaccagaag tggaggaaac accaatcaac agagggcatc tgcgggccaa 1260
atcagcatac aacctacgtt ctcagtacag agaaatctcc cttttgacag aacaaccatt 1320
atggcagcat tcaatgggaa tacagagggg agaacatctg acatgaggac cgaaatcata 1380

-continued

```
aggatgatgg aaagtgcaag accagaagat gtgtctttcc aggggcgggg agtcttcgag   1440

ctctcggacg aaaaggcagc gagcccgatc gtgccttcct ttgacatgag taatgaagga   1500

tcttatttct tcggagacaa tgcagaggag tacgacaatt aaagaaaaat acccttgttt   1560

ctact                                                                1565
```

<210> SEQ ID NO 5
<211> LENGTH: 1027
<212> TYPE: DNA
<213> ORGANISM: Influenza virus

<400> SEQUENCE: 5

```
agcaaaagca ggtagatatt gaaagatgag tcttctaacc gaggtcgaaa cgtacgtact     60

ctctatcatc ccgtcaggcc ccctcaaagc cgagatcgca cagagacttg aagatgtctt    120

tgcagggaag aacaccgatc ttgaggttct catggaatgg ctaaagacaa gaccaatcct    180

gtcacctctg actaagggga ttttaggatt tgtgttcacg ctcaccgtgc ccagtgagcg    240

aggactgcag cgtagacgct ttgtccaaaa tgcccttaat gggaacgggg atccaaataa    300

catggacaaa gcagttaaac tgtataggaa gctcaagagg gagataacat tccatggggc    360

caaagaaatc tcactcagtt attctgctgg tgcacttgcc agttgtatgg gcctcatata    420

caacaggatg gggctgtga ccactgaagt ggcatttggc ctggtatgtg caacctgtga    480

acagattgct gactcccagc atcggtctca taggcaaatg gtgacaacaa ccaatccact    540

aatcagacat gagaacagaa tggttttagc cagcactaca gctaaggcta tggagcaaat    600

ggctggatcg agtgagcaag cagcagaggc catggaggtt gctagtcagg ctagacaaat    660

ggtgcaagcg atgagaacca ttgggactca tcctagctcc agtgctggtc tgaaaaatga    720

tcttcttgaa aatttgcagg cctatcagaa acgaatgggg gtgcagatgc aacggttcaa    780

gtgatcctct cactattgcc gcaaatatca ttgggatctt gcacttgaca ttgtggattc    840

ttgatcgtct ttttttcaaa tgcatttacc gtcgctttaa atacggactg aaaggagggc    900

cttctacgga aggagtgcca aagtctatga gggaagaata tcgaaaggaa cagcagagtg    960

ctgtggatgc tgacgatggt cattttgtca gcatagagct ggagtaaaaa actaccttgt   1020

ttctact                                                             1027
```

<210> SEQ ID NO 6
<211> LENGTH: 890
<212> TYPE: DNA
<213> ORGANISM: Influenza virus

<400> SEQUENCE: 6

```
agcaaaagca gggtgacaaa aacataatgg atccaaacac tgtgtcaagc tttcaggtag     60

attgctttct ttggcatgtc cgcaaacgag ttgcagacca agaactaggc gatgccccat    120

tccttgatcg gcttcgccga gatcagaaat ccctaagagg aaggggcagt actctcggtc    180

tggacatcaa gacagccaca cgtgctggaa agcagatagt ggagcggatt ctgaaagaag    240

aatccgatga ggcacttaaa atgaccatgg cctctgtacc tgcgtcgcgt tacctaactg    300

acatgactct tgaggaaatg tcaagggact ggtccatgct catacccaag cagaaagtgg    360

caggccctct ttgtatcaga atggaccagg cgatcatgga taagaacatc atactgaaag    420

cgaacttcag tgtgattttt gaccggctgg agactctaat attgctaagg gctttcaccg    480

aagagggagc aattgttggc gaaatttcac cattgccttc tcttccagga catactgctg    540

aggatgtcaa aaatgcagtt ggagtcctca tcggaggact tgaatggaat gataacacag    600
```

```
ttcgagtctc tgaaactcta cagagattcg cttggagaag cagtaatgag aatgggagac    660

ctccactcac tccaaaacag aaacgagaaa tggcgggaac aattaggtca gaagtttgaa    720

gaaataagat ggttgattga agaagtgaga cacaaactga agataacaga gaatagtttt    780

gagcaaataa catttatgca agccttacat ctattgcttg aagtggagca agagataaga    840

actttctcgt ttcagcttat ttagtactaa aaaacaccct tgtttctact               890
```

<210> SEQ ID NO 7
<211> LENGTH: 1775
<212> TYPE: DNA
<213> ORGANISM: Influenza virus

<400> SEQUENCE: 7

```
agcaaaagca ggggaaaata aaaacaacca aaatgaaggc aaacctactg gtcctgttat     60

gtgcacttgc agctgcagat gcagacacaa tatgtatagg ctaccatgcg aacaattcaa    120

ccgacactgt tgacacagta ctcgagaaga atgtgacagt gacacactct gttaacctgc    180

tcgaagacag ccacaacgga aaactatgta gattaaaagg aatagcccca ctacaattgg    240

ggaaatgtaa catcgccgga tggctcttgg gaaacccaga atgcgaccca ctgcttccag    300

tgagatcatg gtcctacatt gtagaaacac caaactctga gaatggaata tgttatccag    360

gagatttcat cgactatgag gagctgaggg agcaattgag ctcagtgtca tcattcgaaa    420

gattcgaaat atttcccaaa gaaagctcat ggcccaacca caacacaaac ggagtaacgg    480

cagcatgctc ccatgagggg aaaagcagtt tttacagaaa tttgctatgg ctgacggaga    540

aggagggctc atacccaaag ctgaaaaatt cttatgtgaa caaaaaaggg aaagaagtcc    600

ttgtactgtg ggtattcat cacccgccta acagtaagga acaacagaat ctctatcaga    660

atgaaaatgc ttatgtctct gtagtgactt caaattataa caggagattt accccggaaa    720

tagcagaaag acccaaagta agagatcaag ctgggaggat gaactattac tggaccttgc    780

taaaacccgg agacacaata atatttgagg caaatggaaa tctaatagca ccaatgtatg    840

ctttcgcact gagtagaggc tttgggtccg gcatcatcac ctcaaacgca tcaatgcatg    900

agtgtaacac gaagtgtcaa acacccctgg gagctataaa cagcagtctc ccttaccaga    960

atatacaccc agtcacaata ggagagtgcc caaaatacgt caggagtgcc aaattgagga   1020

tggttacagg actaaggaac attccgtcca ttcaatccag aggtctattt ggagccattg   1080

ccggttttat tgaaggggga tggactggaa tgatagatgg atggtatggt tatcatcatc   1140

agaatgaaca gggatcaggc tatgcagcgg atcaaaaaag cacacaaaat gccattaacg   1200

ggattacaaa caaggtgaac actgttatcg agaaaatgaa cattcaattc acagctgtgg   1260

gtaaagaatt caacaaatta gaaaaaagga tggaaaattt aaataaaaaa gttgatgatg   1320

gatttctgga catttggaca tataatgcag aattgttagt tctactggaa aatgaaagga   1380

ctctggattt ccatgactca aatgtgaaga atctgtatga gaaagtaaaa agccaattaa   1440

agaataatgc caaagaaatc ggaaatggat gttttgagtt ctaccacaag tgtgacaatg   1500

aatgcatgga aagtgtaaga aatgggactt atgattatcc caaatattca gaagagtcaa   1560

agttgaacag ggaaaaggta gatggagtga aattggaatc aatggggatc tatcagattc   1620

tggcgatcta ctcaactgtc gccagttcac tggtgctttt ggtctccctg gggcaatca    1680

gtttctggat gtgttctaat ggatctttgc agtgcagaat atgcatctga gattagaatt   1740

tcagagatat gaggaaaaac acccttgttt ctact                              1775
```

-continued

<210> SEQ ID NO 8
<211> LENGTH: 1413
<212> TYPE: DNA
<213> ORGANISM: Influenza virus

<400> SEQUENCE: 8
agcaaaagca ggggtttaaa atgaatccaa atcagaaaat aataaccatt ggatcaatct 60
gtctggtagt cggactaatt agcctaatat tgcaaatagg gaatataatc tcaatatgga 120
ttagccattc aattcaaact ggaagtcaaa accatactgg aatatgcaac caaaacatca 180
ttacctataa aaatagcacc tgggtaaagg acacaacttc agtgatatta accggcaatt 240
catctctttg tcccatccgt gggtgggcta tatacagcaa agacaatagc ataagaattg 300
gttccaaagg agacgttttt gtcataagag agccctttat ttcatgttct cacttggaat 360
gcaggacctt ttttctgacc caaggtgcct tactgaatga caagcattca agtgggactg 420
ttaaggacag aagcccttat agggccttaa tgagctgccc tgtcggtgaa gctccgtccc 480
cgtacaattc aagatttgaa tcggttgctt ggtcagcaag tgcatgtcat gatggcatgg 540
gctggctaac aatcggaatt tcaggtccag ataatggagc agtggctgta ttaaaataca 600
acggcataat aactgaaacc ataaaaagtt ggaggaagaa aatattgagg acacaagagt 660
ctgaatgtgc ctgtgtaaat ggttcatgtt ttactataat gactgatggc ccgagtgatg 720
ggctggcctc gtacaaaatt ttcaagatcg aaaaggggaa ggttactaaa tcaatagagt 780
tgaatgcacc taattctcac tatgaggaat gttcctgtta ccctgatacc ggcaaagtga 840
tgtgtgtgtg cagagacaat tggcatggtt cgaaccggcc atgggtgtct ttcgatcaaa 900
acctggatta tcaaatagga tacatctgca gtggggtttt cggtgacaac ccgcgtcccg 960
aagatggaac aggcagctgt ggtccagtgt atgttgatgg agcaaacgga gtaaagggat 1020
tttcatatag gtatggtaat ggtgtttgga taggaaggac caaaagtcac agttccagac 1080
atgggtttga gatgatttgg gatcctaatg gatggacaga gactgatagt aagttctctg 1140
tgaggcaaga tgttgtggca atgactgatt ggtcagggta tagcggaagt ttcgttcaac 1200
atcctgagct gacagggcta gactgtatga ggccgtgctt ctgggttgaa ttaatcaggg 1260
gacgacctaa agaaaaaaca atctggacta gtgcgagcag catttctttt tgtggcgtga 1320
atagtgatac tgtagattgg tcttggccag acggtgctga gttgccattc agcattgaca 1380
agtagtctgt tcaaaaaact ccttgtttct act 1413

<210> SEQ ID NO 9

<400> SEQUENCE: 9

000

<210> SEQ ID NO 10
<211> LENGTH: 2341
<212> TYPE: DNA
<213> ORGANISM: Influenza virus

<400> SEQUENCE: 10
agcgaaagca ggcaaaccat ttgaatggat gtcaatccga ccttactttt cttaaaagtg 60
ccagcacaaa atgctataag cacaactttc ccttataccg gagaccctcc ttacagccat 120
gggacaggaa caggatacac catggatact gtcaacagga cacatcagta ctcagaaaag 180
ggaagatgga caacaaacac cgaaactgga gcaccgcaac tcaacccgat tgatgggcca 240

-continued

```
ctgccagaag acaatgaacc aagtggttat gcccaaacag attgtgtatt ggaagcaatg    300

gctttccttg aggaatccca tcctggtatt tttgaaaact cgtgtattga aacgatggag    360

gttgttcagc aaacacgagt agacaagctg acacaaggcc gacagaccta tgactggact    420

ttaaatagaa accagcctgc tgcaacagca ttggccaaca caatagaagt gttcagatca    480

aatggcctca cggccaatga gtcaggaagg ctcatagact tccttaagga tgtaatggag    540

tcaatgaaaa aagaagaaat ggggatcaca actcattttc agagaaagag acgggtgaga    600

gacaatatga ctaagaaaat gataacacag agaacaatag gtaaaaggaa acagagattg    660

aacaaaaggg gttatctaat tagagcattg accctgaaca caatgaccaa agatgctgag    720

agagggaagc taaaacggag agcaattgca accccaggga tgcaaataag ggggtttgta    780

tactttgttg agacactggc aaggagtata tgtgagaaac ttgaacaatc agggttgcca    840

gttggaggca atgagaagaa agcaaagttg gcaaatgttg taaggaagat gatgaccaat    900

tctcaggaca ccgaactttc tttcaccatc actggagata acaccaaatg gaacgaaaat    960

cagaatcctc ggatgttttt ggccatgatc acatatatga ccagaaatca gcccgaatgg   1020

ttcagaaatg ttctaagtat tgctccaata atgttctcaa acaaaatggc gagactggga   1080

aaagggtata tgtttgagag caagagtatg aaacttagaa ctcaaatacc tgcagaaatg   1140

ctagcaagca ttgatttgaa atatttcaat gattcaacaa gaaagaagat tgaaaaaatc   1200

cgaccgctct taatagaggg gactgcatca ttgagccctg gaatgatgat gggcatgttc   1260

aatatgttaa gcactgtatt aggcgtctcc atcctgaatc ttggacaaaa gagatacacc   1320

aagactactt actggtggga tggtcttcaa tcctctgacg attttgctct gattgtgaat   1380

gcacccaatc atgaagggat tcaagccgga gtcgacaggt tttatcgaac ctgtaagcta   1440

cttggaatca atatgagcaa gaaaaagtct tacataaaca gaacaggtac atttgaattc   1500

acaagttttt tctatcgtta tgggtttgtt gccaatttca gcatggagct tcccagtttt   1560

ggggtgtctg ggatcaacga gtcagcggac atgagtattg gagttactgt catcaaaaac   1620

aatatgataa acaatgatct tggtccagca acagctcaaa tggcccttca gttgttcatc   1680

aaagattaca ggtacacgta ccgatgccat agaggtgaca cacaaataca aacccgaaga   1740

tcatttgaaa taaagaaact gtgggagcaa acccgttcca aagctggact gctggtctcc   1800

gacggaggcc caaatttata caacattaga aatctccaca ttcctgaagt ctgcctaaaa   1860

tgggaattga tggatgagga ttaccagggg cgtttatgca acccactgaa cccatttgtc   1920

agccataaag aaattgaatc aatgaacaat gcagtgatga tgccagcaca tggtccagcc   1980

aaaaacatgg agtatgatgc tgttgcaaca acacactcct ggatccccaa aagaaatcga   2040

tccatcttga atacaagtca aagaggagta cttgaagatg aacaaatgta ccaaaggtgc   2100

tgcaatttat ttgaaaaatt cttccccagc agttcataca gaagaccagt cgggatatcc   2160

agtatggtgg aggctatggt ttccagagcc cgaattgatg cacggattga tttcgaatct   2220

ggaaggataa agaaagaaga gttcactgag atcatgaaga tctgttccac cattgaagag   2280

ctcagacggc aaaaatagtg aatttagctt gtccttcatg aaaaaatgcc ttgtttctac   2340

t                                                                   2341
```

<210> SEQ ID NO 11
<211> LENGTH: 2341
<212> TYPE: DNA
<213> ORGANISM: Influenza virus

<400> SEQUENCE: 11

-continued

```
agcgaaagca ggtcaattat attcaatatg gaaagaataa aagaactaag aaatctaatg     60
tcgcagtctc gcacccgcga gatactcaca aaaaccaccg tggaccatat ggccataatc    120
aagaagtaca catcaggaag acaggagaag aacccagcac ttaggatgaa atggatgatg    180
gcaatgaaat atccaattac agcagacaag aggataacgg aaatgattcc tgagagaaat    240
gagcaaggac aaactttatg gagtaaaatg aatgatgccg gatcagaccg agtgatggta    300
tcacctctgg ctgtgacatg gtggaatagg aatggaccaa tgacaaatac agttcattat    360
ccaaaaatct acaaaactta ttttgaaaga gtcgaaaggc taaagcatgg aacctttggc    420
cctgtccatt ttagaaacca agtcaaaata cgtcggagag ttgacataaa tcctggtcat    480
gcagatctca gtgccaagga ggcacaggat gtaatcatgg aagttgtttt ccctaacgaa    540
gtgggagcca ggatactaac atcggaatcg caactaacga taaccaaaga gaagaaagaa    600
gaactccagg attgcaaaat ttctcctttg atggttgcat acatgttgga gagagaactg    660
gtccgcaaaa cgagattcct cccagtggct ggtggaacaa gcagtgtgta cattgaagtg    720
ttgcatttga ctcaaggaac atgctgggaa cagatgtata ctccaggagg ggaagtgaag    780
aatgatgatg ttgatcaaag cttgattatt gctgctagga acatagtgag aagagctgca    840
gtatcagcag acccactagc atctttattg gagatgtgcc acagcacaca gattggtgga    900
attaggatgg tagacatcct taagcagaac ccaacagaag agcaagccgt ggatatatgc    960
aaggctgcaa tgggactgag aattagctca tccttcagtt ttggtggatt cacatttaag   1020
agaacaagcg gatcatcagt caagagagag gaagaggtgc ttacgggcaa tcttcaaaca   1080
ttgaagataa gagtgcatga gggatctgaa gagttcacaa tggttgggag aagagcaaca   1140
gccatactca gaaaagcaac caggagattg attcagctga tagtgagtgg gagagacgaa   1200
cagtcgattg ccgaagcaat aattgtggcc atggtatttt cacaagagga ttgtatgata   1260
aaagcagtta gaggtgatct gaatttcgtc aatagggcga atcagcgact gaatcctatg   1320
catcaacttt taagacattt tcagaaggat gcgaaagtgc tttttcaaaa ttggggagtt   1380
gaacctatcg acaatgtgat gggaatgatt gggatattgc ccgacatgac tccaagcatc   1440
gagatgtcaa tgagaggagt gagaatcagc aaaatgggtg tagatgagta ctccagcacg   1500
gagagggtag tggtgagcat tgaccggttc ttgagagtca gggaccaacg aggaaatgta   1560
ctactgtctc ccgaggaggt cagtgaaaca cagggaacag agaaactgac aataacttac   1620
tcatcgtcaa tgatgtggga gattaatggt cctgaatcag tgttggtcaa tacctatcaa   1680
tggatcatca gaaactggga aactgttaaa attcagtggt cccagaaccc tacaatgcta   1740
tacaataaaa tggaatttga accatttcag tctttagtac ctaaggccat tagaggccaa   1800
tacagtgggt ttgtaagaac tctgttccaa caaatgaggg atgtgcttgg gacatttgat   1860
accgcacaga taataaaact tcttcccttc gcagccgctc caccaaagca aagtagaatg   1920
cagttctcct catttactgt gaatgtgagg ggatcaggaa tgagaatact tgtaaggggc   1980
aattctcctg tattcaacta caacaaggcc acgaagagac tcacagttct cggaaaggat   2040
gctggcactt taaccgaaga cccagatgaa ggcacagctg gagtggagtc cgctgttctg   2100
aggggattcc tcattctggg caaagaagac aggagatatg ggccagcatt aagcatcaat   2160
gaactgagca accttgcgaa aggagagaag gctaatgtgc taattgggca aggagacgtg   2220
gtgttggtaa tgaaacgaaa acgggactct agcatactta ctgacagcca gacagcgacc   2280
aaaagaattc ggatggccat caattagtgt cgaatagttt aaaaacgacc ttgtttctac   2340
```

-continued t 2341

<210> SEQ ID NO 12
<211> LENGTH: 2233
<212> TYPE: DNA
<213> ORGANISM: Influenza virus

<400> SEQUENCE: 12
agcgaaagca ggtactgatt caaaatggaa gattttgtgc gacaatgctt caatccgatg 60
attgtcgagc ttgcggaaaa aacaatgaaa gagtatgggg aggacctgaa aatcgaaaca 120
aacaaatttg cagcaatatg cactcacttg gaagtatgct tcatgtattc agatttccac 180
ttcatcaatg agcaaggcga gtcaataatc gtagaacttg gtgatcctaa tgcacttttg 240
aagcacagat ttgaaataat cgagggaaga gatcgcacaa tggcctggac agtagtaaac 300
agtatttgca acactacagg ggctgagaaa ccaaagtttc taccagattt gtatgattac 360
aaggaaaata gattcatcga aattggagta acaaggagag aagttcacat atactatctg 420
gaaaaggcca ataaaattaa atctgagaaa acacacatcc acatttttctc gttcactggg 480 gaagaaatgg ccacaagggc cgactacact ctcgatgaag aaagcagggc taggatcaaa 540
accaggctat tcaccataag acaagaaatg gccagcagag gcctctggga ttcctttcgt 600
cagtccgaga gaggagaaga gacaattgaa gaaaggtttg aaatcacagg aacaatgcgc 660
aagcttgccg accaaagtct cccgccgaac ttctccagcc ttgaaaattt tagagcctat 720
gtggatggat tcgaaccgaa cggctacatt gagggcaagc tgtctcaaat gtccaaagaa 780
gtaaatgcta gaattgaacc tttttttgaaa acaacaccac gaccacttag acttccgaat 840
gggcctccct gttctcagcg gtccaaattc ctgctgatgg atgccttaaa attaagcatt 900
gaggacccaa gtcatgaagg agagggaata ccgctatatg atgcaatcaa atgcatgaga 960
acattctttg gatggaagga acccaatgtt gttaaaccac acgaaaaggg aataaatcca 1020
aattatcttc tgtcatggaa gcaagtactg gcagaactgc aggacattga gaatgaggag 1080
aaaattccaa agactaaaaa tatgaaaaaa acaagtcagc taaagtgggc acttggtgag 1140
aacatggcac cagaaaaggt agactttgac gactgtaaag atgtaggtga tttgaagcaa 1200
tatgatagtg atgaaccaga attgaggtcg cttgcaagtt ggattcagaa tgagttcaac 1260
aaggcatgcg aactgacaga ttcaagctgg atagagcttg atgagattgg agaagatgtg 1320
gctccaattg aacacattgc aagcatgaga aggaattatt tcacatcaga ggtgtctcac 1380
tgcagagcca cagaatacat aatgaagggg gtgtacatca atactgcctt acttaatgca 1440
tcttgtgcag caatggatga tttccaatta attccaatga taagcaagtg tagaactaag 1500
gagggaaggc gaaagaccaa cttgtatggt ttcatcataa aaggaagatc ccacttaagg 1560
aatgacaccg acgtggtaaa ctttgtgagc atggagtttt ctctcactga cccaagactt 1620
gaaccacaca aatgggagaa gtactgtgtt cttgagatag gagatatgct tctaagaagt 1680
gccataggcc aggtttcaag gcccatgttc ttgtatgtga ggacaaatgg aacctcaaaa 1740
attaaaatga aatggggaat ggagatgagg cgttgtctcc tccagtcact tcaacaaatt 1800
gagagtatga ttgaagctga gtcctctgtc aaagagaaag acatgaccaa agagttcttt 1860
gagaacaaat cagaaacatg gcccattgga gagtctccca aaggagtgga ggaaagttcc 1920
attgggaagg tctgcaggac tttattagca aagtcggtat ttaacagctt gtatgcatct 1980
ccacaactag aaggattttc agctgaatca agaaaactgc ttcttatcgt tcaggctctt 2040
agggacaatc tggaacctgg gacctttgat cttgggggc tatatgaagc aattgaggag 2100
tgcctaatta atgatccctg ggttttgctt aatgcttctt ggttcaactc cttccttaca 2160
catgcattga gttagttgtg gcagtgctac tatttgctat ccatactgtc caaaaaagta 2220
ccttgtttct act 2233

<210> SEQ ID NO 13
<211> LENGTH: 1565
<212> TYPE: DNA
<213> ORGANISM: Influenza virus

<400> SEQUENCE: 13
agcaaaagca gggtagataa tcactcactg agtgacatca aaatcatggc gtcccaaggc 60
accaaacggt cttacgaaca gatggagact gatggagaac gccagaatgc cactgaaatc 120
agagcatccg tcggaaaaat gattggtgga attggacgat tctacatcca aatgtgcaca 180
gaacttaaac tcagtgatta tgagggacgg ttgatccaaa acagcttaac aatagagaga 240
atggtgctct ctgcttttga cgaaaggaga aataaatacc tggaagaaca tcccagtgcg 300
gggaaagatc ctaagaaaac tggaggacct atatacagaa gagtaaacgg aaagtggatg 360
agagaactca tcctttatga caaagaagaa ataaggcgaa tctggcgcca agctaataat 420
ggtgacgatg caacggctgg tctgactcac atgatgatct ggcattccaa tttgaatgat 480
gcaacttatc agaggacaag ggctcttgtt cgcaccggaa tggatcccag gatgtgctct 540
ctgatgcaag gttcaactct ccctaggagg tctggagccg caggtgctgc agtcaaagga 600
gttggaacaa tggtgatgga attggtcagg atgatcaaac gtgggatcaa tgatcggaac 660
ttctggaggg gtgagaatgg acgaaaaaca agaattgctt atgaaagaat gtgcaacatt 720
ctcaaaggga aatttcaaac tgctgcacaa aaagcaatga tggatcaagt gagagagagc 780
cggaacccag ggaatgctga gttcgaagat ctcacttttc tagcacggtc tgcactcata 840
ttgagagggt cggttgctca caagtcctgc ctgcctgcct gtgtgtatgg acctgccgta 900
gccagtgggt acgactttga aagagaggga tactctctag tcggaataga ccctttcaga 960
ctgcttcaaa acagccaagt gtacagccta atcagaccaa atgagaatcc agcacacaag 1020
agtcaactgg tgtggatggc atgccattct gccgcatttg aagatctaag agtattgagc 1080
ttcatcaaag ggacgaaggt ggtcccaaga gggaagcttt ccactagagg agttcaaatt 1140
gcttccaatg aaaatatgga gactatggaa tcaagtacac ttgaactgag aagcaggtac 1200
tgggccataa ggaccagaag tggaggaaac accaatcaac agagggcatc tgcgggccaa 1260
atcagcatac aacctacgtt ctcagtacag agaaatctcc cttttgacag aacaaccgtt 1320
atggcagcat tcactgggaa tacagagggg agaacatctg acatgaggac cgaaatcata 1380
aggatgatgg aaagtgcaag accagaagat gtgtctttcc aggggcgggg agtcttcgag 1440
ctctcggacg aaaaggcagc gagcccgatc gtgccttcct ttgacatgag taatgaagga 1500
tcttatttct tcggagacaa tgcagaggag tacgacaatt aaagaaaaat acccttgttt 1560
ctact 1565

<210> SEQ ID NO 14
<211> LENGTH: 1027
<212> TYPE: DNA
<213> ORGANISM: Influenza virus

<400> SEQUENCE: 14
agcaaaagca ggtagatatt gaaagatgag tcttctaacc gaggtcgaaa cgtacgttct 60
ctctatcatc ccgtcaggcc ccctcaaagc cgagatcgca cagagacttg aagatgtctt 120
tgcagggaag aacaccgatc ttgaggttct catggaatgg ctaaagacaa gaccaatcct 180
gtcacctctg actaagggga ttttaggatt tgtgttcacg ctcaccgtgc ccagtgagcg 240
aggactgcag cgtagacgct ttgtccaaaa tgcccttaat gggaacgggg atccaaataa 300
catggacaaa gcagttaaac tgtataggaa gctcaagagg gagataacat tccatggggc 360
caaagaaatc tcactcagtt attctgctgg tgcacttgcc agttgtatgg gcctcatata 420
caacaggatg gggggctgtga ccactgaagt ggcatttggc ctggtatgtg caacctgtga 480
acagattgct gactcccagc atcggtctca taggcaaatg gtgacaacaa ccaacccact 540
aatcagacat gagaacagaa tggttttagc cagcactaca gctaaggcta tggagcaaat 600
ggctggatcg agtgagcaag cagcagaggc catggaggtt gctagtcagg ctaggcaaat 660
ggtgcaagcg atgagaacca ttgggactca tcctagctcc agtgctggtc tgaaaaatga 720
tcttcttgaa aatttgcagg cctatcagaa acgaatgggg gtgcagatgc aacggttcaa 780
gtgatcctct cgctattgcc gcaaatatca ttgggatctt gcacttgata ttgtggattc 840
ttgatcgtct ttttttcaaa tgcatttacc gtcgctttaa atacggactg aaaggagggc 900
cttctacgga aggagtgcca aagtctatga gggaagaata tcgaaaggaa cagcagagtg 960
ctgtggatgc tgacgatggt cattttgtca gcatagagct ggagtaaaaa actaccttgt 1020
ttctact 1027

<210> SEQ ID NO 15
<211> LENGTH: 890
<212> TYPE: DNA
<213> ORGANISM: Influenza virus

<400> SEQUENCE: 15
agcaaaagca gggtgacaaa gacataatgg atccaaacac tgtgtcaagc tttcaggtag 60
attgctttct ttggcatgtc cgcaaacgag ttgcagacca agaactaggt gatgccccat 120
tccttgatcg gcttcgccga gatcagaaat ccctaagagg aaggggcagc actcttggtc 180
tggacatcga gacagccaca cgtgctggaa agcagatagt ggagcggatt ctgaaagaag 240
aatccgatga ggcacttaaa atgaccatgg cctctgtacc tgcgtcgcgt tacctaaccg 300
acatgactct tgaggaaatg tcaagggaat ggtccatgct catacccaag cagaaagtgg 360
caggccctct ttgtatcaga atggaccagg cgatcatgga taaaaacatc atactgaaag 420
cgaacttcag tgtgattttt gaccggctgg agactctaat attgctaagg gctttcaccg 480
aagagggagc aattgttggc gaaatttcac cattgccttc tcttccagga catactgctg 540
aggatgtcaa aaatgcagtt ggagtcctca tcggaggact tgaatggaat gataacacag 600
ttcgagtctc tgaaactcta cagagattcg cttggagaag cagtaatgag aatgggagac 660
ctccactcac tccaaaacag aaacgagaaa tggcgggaac aattaggtca gaagtttgaa 720
gaaataagat ggttgattga agaagtgaga cacaaactga aggtaacaga gaatagtttt 780
gagcaaataa catttatgca agccttacat ctattgcttg aagtggagca agagataaga 840
actttctcat ttcagcttat ttaataataa aaaacaccct tgtttctact 890

<210> SEQ ID NO 16
<211> LENGTH: 319
<212> TYPE: PRT
<213> ORGANISM: Influenza virus

<400> SEQUENCE: 16

```
Ala Thr Leu Cys Leu Gly His His Ala Val Pro Asn Gly Thr Leu Val
1               5                   10                  15

Lys Thr Ile Thr Asp Asp Gln Ile Glu Val Thr Asn Ala Thr Glu Leu
            20                  25                  30

Val Gln Ser Ser Ser Thr Gly Lys Ile Cys Asn Asn Pro His Arg Ile
        35                  40                  45

Leu Asp Gly Ile Asp Cys Thr Leu Ile Asp Ala Leu Leu Gly Asp Pro
    50                  55                  60

His Cys Asp Val Phe Gln Asn Glu Thr Trp Asp Leu Phe Val Glu Arg
65                  70                  75                  80

Ser Lys Ala Phe Ser Asn Cys Tyr Pro Tyr Asp Val Pro Asp Tyr Ala
                85                  90                  95

Ser Leu Arg Ser Leu Val Ala Ser Ser Gly Thr Leu Glu Phe Ile Thr
            100                 105                 110

Glu Gly Phe Thr Trp Thr Gly Val Thr Gln Asn Gly Gly Ser Asn Ala
        115                 120                 125

Cys Lys Arg Gly Pro Gly Ser Gly Phe Phe Ser Arg Leu Asn Trp Leu
    130                 135                 140

Thr Lys Ser Gly Ser Thr Tyr Pro Val Leu Asn Val Thr Met Pro Asn
145                 150                 155                 160

Asn Asp Asn Phe Asp Lys Leu Tyr Ile Trp Gly Ile His His Pro Ser
                165                 170                 175

Thr Asn Gln Glu Gln Thr Ser Leu Tyr Val Gln Ala Ser Gly Arg Val
            180                 185                 190

Thr Val Ser Thr Arg Arg Ser Gln Gln Thr Ile Ile Pro Asn Ile Gly
        195                 200                 205

Ser Arg Pro Trp Val Arg Gly Leu Ser Ser Arg Ile Ser Ile Tyr Trp
    210                 215                 220

Thr Ile Val Lys Pro Gly Asp Val Leu Val Ile Asn Ser Asn Gly Asn
225                 230                 235                 240

Leu Ile Ala Pro Arg Gly Tyr Phe Lys Met Arg Thr Gly Lys Ser Ser
                245                 250                 255

Ile Met Arg Ser Asp Ala Pro Ile Asp Thr Cys Ile Ser Glu Cys Ile
            260                 265                 270

Thr Pro Asn Gly Ser Ile Pro Asn Asp Lys Pro Phe Gln Asn Val Asn
        275                 280                 285

Lys Ile Thr Tyr Gly Ala Cys Pro Lys Tyr Val Lys Gln Asn Thr Leu
    290                 295                 300

Lys Leu Ala Thr Gly Met Arg Asn Val Pro Glu Lys Gln Thr Arg
305                 310                 315
```

<210> SEQ ID NO 17
<211> LENGTH: 326
<212> TYPE: PRT
<213> ORGANISM: Influenza virus

<400> SEQUENCE: 17

```
Asp Gln Ile Cys Ile Gly Tyr His Ala Asn Asn Ser Thr Glu Gln Val
1               5                   10                  15

Asp Thr Ile Met Glu Lys Asn Ile Thr Val Thr His Ala Gln Asp Ile
            20                  25                  30

Leu Glu Lys Thr His Asn Gly Lys Leu Cys Asp Leu Asn Gly Val Lys
        35                  40                  45

Pro Leu Ile Leu Arg Asp Cys Ser Val Ala Gly Trp Leu Leu Gly Asn
```

-continued

```
    50                  55                  60

Pro Met Cys Asp Glu Phe Leu Asn Val Pro Glu Trp Ser Tyr Ile Val
65                  70                  75                  80

Glu Lys Asp Asn Pro Val Asn Gly Leu Cys Tyr Pro Glu Asn Phe Asn
                85                  90                  95

Asp Tyr Glu Glu Leu Lys His Leu Leu Ser Ser Thr Asn His Phe Glu
            100                 105                 110

Lys Ile Arg Ile Ile Pro Arg Ser Ser Trp Ser Asn His Asp Ala Ser
        115                 120                 125

Ser Gly Val Ser Ser Ala Cys Pro Tyr Asn Gly Arg Ser Ser Phe Phe
    130                 135                 140

Arg Asn Val Val Trp Leu Ile Lys Lys Asn Asn Ala Tyr Pro Thr Ile
145                 150                 155                 160

Lys Arg Ser Tyr Asn Asn Thr Asn Gln Glu Asp Leu Leu Ile Leu Trp
                165                 170                 175

Gly Ile His His Pro Asn Asp Ala Ala Glu Gln Thr Lys Leu Tyr Gln
            180                 185                 190

Asn Pro Thr Thr Tyr Val Ser Val Gly Thr Ser Thr Leu Asn Gln Arg
        195                 200                 205

Ser Ile Pro Glu Ile Ala Thr Arg Pro Lys Val Asn Gly Gln Ser Gly
    210                 215                 220

Arg Met Glu Phe Tyr Trp Thr Ile Leu Lys Pro Asn Asp Ala Ile Asn
225                 230                 235                 240

Phe Glu Ser Asn Gly Asn Phe Ile Ala Pro Glu Tyr Ala Tyr Lys Ile
                245                 250                 255

Val Lys Lys Gly Gly Ser Ala Ile Met Lys Ser Gly Leu Glu Tyr Gly
            260                 265                 270

Asn Cys Asn Thr Lys Cys Gln Thr Pro Met Gly Ala Ile Asn Ser Ser
        275                 280                 285

Met Pro Phe His Asn Val His Pro Leu Thr Ile Gly Glu Cys Pro Lys
    290                 295                 300

Tyr Val Lys Ser Gly Arg Leu Val Leu Ala Thr Gly Leu Arg Asn Val
305                 310                 315                 320

Pro Gln Arg Glu Thr Arg
                325


<210> SEQ ID NO 18
<211> LENGTH: 330
<212> TYPE: PRT
<213> ORGANISM: Influenza virus

<400> SEQUENCE: 18

Asp Gln Ile Cys Ile Gly Tyr His Ala Asn Asn Ser Thr Glu Gln Val
1               5                   10                  15

Asp Thr Ile Met Glu Lys Asn Ile Thr Val Thr His Ala Gln Asp Ile
            20                  25                  30

Leu Glu Arg Thr His Asn Gly Lys Leu Cys Asp Leu Asn Gly Val Lys
        35                  40                  45

Pro Leu Ile Leu Arg Asp Cys Ser Val Ala Gly Trp Leu Leu Gly Asn
    50                  55                  60

Pro Met Cys Asp Glu Phe Ile Asn Val Pro Glu Trp Ser Tyr Ile Val
65                  70                  75                  80

Glu Lys Ala Ser Pro Ala Asn Asp Leu Cys Tyr Pro Gly Asn Phe Asn
                85                  90                  95
```

-continued

Asp Tyr Glu Glu Leu Lys His Leu Leu Ser Arg Ile Asn His Phe Glu
100 105 110

Lys Ile Gln Ile Ile Pro Lys Ser Ser Trp Ser Asn His Asp Ala Ser
115 120 125

Ser Gly Val Ser Ser Ala Cys Pro Tyr Leu Gly Arg Ser Ser Phe Phe
130 135 140

Arg Asn Val Val Trp Leu Ile Lys Lys Asn Ser Ala Tyr Pro Thr Ile
145 150 155 160

Lys Arg Ser Tyr Asn Asn Thr Asn Gln Glu Asp Leu Leu Val Leu Trp
165 170 175

Gly Ile His His Pro Asn Asp Ala Ala Glu Gln Thr Lys Leu Tyr Gln
180 185 190

Asn Pro Thr Thr Tyr Val Ser Val Gly Thr Ser Thr Leu Asn Gln Arg
195 200 205

Leu Ile Pro Glu Ile Ala Thr Arg Pro Lys Val Asn Gly Gln Ser Gly
210 215 220

Arg Met Glu Phe Tyr Trp Thr Ile Leu Lys Pro Asn Asp Ala Ile Asn
225 230 235 240

Phe Glu Ser Asn Gly Asn Phe Ile Ala Pro Glu Tyr Ala Tyr Lys Ile
245 250 255

Val Lys Lys Gly Asp Ser Thr Ile Met Lys Ser Glu Leu Glu Tyr Gly
260 265 270

Asn Cys Asn Thr Lys Cys Gln Thr Pro Met Gly Ala Ile Asn Ser Ser
275 280 285

Met Pro Phe His Asn Val His Pro Leu Thr Ile Gly Glu Cys Pro Lys
290 295 300

Tyr Val Lys Ser Asn Arg Leu Val Leu Ala Thr Gly Leu Arg Asn Thr
305 310 315 320

Pro Gln Arg Glu Arg Arg Arg Lys Lys Arg
325 330

<210> SEQ ID NO 19
<211> LENGTH: 325
<212> TYPE: PRT
<213> ORGANISM: Influenza virus

<400> SEQUENCE: 19

Asp Lys Ile Cys Ile Gly Tyr Gln Ser Thr Asn Ser Thr Glu Thr Val
1 5 10 15

Asp Thr Leu Met Glu Thr Asn Ile Pro Val Thr His Ala Lys Asp Ile
20 25 30

Leu His Thr Glu His Asn Gly Met Leu Cys Ala Thr Asn Leu Gly His
35 40 45

Pro Leu Ile Leu Asp Thr Cys Ser Ile Glu Gly Leu Ile Tyr Gly Asn
50 55 60

Pro Ser Cys Asp Leu Leu Leu Gly Gly Arg Glu Trp Ser Tyr Ile Val
65 70 75 80

Glu Lys Pro Ser Pro Val Asn Gly Met Cys Tyr Pro Gly Asn Phe Glu
85 90 95

Asn Leu Glu Glu Leu Lys His Leu Phe Ser Arg Ala Ser Ser Tyr Gln
100 105 110

Arg Ile Gln Ile Ile Pro Asp Thr Ile Trp Asn His Ser Tyr Ser Ser
115 120 125

Gly Thr Ser Arg Ala Cys Ser Asp Ser Phe Phe Arg Ser Met Arg Trp
130 135 140

```
Leu Ile Gln Lys Asn Asn Ala Tyr Pro Thr Gln Asp Ala Gln Tyr Thr
145                 150                 155                 160

Asn Thr Arg Gly Lys Ser Ile Leu Val Met Trp Gly Ile Asn His Pro
                165                 170                 175

Pro Asp Asp Thr Val Gln Thr Asn Leu Tyr Thr Arg Thr Asp Thr Thr
            180                 185                 190

Thr Ser Val Thr Thr Glu Asp Ile Asn Arg Arg Phe Lys Pro Val Ile
        195                 200                 205

Ala Pro Arg Pro Leu Val Asn Gly Gln His Gly Arg Met Asp Tyr Tyr
    210                 215                 220

Trp Ser Ile Leu Lys Pro Asn Gln Thr Ile Arg Phe Arg Ser Asn Gly
225                 230                 235                 240

Asn Phe Ile Ala Pro Trp Tyr Ala His Ile Leu Ser Gly Glu Ser His
                245                 250                 255

Gly Arg Ile Leu Lys Thr Glu Leu Asn Ser Gly Asn Cys Asn Val Gln
            260                 265                 270

Cys Gln Thr Glu Arg Gly Gly Leu Asn Thr Thr Leu Pro Phe His Asn
        275                 280                 285

Val Ser Pro Tyr Ala Ile Gly Asn Cys Pro Lys Tyr Val Gly Val Lys
    290                 295                 300

Ser Leu Val Leu Ala Val Gly Leu Arg Asn Thr Pro Ala Arg Ser Ser
305                 310                 315                 320

Arg Arg Lys Lys Arg
                325


<210> SEQ ID NO 20
<211> LENGTH: 325
<212> TYPE: PRT
<213> ORGANISM: Influenza virus

<400> SEQUENCE: 20

Asp Lys Ile Cys Ile Gly Tyr Gln Ser Thr Asn Ser Thr Glu Thr Val
1               5                   10                  15

Asp Thr Leu Met Glu Thr Asn Ile Pro Val Thr His Ala Lys Asp Ile
            20                  25                  30

Leu His Thr Glu His Asn Gly Met Leu Cys Ala Thr Ser Leu Gly His
        35                  40                  45

Pro Leu Ile Leu Asp Thr Cys Ser Ile Glu Gly Leu Val Tyr Gly Asn
    50                  55                  60

Pro Ser Cys Asp Leu Leu Leu Gly Gly Arg Glu Trp Ser Tyr Ile Val
65                  70                  75                  80

Glu Lys Pro Ser Pro Val Asn Gly Thr Cys Tyr Pro Gly Asn Phe Glu
                85                  90                  95

Asn Leu Glu Glu Leu Lys Thr Leu Phe Ser Arg Ala Ser Ser Tyr Gln
            100                 105                 110

Arg Ile Gln Ile Ile Pro Asp Thr Ile Trp Asn His Ser Tyr Thr Ser
        115                 120                 125

Gly Thr Ser Arg Ala Cys Ser Gly Ser Phe Phe Arg Ser Met Arg Trp
    130                 135                 140

Leu Ile Gln Lys Ser Gly Phe Tyr Pro Thr Gln Asp Ala Gln Tyr Thr
145                 150                 155                 160

Asn Thr Arg Gly Lys Ser Ile Leu Val Met Trp Gly Ile Asn His Pro
                165                 170                 175

Pro Asp Tyr Thr Val Gln Thr Asn Leu Tyr Thr Arg Asn Asp Thr Thr
```

-continued

```
            180                 185                 190

Thr Ser Val Thr Thr Glu Asp Leu Asn Arg Arg Phe Lys Pro Val Ile
        195                 200                 205

Ala Pro Arg Pro Leu Val Asn Gly Gln Gln Gly Arg Met Asp Tyr Tyr
    210                 215                 220

Trp Ser Ile Leu Lys Pro Asn Gln Thr Ile Arg Phe Arg Ser Asn Gly
225                 230                 235                 240

Asn Phe Ile Ala Pro Trp Tyr Ala His Val Leu Ser Gly Gly Ser His
                245                 250                 255

Gly Arg Ile Leu Lys Thr Glu Leu Lys Gly Gly Asn Cys Asn Val Gln
            260                 265                 270

Cys Gln Thr Glu Lys Gly Gly Leu Asn Ser Thr Leu Pro Phe His Asn
        275                 280                 285

Val Ser Pro Tyr Ala Ile Gly Thr Cys Pro Lys Tyr Val Arg Val Lys
    290                 295                 300

Ser Leu Val Leu Ala Val Gly Leu Arg Asn Thr Pro Ala Arg Ser Ser
305                 310                 315                 320

Arg Arg Lys Lys Arg
                325


<210> SEQ ID NO 21
<211> LENGTH: 566
<212> TYPE: PRT
<213> ORGANISM: Influenza virus

<400> SEQUENCE: 21

Met Lys Ala Ile Leu Val Val Leu Leu Tyr Thr Phe Ala Thr Ala Asn
1               5                   10                  15

Ala Asp Thr Leu Cys Ile Gly Tyr His Ala Asn Asn Ser Thr Asp Thr
            20                  25                  30

Val Asp Thr Val Leu Glu Lys Asn Val Thr Val Thr His Ser Val Asn
        35                  40                  45

Leu Leu Glu Asp Lys His Asn Gly Lys Leu Cys Lys Leu Arg Gly Val
    50                  55                  60

Ala Pro Leu His Leu Gly Lys Cys Asn Ile Ala Gly Trp Ile Leu Gly
65                  70                  75                  80

Asn Pro Glu Cys Glu Ser Leu Ser Thr Ala Ser Ser Trp Ser Tyr Ile
                85                  90                  95

Val Glu Thr Pro Ser Ser Asp Asn Gly Thr Cys Tyr Pro Gly Asp Phe
            100                 105                 110

Ile Asp Tyr Glu Glu Leu Arg Glu Gln Leu Ser Ser Val Ser Ser Phe
        115                 120                 125

Glu Arg Phe Glu Ile Phe Pro Lys Thr Ser Ser Trp Pro Asn His Asp
    130                 135                 140

Ser Asn Lys Gly Val Thr Ala Ala Cys Pro His Ala Gly Ala Lys Ser
145                 150                 155                 160

Phe Tyr Lys Asn Leu Ile Trp Leu Val Lys Lys Gly Asn Ser Tyr Pro
                165                 170                 175

Lys Leu Ser Lys Ser Tyr Ile Asn Asp Lys Gly Lys Glu Val Leu Val
            180                 185                 190

Leu Trp Gly Ile His His Pro Ser Thr Ser Ala Asp Gln Gln Ser Leu
        195                 200                 205

Tyr Gln Asn Ala Asp Ala Tyr Val Phe Val Gly Ser Ser Arg Tyr Ser
    210                 215                 220
```

Lys Lys Phe Lys Pro Glu Ile Ala Ile Arg Pro Lys Val Arg Asp Gln
225 230 235 240

Glu Gly Arg Met Asn Tyr Tyr Trp Thr Leu Val Glu Pro Gly Asp Lys
245 250 255

Ile Thr Phe Glu Ala Thr Gly Asn Leu Val Val Pro Arg Tyr Ala Phe
260 265 270

Ala Met Glu Arg Asn Ala Gly Ser Gly Ile Ile Ile Ser Asp Thr Pro
275 280 285

Val His Asp Cys Asn Thr Thr Cys Gln Thr Pro Lys Gly Ala Ile Asn
290 295 300

Thr Ser Leu Pro Phe Gln Asn Ile His Pro Ile Thr Ile Gly Lys Cys
305 310 315 320

Pro Lys Tyr Val Lys Ser Thr Lys Leu Arg Leu Ala Thr Gly Leu Arg
325 330 335

Asn Ile Pro Ser Ile Gln Ser Arg Gly Leu Phe Gly Ala Ile Ala Gly
340 345 350

Phe Ile Glu Gly Gly Trp Thr Gly Met Val Asp Gly Trp Tyr Gly Tyr
355 360 365

His His Gln Asn Glu Gln Gly Ser Gly Tyr Ala Ala Asp Leu Lys Ser
370 375 380

Thr Gln Asn Ala Ile Asp Glu Ile Thr Asn Lys Val Asn Ser Val Ile
385 390 395 400

Glu Lys Met Asn Thr Gln Phe Thr Ala Val Gly Lys Glu Phe Asn His
405 410 415

Leu Glu Lys Arg Ile Glu Asn Leu Asn Lys Lys Val Asp Asp Gly Phe
420 425 430

Leu Asp Ile Trp Thr Tyr Asn Ala Glu Leu Leu Val Leu Leu Glu Asn
435 440 445

Glu Arg Thr Leu Asp Tyr His Asp Ser Asn Val Lys Asn Leu Tyr Glu
450 455 460

Lys Val Arg Ser Gln Leu Lys Asn Asn Ala Lys Glu Ile Gly Asn Gly
465 470 475 480

Cys Phe Glu Phe Tyr His Lys Cys Asp Asn Thr Cys Met Glu Ser Val
485 490 495

Lys Asn Gly Thr Tyr Asp Tyr Pro Lys Tyr Ser Glu Glu Ala Lys Leu
500 505 510

Asn Arg Glu Glu Ile Asp Gly Val Lys Leu Glu Ser Thr Arg Ile Tyr
515 520 525

Gln Ile Leu Ala Ile Tyr Ser Thr Val Ala Ser Ser Leu Val Leu Val
530 535 540

Val Ser Leu Gly Ala Ile Ser Phe Trp Met Cys Ser Asn Gly Ser Leu
545 550 555 560

Gln Cys Arg Ile Cys Ile
565

<210> SEQ ID NO 22
<211> LENGTH: 231
<212> TYPE: PRT
<213> ORGANISM: Influenza virus

<400> SEQUENCE: 22

Arg Asn Ile Pro Ser Ile Gln Ser Arg Gly Leu Phe Gly Ala Ile Ala
1 5 10 15

Gly Phe Ile Glu Gly Gly Trp Thr Gly Met Val Asp Gly Trp Tyr Gly
20 25 30

Tyr His His Gln Asn Glu Gln Gly Ser Gly Tyr Ala Ala Asp Leu Lys
35 40 45

Ser Thr Gln Asn Ala Ile Asp Glu Ile Thr Asn Lys Val Asn Ser Val
50 55 60

Ile Glu Lys Met Asn Thr Gln Phe Thr Ala Val Gly Lys Glu Phe Asn
65 70 75 80

His Leu Glu Lys Arg Ile Glu Asn Leu Asn Lys Lys Val Asp Asp Gly
85 90 95

Phe Leu Asp Ile Trp Thr Tyr Asn Ala Glu Leu Leu Val Leu Leu Glu
100 105 110

Asn Glu Arg Thr Leu Asp Tyr His Asp Ser Asn Val Lys Asn Leu Tyr
115 120 125

Glu Lys Val Arg Ser Gln Leu Lys Asn Asn Ala Lys Glu Ile Gly Asn
130 135 140

Gly Cys Phe Glu Phe Tyr His Lys Cys Asp Asn Thr Cys Met Glu Ser
145 150 155 160

Val Lys Asn Gly Thr Tyr Asp Tyr Pro Lys Tyr Ser Glu Glu Ala Lys
165 170 175

Leu Asn Arg Glu Glu Ile Asp Gly Val Lys Leu Glu Ser Thr Arg Ile
180 185 190

Tyr Gln Ile Leu Ala Ile Tyr Ser Thr Val Ala Ser Ser Leu Val Leu
195 200 205

Val Val Ser Leu Gly Ala Ile Ser Phe Trp Met Cys Ser Asn Gly Ser
210 215 220

Leu Gln Cys Arg Ile Cys Ile
225 230

<210> SEQ ID NO 23
<211> LENGTH: 221
<212> TYPE: PRT
<213> ORGANISM: Influenza virus

<400> SEQUENCE: 23

Gly Leu Phe Gly Ala Ile Ala Gly Phe Ile Glu Asn Gly Trp Glu Gly
1 5 10 15

Met Ile Asp Gly Trp Tyr Gly Phe Arg His Gln Asn Ser Glu Gly Thr
20 25 30

Gly Gln Ala Ala Asp Leu Lys Ser Thr Gln Ala Ala Ile Asp Gln Ile
35 40 45

Asn Gly Lys Leu Asn Arg Val Ile Glu Lys Thr Asn Glu Lys Phe His
50 55 60

Gln Ile Glu Lys Glu Phe Ser Glu Val Glu Gly Arg Ile Gln Asp Leu
65 70 75 80

Glu Lys Tyr Val Glu Asp Thr Lys Ile Asp Leu Trp Ser Tyr Asn Ala
85 90 95

Glu Leu Leu Val Ala Leu Glu Asn Gln His Thr Ile Asp Leu Thr Asp
100 105 110

Ser Glu Met Asn Lys Leu Phe Glu Lys Thr Arg Arg Gln Leu Arg Glu
115 120 125

Asn Ala Glu Glu Met Gly Asn Gly Cys Phe Lys Ile Tyr His Lys Cys
130 135 140

Asp Asn Ala Cys Ile Glu Ser Ile Arg Asn Gly Thr Tyr Asp His Asp
145 150 155 160

Val Tyr Arg Asp Glu Ala Leu Asn Asn Arg Phe Gln Ile Lys Gly Val

```
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Val Leu Leu Gly Phe Ile Met Trp
        195                 200                 205

Ala Cys Gln Arg Gly Asn Ile Arg Cys Asn Ile Cys Ile
    210                 215                 220


<210> SEQ ID NO 24
<211> LENGTH: 222
<212> TYPE: PRT
<213> ORGANISM: Influenza virus

<400> SEQUENCE: 24

Gly Leu Phe Gly Ala Ile Ala Gly Phe Ile Glu Gly Gly Trp Gln Gly
1               5                   10                  15

Met Ile Asp Gly Trp Tyr Gly Phe His His Ser Asn Glu Gln Gly Ser
            20                  25                  30

Gly Tyr Ala Ala Asp Lys Glu Ser Thr Gln Lys Ala Ile Asp Gly Thr
        35                  40                  45

Thr Asn Lys Val Asn Ser Val Ile Asp Lys Met Asn Thr Gln Phe Glu
    50                  55                  60

Ala Ile Gly Lys Glu Phe Asn Asn Leu Glu Arg Arg Ile Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Lys Asn Leu Phe Asp Lys Val Arg Leu Gln Leu Arg Asp
        115                 120                 125

Asn Ala Lys Glu Leu Gly Asn Gly Cys Phe Glu Phe Tyr His Lys Cys
    130                 135                 140

Asp Asn Glu Cys Met Glu Ser Ile Lys Asn Gly Thr Tyr Asp Tyr Pro
145                 150                 155                 160

Gln Tyr Ser Glu Glu Ala Arg Leu Asn Arg Glu Glu Ile Ser Gly Val
                165                 170                 175

Lys Leu Glu Ser Met Gly Ile Tyr Gln Ile Leu Ser Ile Tyr Ser Thr
            180                 185                 190

Val Ala Ser Ser Leu Ala Leu Ala Val Met Ile Ala Gly Leu Ser Leu
        195                 200                 205

Trp Met Cys Ser Asn Gly Ser Leu Gln Cys Arg Ile Cys Ile
    210                 215                 220


<210> SEQ ID NO 25
<211> LENGTH: 222
<212> TYPE: PRT
<213> ORGANISM: Influenza virus

<400> SEQUENCE: 25

Gly Leu Phe Gly Ala Ile Ala Gly Phe Ile Glu Gly Gly Trp Gln Gly
1               5                   10                  15

Met Ile Asp Gly Trp Tyr Gly Phe His His Ser Asn Glu Gln Gly Ser
            20                  25                  30

Gly Tyr Ala Ala Asp Lys Glu Ser Thr Gln Lys Ala Ile Asp Gly Thr
        35                  40                  45

Thr Asn Lys Val Asn Ser Val Ile Asn Lys Met Asn Thr Gln Phe Glu
```

```
    50                  55                  60

Ala Ile Gly Arg Glu Phe Asn Asn Leu Glu Arg Arg Ile Glu Asn Leu
65                  70                  75                  80

Asn Lys Lys Met Glu Asp Gly Phe Leu Asp Val Trp Thr Tyr Asn Ala
                85                  90                  95

Glu Leu Leu Val Leu Met Glu Asn Glu Arg Thr Leu Asp Phe His Asp
            100                 105                 110

Ser Asn Val Lys Asn Leu Phe Asp Lys Val Arg Leu Gln Leu Arg Asp
        115                 120                 125

Asn Ala Lys Glu Leu Gly Asn Gly Cys Phe Glu Phe Tyr His Lys Cys
    130                 135                 140

Asp Asn Glu Cys Met Glu Ser Ile Lys Asn Gly Thr Tyr Asp Tyr Pro
145                 150                 155                 160

Gln Tyr Ser Glu Glu Ala Arg Leu Asn Arg Glu Glu Ile Ser Gly Val
                165                 170                 175

Lys Leu Glu Ser Met Gly Thr Tyr Gln Ile Leu Ser Ile Tyr Ser Thr
            180                 185                 190

Val Ala Ser Ser Leu Ala Leu Ala Val Met Val Ala Gly Leu Ser Leu
        195                 200                 205

Trp Met Cys Ser Asn Gly Ser Leu Gln Cys Arg Ile Cys Ile
    210                 215                 220


<210> SEQ ID NO 26
<211> LENGTH: 212
<212> TYPE: PRT
<213> ORGANISM: Influenza virus

<400> SEQUENCE: 26

Gly Leu Phe Gly Ala Ile Ala Gly Phe Ile Glu Gly Gly Trp Pro Gly
1               5                   10                  15

Leu Ile Ala Gly Trp Tyr Gly Phe Gln His Ser Asn Asp Gln Gly Val
            20                  25                  30

Gly Met Ala Ala Asp Arg Asp Ser Thr Gln Lys Ala Ile Asp Lys Thr
        35                  40                  45

Thr Ser Lys Val Asn Asn Val Ile Asp Lys Met Asn Lys Gln Phe Gly
    50                  55                  60

Ile Ile Asp His Glu Phe Asn Asn Leu Glu Thr Arg Leu Asn Met Ile
65                  70                  75                  80

Asn Asn Lys Met Asp Asp Gln Ile Gln Asp Ile Trp Thr Tyr Asn Ala
                85                  90                  95

Glu Leu Leu Val Leu Met Glu Asn Glu Lys Thr Leu Asp Glu His Asp
            100                 105                 110

Ala Asn Val Lys Asn Leu Phe Asn Lys Val Lys Leu Ala Leu Gly Ser
        115                 120                 125

Asn Ala Met Glu Asp Gly Lys Gly Cys Phe Glu Leu Tyr His Lys Cys
    130                 135                 140

Asp Asp Gln Cys Met Glu Thr Ile Lys Asn Gly Thr Tyr Asn Arg Arg
145                 150                 155                 160

Lys Tyr Lys Glu Glu Ser Lys Leu Glu Arg Gln Lys Ile Glu Gly Val
                165                 170                 175

Lys Leu Glu Ser Glu Gly Thr Tyr Lys Ile Leu Thr Ile Tyr Ser Thr
            180                 185                 190

Val Ala Ser Ser Leu Val Ile Ala Met Gly Phe Ala Ala Leu Leu Phe
        195                 200                 205
```

Trp Met Met Ser
    210

<210> SEQ ID NO 27
<211> LENGTH: 175
<212> TYPE: PRT
<213> ORGANISM: Influenza virus

<400> SEQUENCE: 27

```
Gly Leu Phe Gly Ala Ile Ala Gly Phe Ile Glu Gly Gly Trp Pro Gly
1               5                   10                  15

Leu Ile Ala Gly Trp Tyr Gly Phe Gln His Ser Asn Asp Gln Gly Val
            20                  25                  30

Gly Met Ala Ala Asp Arg Asp Ser Thr Gln Lys Ala Ile Asp Lys Thr
        35                  40                  45

Thr Ser Lys Val Asn Asn Val Ile Asp Lys Met Asn Lys Gln Phe Glu
    50                  55                  60

Ile Ile Asp His Glu Phe Asn Asn Leu Glu Thr Arg Leu Asn Met Ile
65                  70                  75                  80

Asn Asn Lys Met Asp Asp Gln Ile Gln Asp Val Trp Ala Tyr Asn Ala
                85                  90                  95

Glu Leu Leu Val Leu Met Glu Asn Glu Lys Thr Leu Asp Glu His Asp
            100                 105                 110

Ala Asn Val Lys Asn Leu Phe Asn Lys Val Lys Leu Ala Leu Gly Ser
        115                 120                 125

Asn Ala Met Glu Asp Gly Lys Gly Cys Phe Glu Leu Tyr His Lys Cys
    130                 135                 140

Asp Asp Gln Cys Met Glu Thr Ile Lys Asn Gly Thr Tyr Asn Arg Arg
145                 150                 155                 160

Lys Tyr Lys Glu Glu Ser Arg Leu Glu Arg Gln Lys Ile Glu Gly
                165                 170                 175
```

<210> SEQ ID NO 28
<211> LENGTH: 222
<212> TYPE: PRT
<213> ORGANISM: Influenza virus

<400> SEQUENCE: 28

```
Gly Leu Phe Gly Ala Ile Ala Gly Phe Ile Glu Gly Gly Trp Thr Gly
1               5                   10                  15

Met Val Asp Gly Trp Tyr Gly Tyr His His Gln Asn Glu Gln Gly Ser
            20                  25                  30

Gly Tyr Ala Ala Asp Gln Lys Ser Thr Gln Asn Ala Ile Asn Gly Ile
        35                  40                  45

Thr Asn Lys Val Asn Ser Val Ile Glu Lys Met Asn Thr Gln Phe Thr
    50                  55                  60

Ala Val Gly Lys Glu Phe Asn Lys Leu Glu Arg Arg Met Glu Asn Leu
65                  70                  75                  80

Asn Lys Lys Val Asp Asp Gly Phe Leu Asp Ile Trp Thr Tyr Asn Ala
                85                  90                  95

Glu Leu Leu Val Leu Leu Glu Asn Glu Arg Thr Leu Asp Phe His Asp
            100                 105                 110

Ser Asn Val Lys Asp Leu Tyr Glu Lys Val Lys Ser Gln Leu Lys Asn
        115                 120                 125

Asn Ala Lys Glu Ile Gly Asn Gly Cys Phe Glu Phe Tyr His Lys Cys
    130                 135                 140
```

-continued

```
Asn Asn Glu Cys Met Glu Ser Val Lys Asn Gly Thr Tyr Asp Tyr Pro
145                 150                 155                 160

Lys Tyr Ser Glu Glu Ser Lys Leu Asn Arg Glu Lys Ile Asp Gly Val
                165                 170                 175

Lys Leu Glu Ser Met Gly Val Tyr Gln Ile Leu Ala Ile Tyr Ser Thr
            180                 185                 190

Val Ala Ser Ser Leu Val Leu Leu Val Ser Leu Gly Ala Ile Ser Phe
        195                 200                 205

Trp Met Cys Ser Asn Gly Ser Leu Gln Cys Arg Ile Cys Ile
    210                 215                 220


<210> SEQ ID NO 29
<211> LENGTH: 222
<212> TYPE: PRT
<213> ORGANISM: Influenza virus

<400> SEQUENCE: 29

Gly Leu Phe Gly Ala Ile Ala Gly Phe Ile Glu Gly Gly Trp Thr Gly
1               5                   10                  15

Met Val Asp Gly Trp Tyr Gly Tyr His His Gln Asn Glu Gln Gly Ser
            20                  25                  30

Gly Tyr Ala Ala Asp Gln Lys Ser Thr Gln Asn Ala Ile Asn Gly Ile
        35                  40                  45

Thr Asn Lys Val Asn Ser Val Ile Glu Lys Met Asn Thr Gln Phe Thr
    50                  55                  60

Ala Val Gly Lys Glu Phe Asn Lys Leu Glu Arg Arg Met Glu Asn Leu
65                  70                  75                  80

Asn Lys Lys Val Asp Asp Gly Phe Ile Asp Ile Trp Thr Tyr Asn Ala
                85                  90                  95

Glu Leu Leu Val Leu Leu Glu Asn Glu Arg Thr Leu Asp Phe His Asp
            100                 105                 110

Ser Asn Val Lys Asp Leu Tyr Glu Lys Val Lys Ser Gln Leu Lys Asn
        115                 120                 125

Asn Ala Lys Glu Ile Gly Asn Gly Cys Phe Glu Phe Tyr His Lys Cys
    130                 135                 140

Asn Asp Glu Cys Met Glu Ser Val Lys Asn Gly Thr Tyr Asp Tyr Pro
145                 150                 155                 160

Lys Tyr Ser Glu Glu Ser Lys Leu Asn Arg Glu Lys Ile Asp Gly Val
                165                 170                 175

Lys Leu Glu Ser Met Gly Val Tyr Gln Ile Leu Ala Ile Tyr Ser Thr
            180                 185                 190

Val Ala Ser Ser Leu Val Leu Leu Val Ser Leu Gly Ala Ile Ser Phe
        195                 200                 205

Trp Met Cys Ser Asn Gly Ser Leu Gln Cys Arg Ile Cys Ile
    210                 215                 220


<210> SEQ ID NO 30
<211> LENGTH: 221
<212> TYPE: PRT
<213> ORGANISM: Influenza virus

<400> SEQUENCE: 30

Gly Ile Phe Gly Ala Ile Ala Gly Phe Ile Glu Asn Gly Trp Glu Gly
1               5                   10                  15

Met Val Asp Gly Trp Tyr Gly Phe Arg His Gln Asn Ser Glu Gly Thr
            20                  25                  30
```

-continued

```
Gly Gln Ala Ala Asp Leu Lys Ser Thr Gln Ala Ala Ile Asn Gln Ile
        35                  40                  45

Asn Gly Lys Leu Asn Arg Leu Ile Gly Lys Thr Asn Glu Lys Phe His
    50                  55                  60

Gln Ile Glu Lys Glu Phe Ser Glu Val Glu Gly Arg Ile Gln Asp Leu
65                  70                  75                  80

Glu Lys Tyr Val Glu Asp Thr Lys Ile Asp Leu Trp Ser Tyr Asn Ala
                85                  90                  95

Glu Leu Leu Val Ala Leu Glu Asn Gln His Thr Ile Asp Leu Thr Asp
            100                 105                 110

Ser Glu Met Asp Lys Leu Phe Glu Arg Thr Lys Lys Gln Leu Arg Glu
        115                 120                 125

Asn Ala Glu Asp Met Gly Asn Gly Cys Phe Lys Ile Tyr His Lys Cys
    130                 135                 140

Asp Asn Ala Cys Ile Glu Ser Ile Arg Asn Gly Thr Tyr Asp His Asp
145                 150                 155                 160

Val Tyr Arg Asp Glu Ala Leu Asn Asn Arg Phe Gln Ile Lys Gly Val
                165                 170                 175

Glu Leu Lys Ser Gly Tyr Lys Asp Trp Ile Leu Trp Ile Ser Phe Ala
            180                 185                 190

Ile Ser Cys Phe Leu Leu Cys Val Ala Leu Leu Gly Phe Ile Met Trp
        195                 200                 205

Ala Cys Gln Lys Gly Asn Ile Arg Cys Asn Ile Cys Ile
    210                 215                 220
```